United States Patent
Stein et al.

(10) Patent No.: US 9,351,782 B2
(45) Date of Patent: May 31, 2016

(54) MEDICAL DEVICE MOTION AND ORIENTATION TRACKING SYSTEM

(71) Applicant: Shirley J Vaughn, Prescott Valley, AZ (US)

(72) Inventors: Marc Stein, Chandler, AZ (US); Glen Vaughn, Sedona, AZ (US); Shirley J Vaughn, Prescott Valley, AZ (US)

(73) Assignee: ORTHOSENSOR INC., Dania Beach, FL (US)

( * ) Notice: Subject to any disclaimer, the term of this patent is extended or adjusted under 35 U.S.C. 154(b) by 40 days.

(21) Appl. No.: 13/673,964

(22) Filed: Nov. 9, 2012

(65) Prior Publication Data

US 2014/0135616 A1    May 15, 2014

(51) Int. Cl.
| | |
|---|---|
| *A61B 19/00* | (2006.01) |
| *A61B 17/92* | (2006.01) |
| *A61F 2/46* | (2006.01) |
| *G06F 19/00* | (2011.01) |
| *A61B 17/17* | (2006.01) |
| *A61B 17/00* | (2006.01) |
| *G01P 15/18* | (2013.01) |

(52) U.S. Cl.
CPC ............ *A61B 17/92* (2013.01); *A61B 17/1703* (2013.01); *A61B 17/1746* (2013.01); *A61B 19/5244* (2013.01); *A61F 2/4611* (2013.01); *G06F 19/3406* (2013.01); *G06F 19/3481* (2013.01); *A61B 19/2203* (2013.01); *A61B 19/56* (2013.01); *A61B 2017/00725* (2013.01); *A61B 2017/00734* (2013.01); *A61B 2019/5248* (2013.01); *G01P 15/18* (2013.01)

(58) Field of Classification Search
CPC ........... A61B 19/2203; A61B 17/1703; A61B 17/1746; A61B 17/92; A61B 19/201; A61B 19/5244; A61B 19/56; A61B 117/00725; A61B 17/00734; A61B 2019/5248
USPC ................ 600/117, 118, 407, 424, 426, 439; 250/334; 606/130
See application file for complete search history.

(56) References Cited

U.S. PATENT DOCUMENTS

| | | | | |
|---|---|---|---|---|
| 6,122,538 | A * | 9/2000 | Sliwa et al. | 600/407 |
| 6,690,963 | B2 * | 2/2004 | Ben-Haim et al. | 600/424 |
| 6,697,664 | B2 | 2/2004 | Kienzle, III | |
| 6,711,432 | B1 | 3/2004 | Krause | |

(Continued)

FOREIGN PATENT DOCUMENTS

| | | |
|---|---|---|
| EP | 1057455 A3 | 11/2002 |
| EP | 1700574 A1 | 9/2006 |

(Continued)

*Primary Examiner* — Baisakhi Roy

(57) ABSTRACT

A prosthetic hip installation system comprising a reamer, an impactor, a tracking element, and a remote system. The tracking element can be integrated into the reamer or impactor for providing tracking data on the position or orientation. Alternatively, the tracking element can be housed in a separate module that can be coupled to either the reamer or impactor. The tracking element will couple to a predetermined location. Points in 3D space can be registered to provide a frame of reference for the tracking element or when the tracking element is moved from tool to tool. The tracking element sends data from the reamer or impactor wirelessly. The remote system receives the tracking data and can further process the data. A display on the remote system can support placement and orientation of the tool to aid in the installation of the prosthetic component.

22 Claims, 39 Drawing Sheets

(56) References Cited

U.S. PATENT DOCUMENTS

| | | | |
|---|---|---|---|
| 7,993,341 B2 | 8/2011 | Grimm | |
| 8,046,050 B2 | 10/2011 | Govari | |
| 8,277,455 B2 | 10/2012 | Amiot | |
| 8,522,612 B1 * | 9/2013 | Kubena | 73/504.04 |
| 2001/0051761 A1 * | 12/2001 | Khadem | 600/117 |
| 2002/0010384 A1 * | 1/2002 | Shahidi et al. | 600/118 |
| 2006/0161052 A1 | 7/2006 | Colombet | |
| 2006/0282063 A1 * | 12/2006 | Gotani | 606/1 |
| 2007/0023477 A1 * | 2/2007 | Whitman et al. | 227/175.1 |
| 2008/0269596 A1 | 10/2008 | Revie | |
| 2010/0155599 A1 * | 6/2010 | Godavarty et al. | 250/334 |
| 2011/0105895 A1 * | 5/2011 | Kornblau et al. | 600/426 |
| 2012/0209117 A1 * | 8/2012 | Mozes et al. | 600/439 |
| 2014/0052149 A1 * | 2/2014 | van der Walt et al. | 606/130 |

FOREIGN PATENT DOCUMENTS

| | | |
|---|---|---|
| EP | 1996108 A1 | 12/2008 |
| EP | 2467080 A1 | 6/2012 |

* cited by examiner

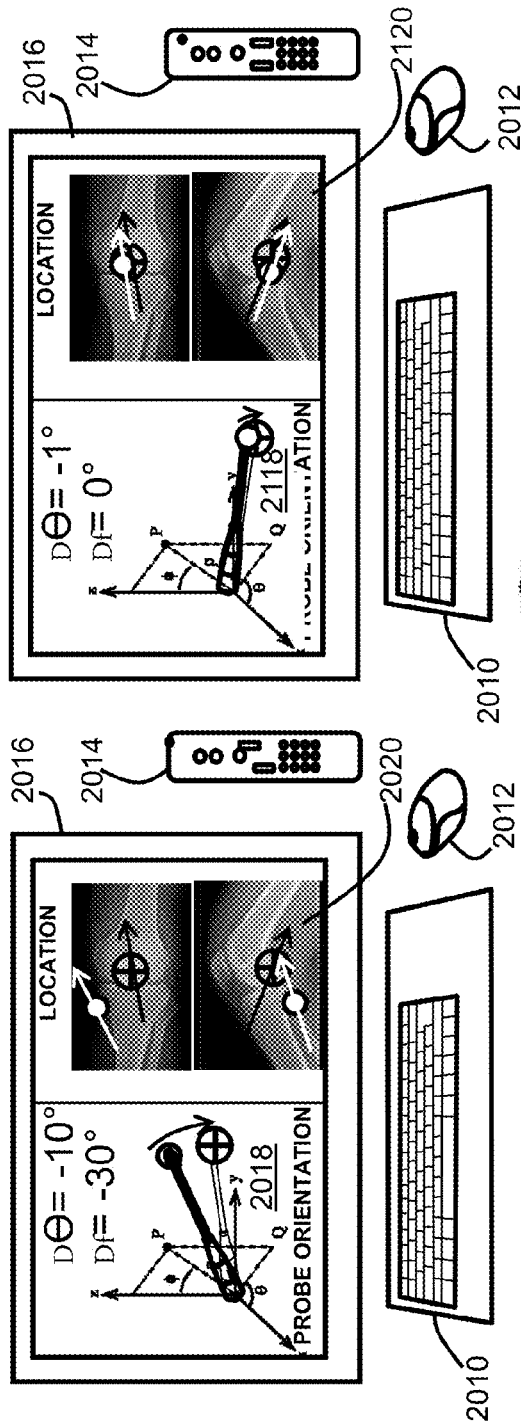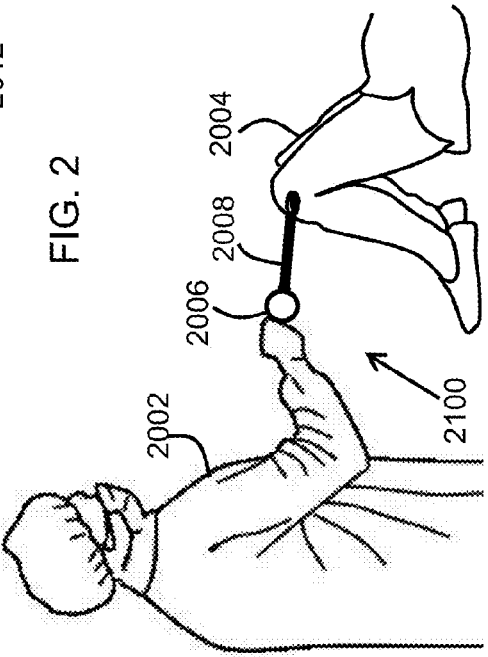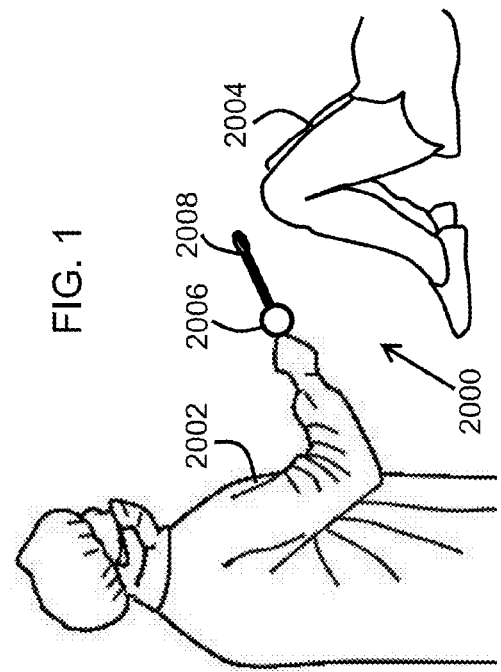

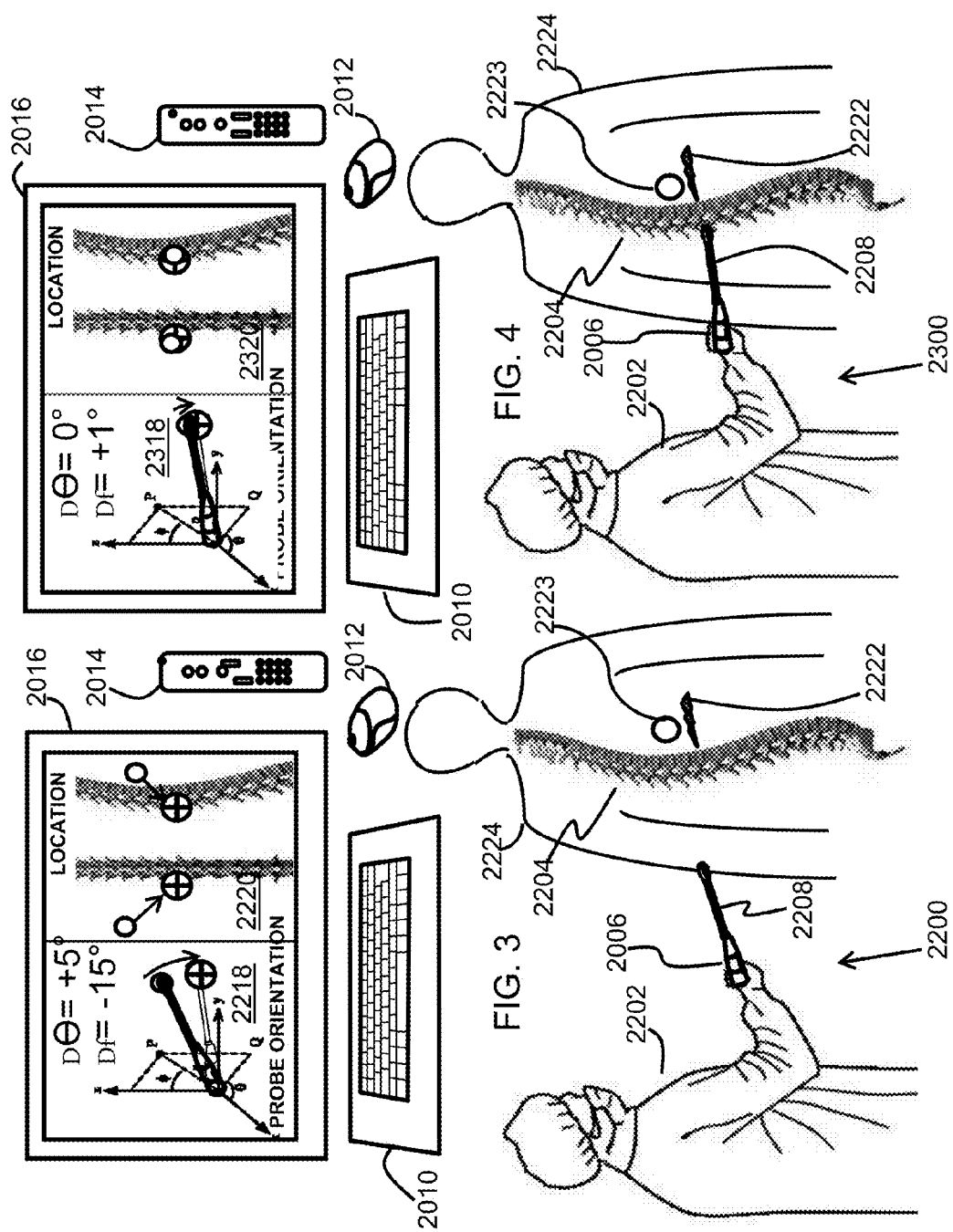

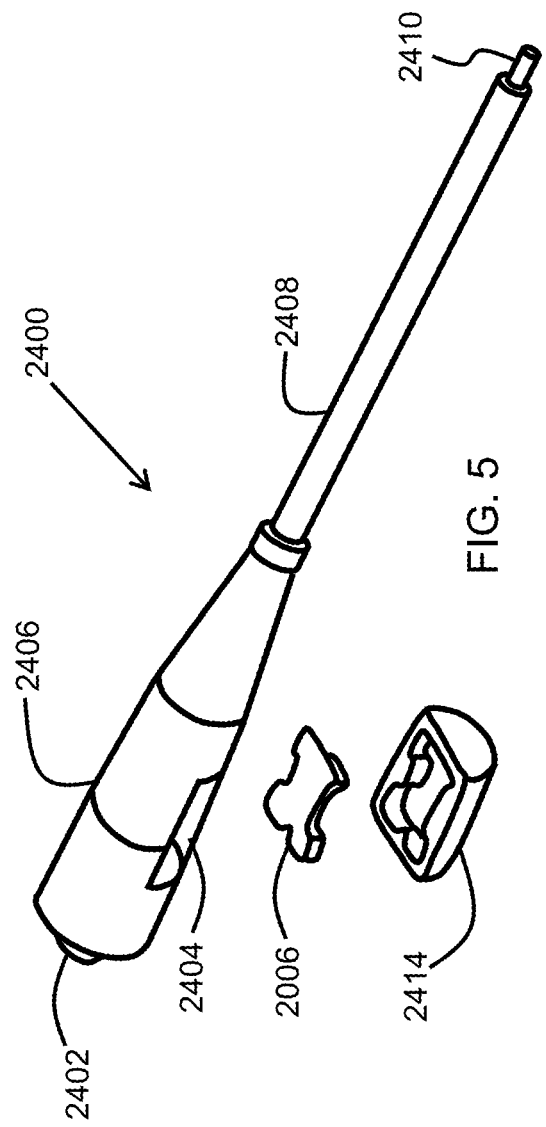

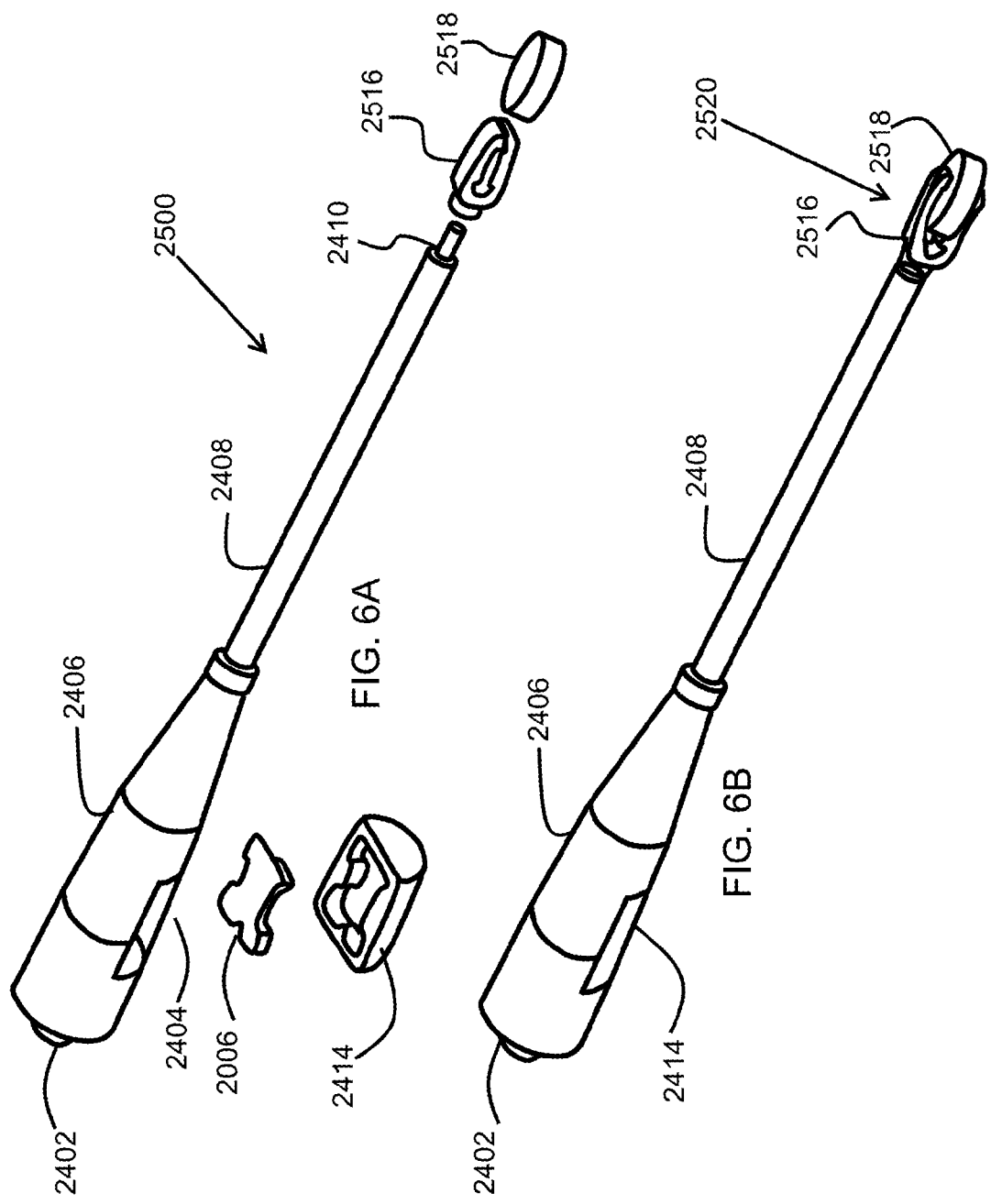

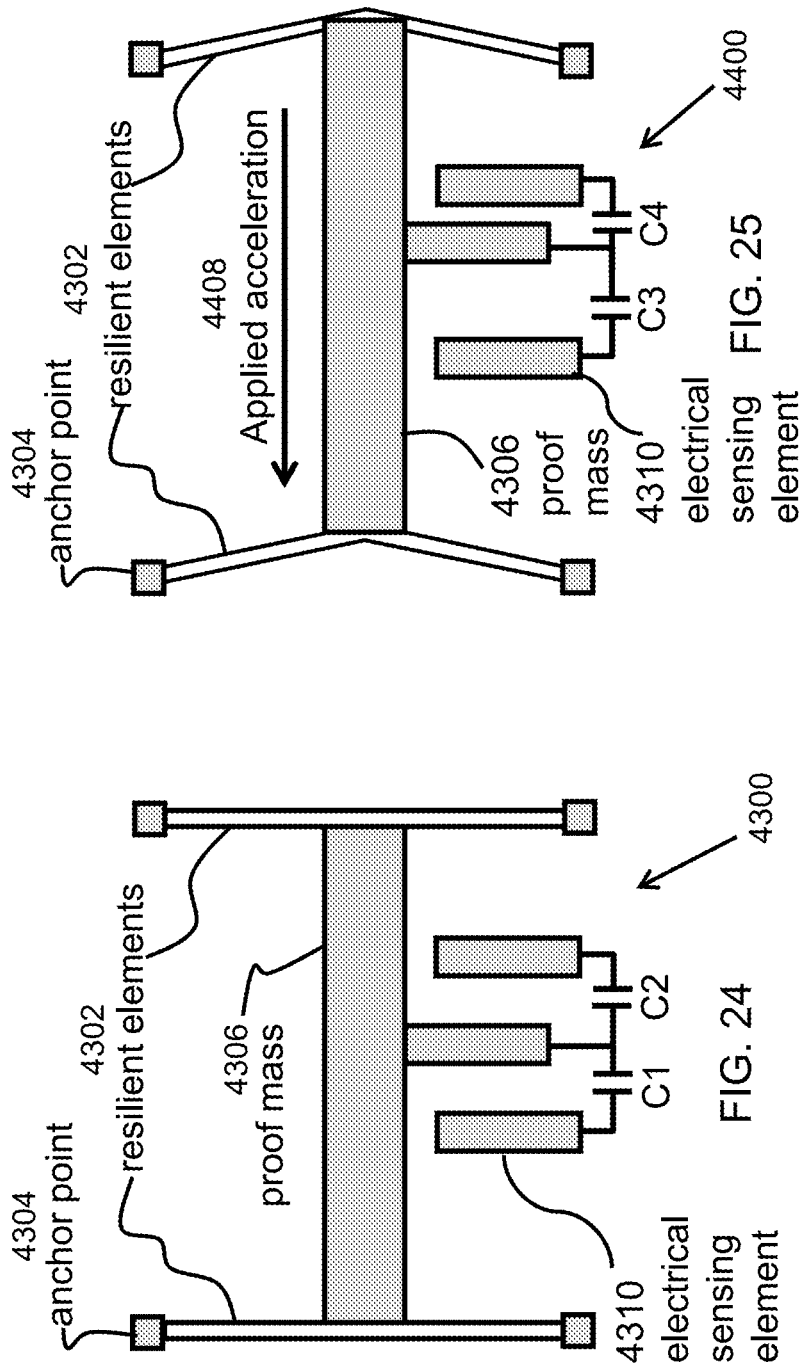

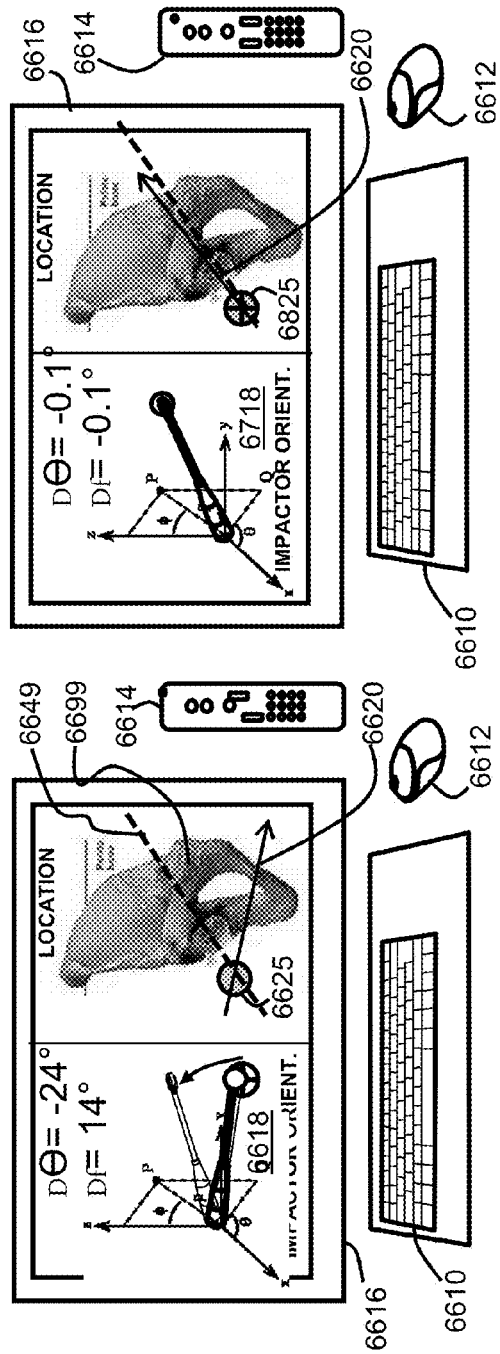
FIG. 34A
FIG. 33A
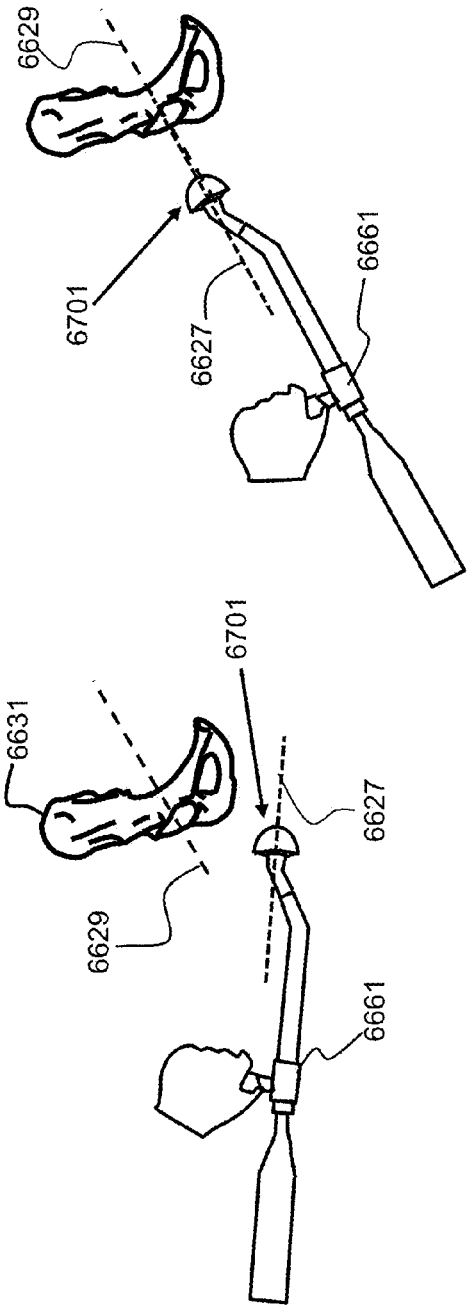

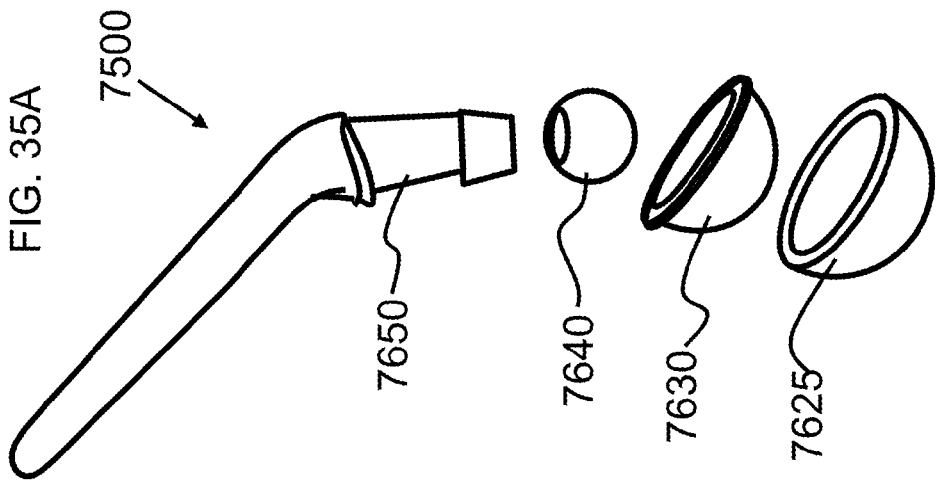
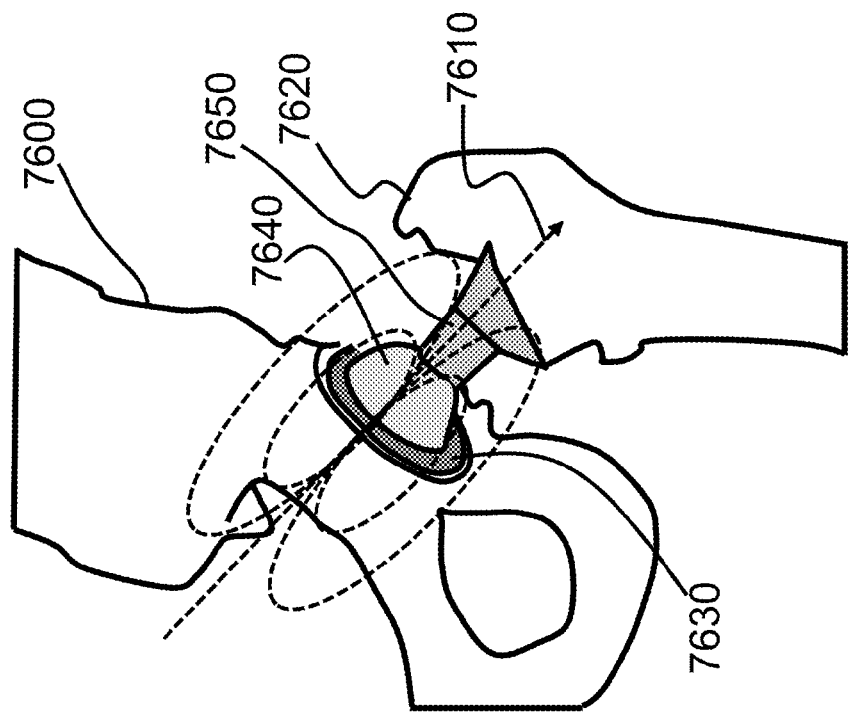

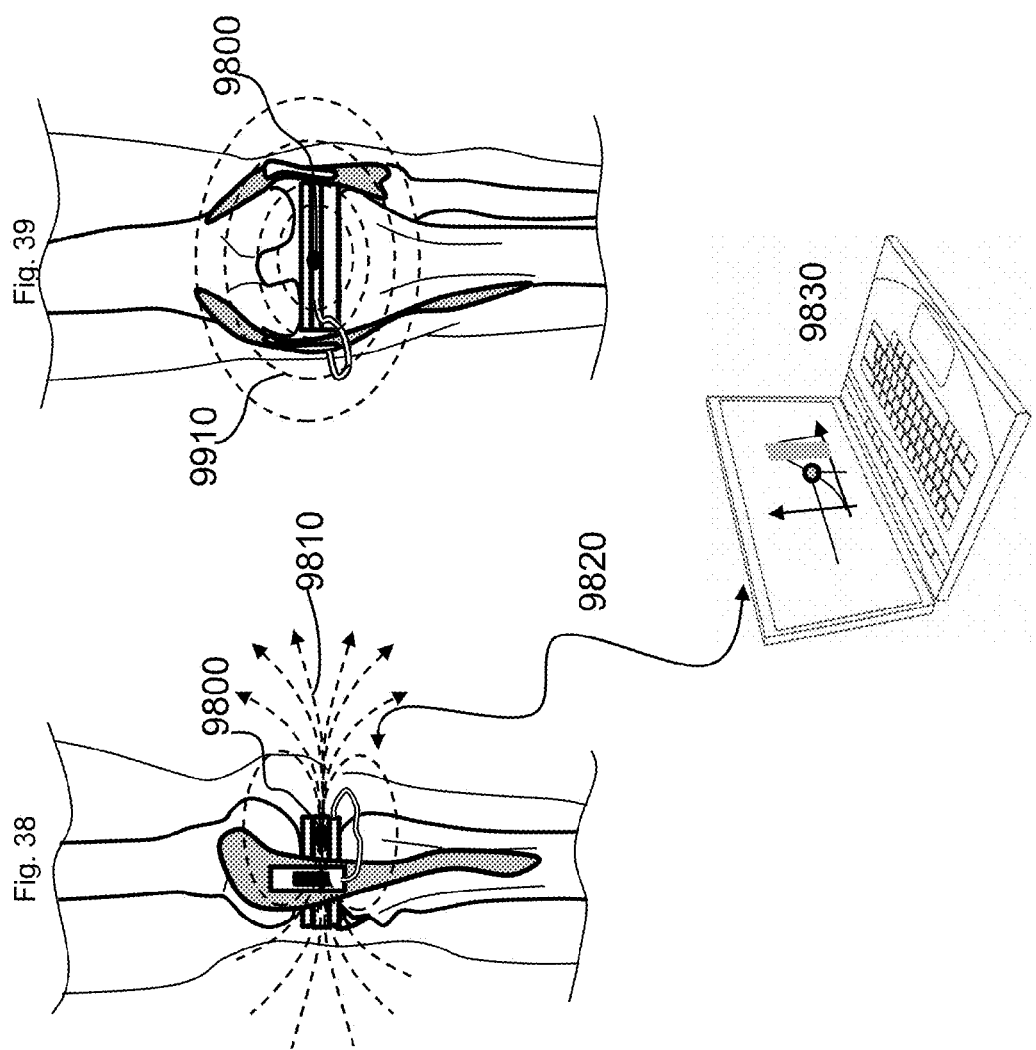

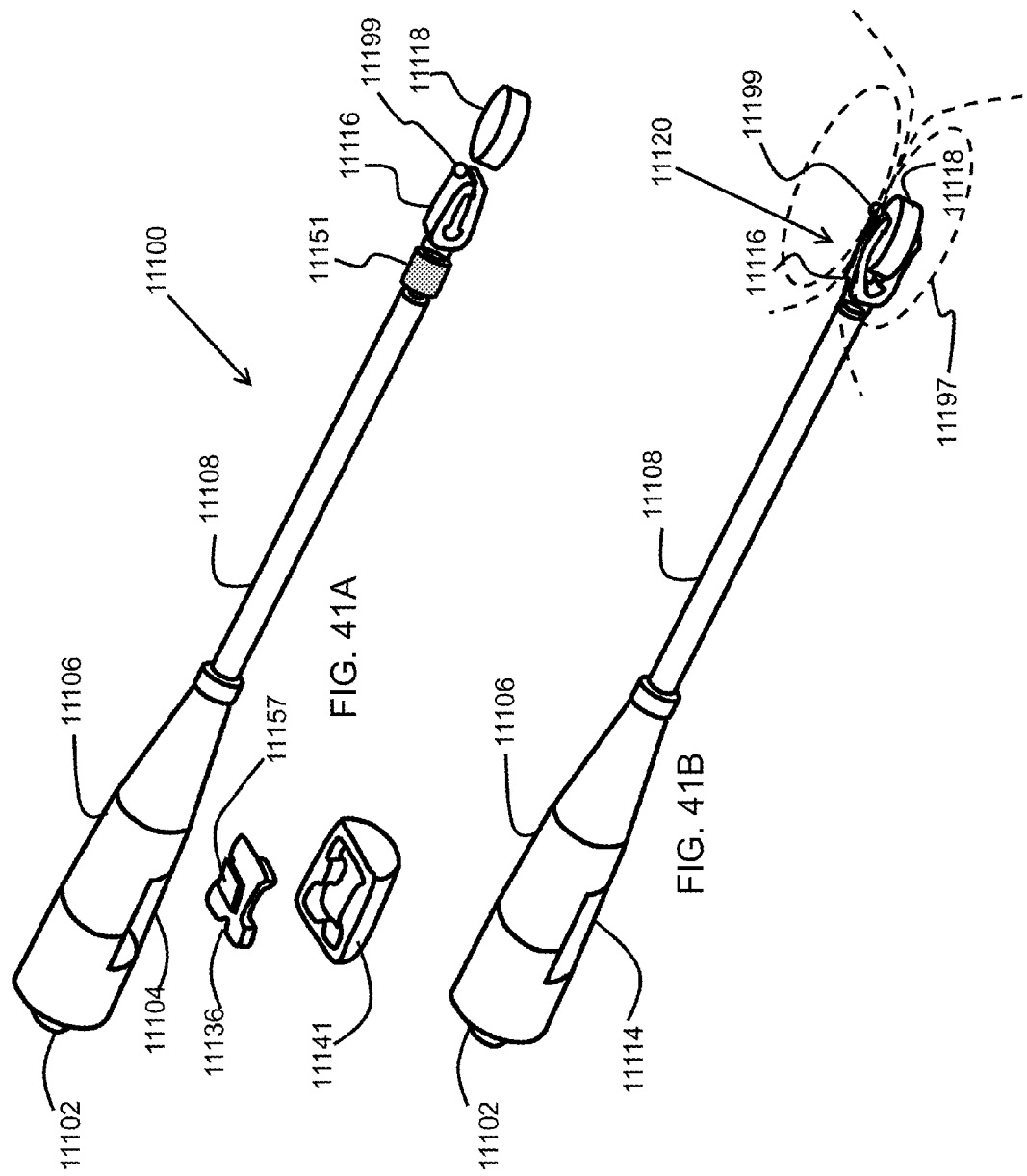

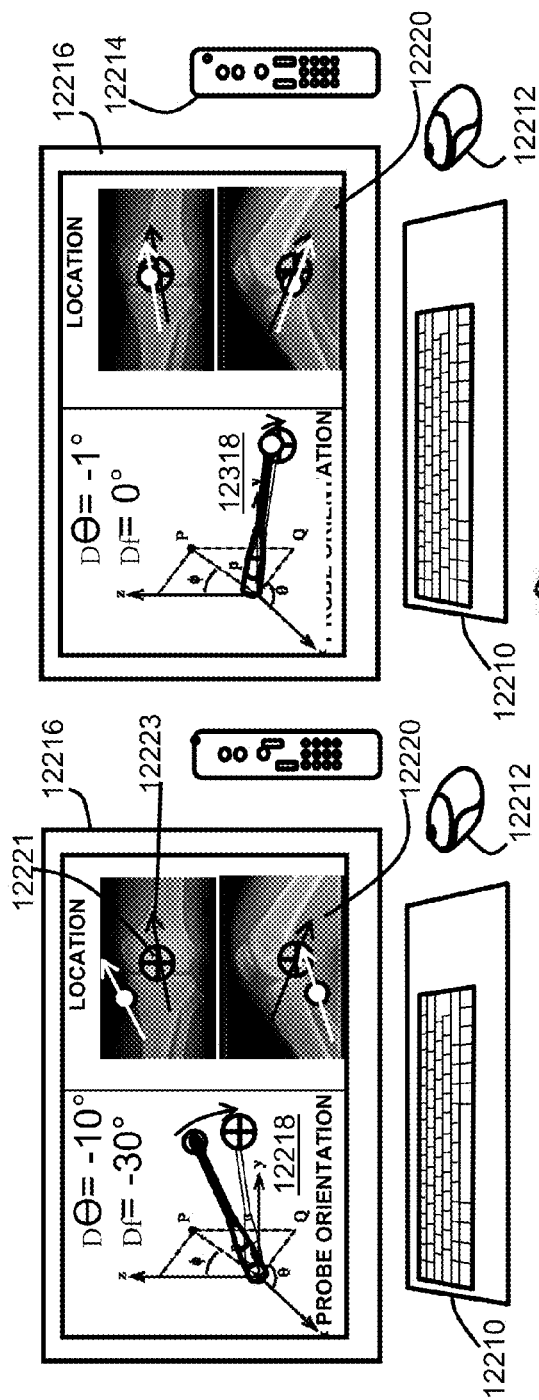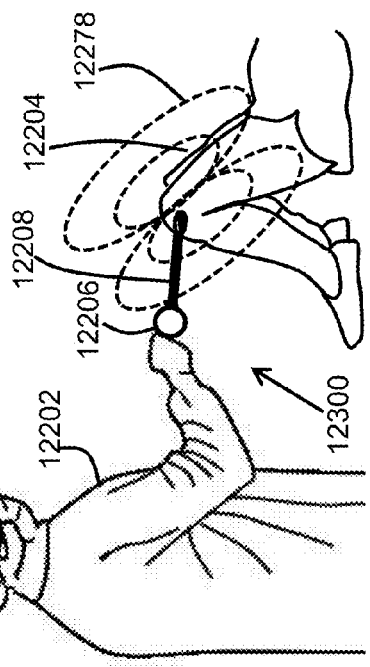
FIG. 43
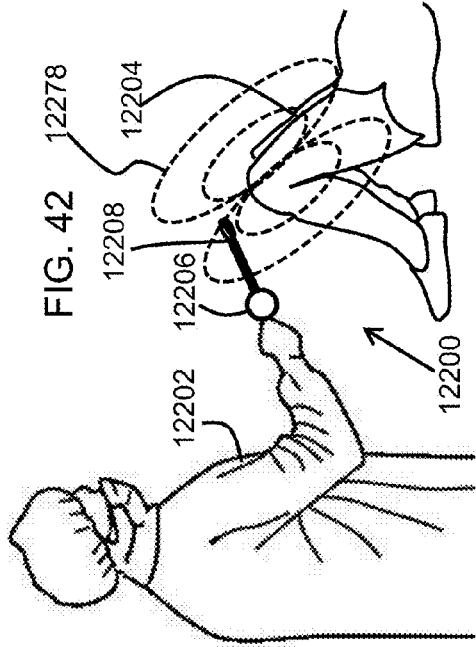
FIG. 42

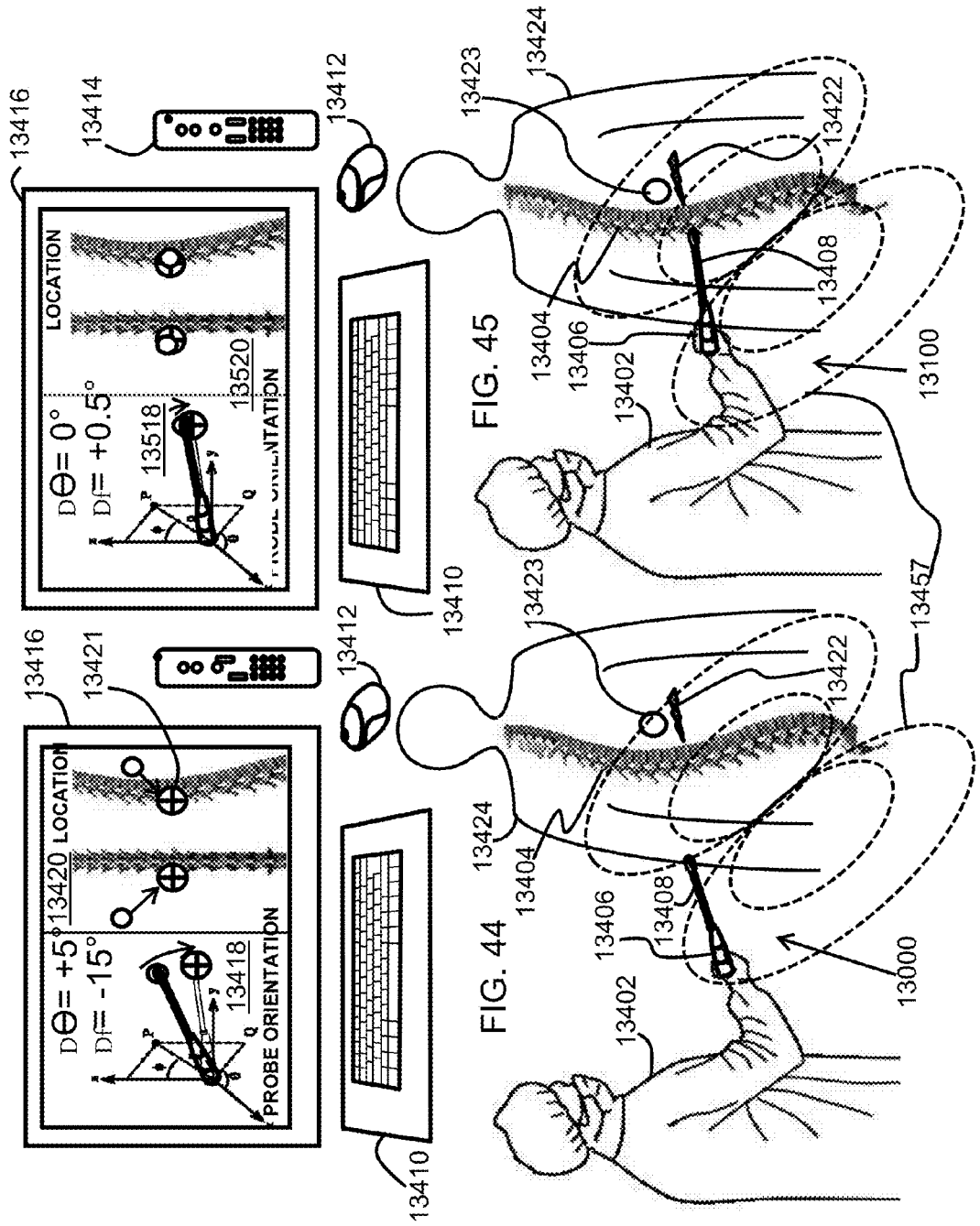

# US 9,351,782 B2

1

MEDICAL DEVICE MOTION AND ORIENTATION TRACKING SYSTEM

FIELD OF THE INVENTION

The invention relates in general to medical and surgical procedures and more particularly to guiding medical devices to precise locations on or within a patient's body.

BACKGROUND OF THE INVENTION

Precisely positioning inserts, implants, or other medical devices, prostheses, prosthetic components, or topical application of medicines or anesthetics in or on patients' bodies depends on accurately locating structural features or anomalous structures on or within a patient's body. Continual progress has been made in the advancement and use of imaging equipment to guide the positioning of inserts, implants, or other medical devices, within patients' bodies. Noninvasive methods for locating internal structures of the body include ultrasound, X-rays, CT, and MRI equipment to locate anatomical features and anomalous structures within patients' bodies. Surgeons may use this data to create a pre-operative template to guide actions during the surgery.

The use of pre-operative images to guide the precise placement and orientation of medical devices or prosthetic components during surgery may require real-time scanning of patients' bodies or the use of robotics. Much of this requires large and expensive equipment. Alternatively, physical observation by the physician or surgeon, aided by the pre-operative scans and template, may guide placement of inserts, implants, or other medical devices, or prostheses or prosthetic components within patients' bodies.

Trialing is also critical in many implant procedures. The use of trial devices or prosthetic components provides a useful guide to the selection of the prosthetic components to be included in the chronic prosthetic implant as well as confirmation of the fit and functioning of the selected prosthetic components in vivo.

Even with templating, trialing, and advanced prosthetic components, outcomes including functional efficacy, patient comfort, and longevity of the prosthesis may not always be highly predictable, especially if procedures are performed by physicians and surgeons with different levels of skill, experience, and frequency of repeating an individual procedure. This may be confirmed by various reports in the literature that suggest a positive relationship between outcomes and the numbers of procedures performed annually by individual surgeons.

BRIEF DESCRIPTION OF THE DRAWINGS

Embodiments of present invention will become more fully understood from the detailed description and the accompanying drawings, wherein:

FIG. 1 illustrates a simplified view of a physician using at least one embodiment of a motion and orientation sensing device (e.g., a surgical tracking system) with a computer display (e.g., a surgical tracking display system);

FIG. 2 illustrates a simplified view of a physician holding an instrument having an embodiment of a motion and orientation sensing device with a computer display of the instrument's location and orientation approaching a pre-specified target;

FIG. 3 illustrates a simplified view of a physician holding an instrument having an embodiment of a motion and orientation sensing device with a computer display defining the instrument's location and orientation at some distance from a pre-specified target plus a second motion and orientation sensing device pinned to a patient to track any movement of the target;

FIG. 4 illustrates a simplified view of a physician holding an instrument having an embodiment of a motion and orientation sensing device with a computer display defining the instrument's location and orientation approaching a pre-specified target while a second motion and orientation sensing device pinned to a patient tracks any movement of the target;

FIG. 5 illustrates a simplified perspective view of an example of a motion and orientation sensing device, a cover for the device;

FIG. 6A illustrates a simplified perspective view of an example of an instrument (e.g., surgical device holder) having an example motion and orientation sensing device (e.g., tracking element), a cover for the device, an interchangeable head, and an example insert or implant (e.g., surgical device) that may be held by the instrument (e.g., surgical device holder);

FIG. 6B illustrates a simplified perspective view of an assembled example of an instrument having an example motion and orientation sensing device, a cover for the device, an interchangeable head, and an example insert or implant held by the instrument;

FIG. 24 illustrates a simplified block diagram of the basic construction of a generic accelerometer at rest;

FIG. 25 illustrates a simplified block diagram of the basic construction of a generic accelerometer under acceleration;

FIG. 33A illustrates a simplified view of a physician using at least one embodiment of a motion and orientation sensing device (e.g., used to guide an impactor) with a computer display (e.g., a surgical tracking display system) with a reamer;

FIG. 34A illustrates a simplified view of a physician using at least one embodiment of a motion and orientation sensing device (e.g., used to guide an impactor) with a computer display (e.g., a surgical tracking display system) to orient the tool in a correct orientation;

FIG. 35A illustrates an example of a surgical hip implant that can be aligned via a motion and orientation sensing system in accordance with at least one exemplary embodiment;

FIG. 35B illustrates an example of an aligned hip implant using a motion and orientation sensing system in accordance with at least one exemplary embodiment;

FIG. 38 illustrates an example of an insert device implanted and aligned in a knee using an orientation sensing system in accordance with at least one exemplary embodiment;

FIG. 39 illustrates an example of an insert device implanted and aligned in a knee using an orientation sensing system in accordance with at least one exemplary embodiment;

FIGS. 41A and 41B illustrate a simplified perspective view of an example of a motion and orientation sensing device;

FIG. 42 illustrates a simplified view of a physician using at least one embodiment of a motion and orientation sensing device (e.g., used to guide a surgical tool) with a computer display (e.g., a surgical tracking display system);

FIG. 43 illustrates a simplified view of a physician using at least one embodiment of a motion and orientation sensing device (e.g., used to guide a surgical tool) with a computer display (e.g., a surgical tracking display system) to orient the surgical tool in a correct orientation;

FIG. 44 illustrates a simplified view of a physician using at least one embodiment of a motion and orientation sensing device (e.g., used to guide a surgical tool) with a computer display (e.g., a surgical tracking display system);

FIG. 45 illustrates a simplified view of a physician using at least one embodiment of a motion and orientation sensing device (e.g., used to guide a surgical tool) with a computer display (e.g., a surgical tracking display system) to orient the surgical tool in a correct orientation.

DETAILED DESCRIPTION OF EMBODIMENTS

Figure 7:
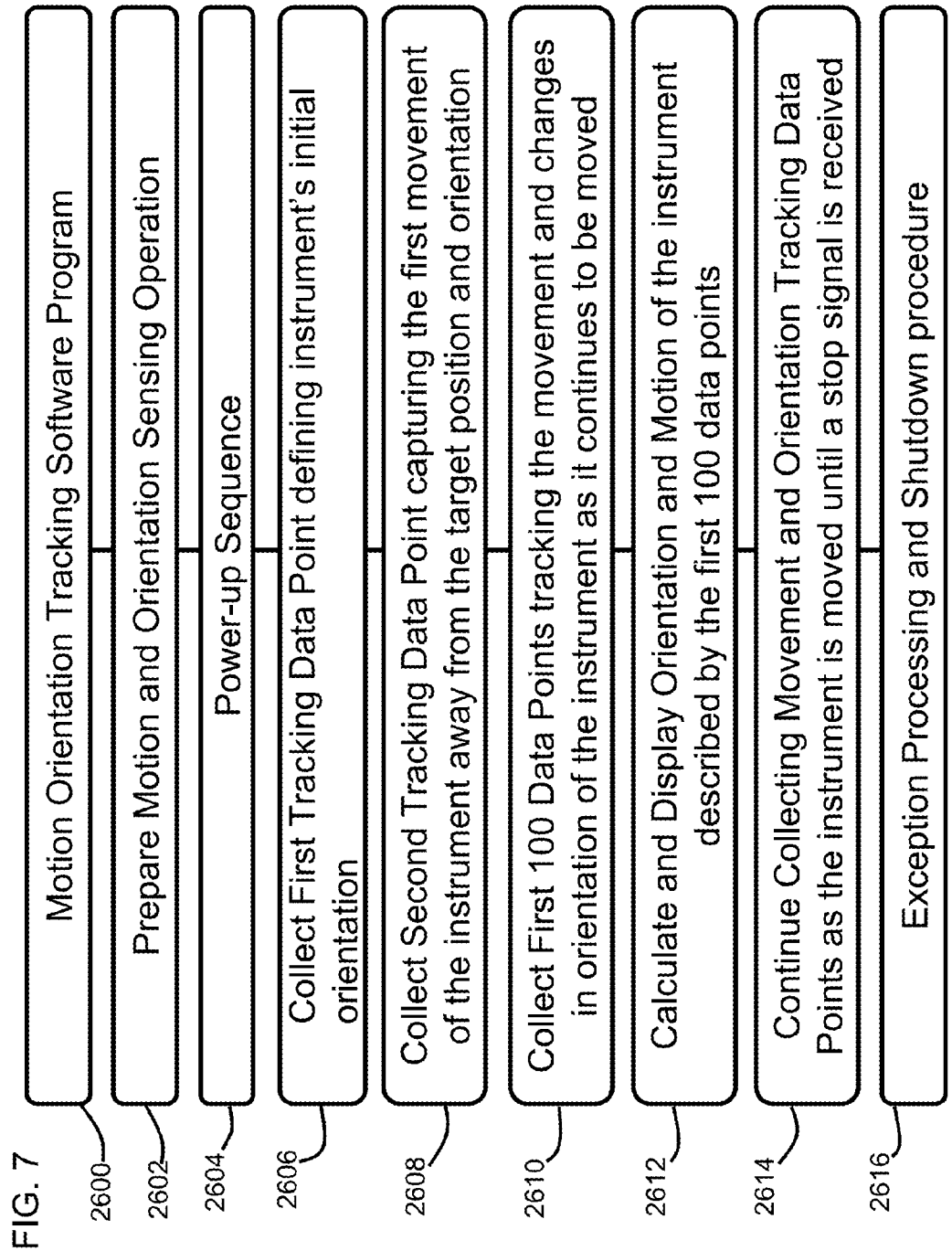
FIG. 7 illustrates a simplified example of a top-level flow chart of the steps performed by an example system having an embodiment of the motion and orientation sensing module or device and a computer system for guiding an instrument to return to its initial position.

The following description of embodiment(s) is merely illustrative in nature and is in no way intended to limit the invention, its application, or uses.

At least one embodiment is directed to a portable or handheld, wired or wireless dual tri-axial accelerometer device that facilitates replacement of a surgical instrument to a desired location, such an embodiment enables a cost effective alternative for performing many medical and surgical procedures. At least one embodiment is directed to a surgical tracking system that emits no harmful radiation, is light weight, requires minimal training, is inexpensive, flexible enough to support multiple procedures, can track real time motion of surgical devices and patients, and can include other biometric data sets.

Utilizing an accelerometer or other methods of the embodiments for surgical instrument placement reduces the invasiveness of many medical and surgical procedures without compromising the precision of locating probes, instruments, instruments, inserts, implants, and other medical devices with respect to anomalous structures on or within patients' bodies, boney landmarks within patients' bodies, structural features on or within patients' bodies, or centers of rotation within patients' joints. Data gathered from the location devices in embodiments can be readily integrated into electronic health record systems and databases to facilitate sharing of patients' medical data among appropriate physicians and surgeons. Reducing invasiveness, as well as improving access to medical records data, improves patient safety and reduces overall healthcare costs to the patient, as well as to society.

At least one embodiment is directed to guiding probes, instruments, or similar apparatus to precise locations on or within a patient's body, as well as precisely positioning inserts, implants, or other medical devices, or topical application of medicines or anesthetics in or on patients' bodies.

Utilizing an accelerometer or other methods of the embodiments for surgical instrument placement enables highly effective trialing procedures with the placement and orientation of chronic prosthetic components precisely duplicating the position and orientation of trial components or devices. Therefore the intra-operative results demonstrated with the trial component are accurate predictors of the performance of the chronic prosthetic implant.

At least one embodiment is directed to a portable, handheld device for accurately guiding probes, instruments, instruments, to precise locations on or within a patient's body, as well as precisely positioning inserts, implants, other medical devices, or prostheses or prosthetic components within patients' bodies, or topical applications of medicines or anesthetics in or on patients' bodies. Highly precise and repeatable positioning of medical instruments and devices as well as topical medicines, can improve the efficacy of medical and surgical procedures, improve patient comfort and safety, and reduce overall healthcare costs to the patient and to society.

Herein the surgical tracking system is also referred to as a motion and orientation sensing device.

For simplicity and clarity of the illustration(s), elements in the figures are not necessarily to scale, are only schematic and are non-limiting, and the same reference numbers in different figures denote the same elements, unless stated otherwise. Additionally, descriptions and details of well-known steps and elements are omitted for simplicity of the description. Notice that once an item is defined in one figure, it may not be discussed or further defined in the following figures.

It will be appreciated by those skilled in the art that the words "during", "while", and "when" as used herein relating to circuit operation are not exact terms that mean an action takes place instantly upon an initiating action but that there may be some small but reasonable delay, such as a propagation delay, between the reaction that is initiated by the initial action. Additionally, the term "while" means that a certain action occurs at least within some portion of duration of the initiating action. The use of the word "approximately" or "substantially" means that a value of an element has a parameter that is expected to be close to a stated value or position. However, as is well known in the art there are always minor variances that prevent the values or positions from being exactly as stated.

The terms "first", "second", "third" and the like in the Claims or/and in the Detailed Description are used for distinguishing between similar elements and not necessarily for describing a sequence, either temporally, spatially, in ranking or in any other manner. It is to be understood that the terms so used are interchangeable under appropriate circumstances and that the embodiments described herein are capable of operation in other sequences than described or illustrated herein.

Processes, techniques, apparatus, and materials as known by one of ordinary skill in the art may not be discussed in detail but are intended to be part of the enabling description where appropriate. For example specific methods of attaching a surgical device onto the surgical device holder, however one of ordinary skill would be able, without undo experimentation, to establish the steps using the enabling disclosure herein.

At least one embodiment is directed to a portable or handheld, wired or wireless device that enables a cost effective alternative for guiding the positioning of inserts, implants, or other medical devices, prosthetic components, or topical application of medicines or anesthetics in or on patients' bodies. With the aid of embodiments these medical and surgical procedures and can be expected to obtain highly reproducible results. At least one embodiment reduces invasiveness of many medical and surgical procedures without compromising the precision of locating probes, instruments, instruments, inserts, implants, prostheses or prosthetic components and other medical devices with respect to anomalous structures on or within patients' bodies, structural features on or within patients' bodies, or boney landmarks. Data gathered during a medical procedure are readily integrated into electronic health record systems and databases facilitating the sharing of patients' test results among appropriate physicians and surgeons. Reducing invasiveness, as well as improving access to medical records data, improves patient safety and comfort as well as reduces overall healthcare costs to the individual and to society.

The terms precision and resolution can be used herein to specifically have the standard definitions. Precision will connate the variation from exactness. Resolution will have the customary definition of the smallest measurable interval. The orientation of the x, y, z axes of rectangular Cartesian coordinates is assumed to be such that the x and y axes define a plane at a given location, and the z axis is normal to the x-y plane. The axes of rotations about the Cartesian axes of the device are defined as yaw, pitch and roll. With the orientation of the Cartesian coordinates defined in this paragraph, the yaw axis of rotation is the z axis through body of the device. Pitch changes the orientation of a longitudinal axis of the device. Roll is rotation about the longitudinal axis of the device.

The orientation of the x, y, z axes of rectangular Cartesian coordinates is selected to facilitate graphical display on computer screens having the orientation that the user will be able to relate to most easily. Therefore the image of the device moves upward on the computer display whenever the device itself moves upward for example away from the surface of the earth. The same applies to movements to the left or right.

The terms 'motion sensing' and 'tilt sensing' and 'orientation' are also intended to have specific meaning. 'Motion sensing' indicates the detection of movement of a body that exceeds a specified threshold in one or more coordinate axes, for example the specific threshold in one or more Cartesian axes in terms of both static and dynamic acceleration. 'Heading' is defined as the orientation of longitudinal axis of the motion of the motion and orientation sensing module or device and movement in a direction. 'Tilt' is defined as the orientation of a body with respect to a zenith. Tilt sensing' indicates the measurement of acceleration attributable to gravity in one or more axes. 'Orientation' includes yaw as well as 'tilt.' Yaw is not readily quantified by accelerometers whenever the center of rotation coincides with the center of the proof mass within an accelerometer. Detection of this rotation may require two or more accelerometers to assure that at least one accelerometer is moved enough to reliably sense motion that accompanies yaw. Note that although accelerometers are provided as enabling examples n the description of embodiments, any tracking device (e.g., a GPS chip, acoustical ranging, magnetometer, gyroscope) can be used within the scope of the embodiments described.

At least one embodiment is directed to surgical tracking system which can include a motion and orientation sensing module (e.g. tracking element) or device that can be embedded in, affixed on, or attached to surgical device holder (e.g., a probe, tool, instrument, alignment jigs or cutting blocks, or similar apparatus) and used to accurately guide surgical devices (e.g., medical instruments and equipment) to a specified location and orientation in space with high precision. It can also be used to guide positioning of other surgical devices such as inserts, implants, or other medical devices, prostheses or prosthetic components, or even topical application of medicines or anesthetics in or on patients' bodies. A hermetic, wireless motion and orientation sensing device, having one or more accelerometers, signal processing, telemetry, and control circuitry, nonvolatile memory, and energy storage, harvesting, or receiving components within an enclosure, shell, or body having one or more switches or touch sensitive surfaces, can be used during these medical or surgical procedures. The target location and orientation can be defined by a previous or initial location and orientation of a probe, instrument, or instrument having a motion and orientation sensing device, or by data from imaging systems or positioning guides, or by manual or robotic examination and identification of anatomical structures or landmarks, anomalous structures on or within the body, by extrapolation or interpolation from those landmarks, or anomalous structures on or within a patient's body. This can include surface contact or transcutaneous penetration by a probe, instrument, or instrument having a motion and orientation sensing device attached, affixed, embedded, or integrated at a fixed position with respect to its leading edge or active face.

The movement of a probe, tool, instrument, or alignment jigs or cutting blocks, or similar apparatus having a motion and orientation sensing module or device integrated or attached to, embedded into, affixed onto, or integrated within to it can be locally or remotely controlled to accurately orient and position the tip of the active portion of the controlled equipment at the specified point or target in space with high precision. For example within 1 mm and 1 degree for a path length of 5 m or less. This can facilitate the performance of medical or surgical procedures with high levels of consistency and repeatability, as well as capturing position-related data in real time for preservation in electronic health records.

Other functions and sensing capabilities can be readily integrated into a motion and orientation sensing module or device to augment its functional and sensing capabilities and provide additional real-time data for positioning and orienting probes, instruments, instruments, equipment, and medical devices, implants, prostheses or prosthetic components, as well as gathering other forms of pertinent additional data. Additional data acquisition capabilities can include sensing pressure, force, temperature, detection of many forms of radiation including electromagnetic, electric, or magnetic fields, light, and infrared, as well as sensing sound and ultrasound. Additional sensing capabilities and data captured in real time can augment electronic health records, as well as be useful in supporting refinement of the consistency and repeatability of medical and surgical procedures. For example an additional tracking data set (e.g., position, velocity, acceleration) of the surgical device holder can be acquired from systems (e.g., acoustical ranging, infrared pattern disruption, laser reflection) that can be fed into the surgical tracking display system and used to improve the position and orientation of the surgical device holder.

Accelerometer technology is used in many applications, although few may have higher accuracy and precision requirements than highly exacting medical procedures such as biopsies, orthopedic surgeries, or comparable procedures require. Few applications have greater reliability and safety requirements than medical applications. In fact, some electronic component manufacturers included disclaimers that their products are not qualified for medical applications.

Accelerometers are effective sensors for acceleration as well as tilt with respect to the center of the earth. In the at least one embodiment a wireless motion and orientation sensing module or device, having an accelerometer or accelerometers in addition to other electronic components and electrical circuitry, is used to detect, track, quantize, and transmit motion and changes in orientation in real time. These data can be graphically displayed in real time to aid in guiding movement with respect to a target location and orientation.

Acceleration is the second derivative of distance traveled. Therefore the acceleration data can be integrated to estimate velocity and velocity can be integrated to estimate distance traveled. These operations are readily accomplished with software. Distance traveled, in all three dimensions, can be tracked from a known starting point. With each incremental movement of a probe, tool, instrument, alignment jigs or cutting blocks, similar apparatus, or a physician's or caregiver's hand, or robotic arm and gripper, the output of these calculations can be used to estimate the remaining distance to the target. This distance can be displayed in real time on a computer driven video display screen. This feedback loop can be used to accurately guide the probe, tool, instrument, alignment jigs or cutting blocks, or probes, instruments, instruments, or similar apparatus held in a physician's or caregiver's hand, or implants, prostheses or prosthetic components, to the target with high level of precision, including subcutaneous targets the physician or caregiver may not be able to view directly.

Error propagates with increased positional derivations. For example when obtaining the positional value from a measured acceleration, the error of the acceleration must be combined with the error in the time, and the error of the derived initial velocity, which results in a larger error in the position than in the acceleration. One method of mitigating propagating errors is to measure position, velocity, and orientation directly and combine the data with their associated errors into an algorithm (e.g., Kalman Filter) combining the data to provide enhanced tracking of the surgical device holder. For example current inertial navigation system (INS) chips (e.g., VN-100™) can provide accuracies to <2 degrees of heading with a resolution of <0.05 degrees; a pitch and roll accuracy to <0.5 degrees at a resolution to <0.05 degrees; an angular rate bias stability (for heading, pitch, roll) to <+/−0.06 degree/sec; and an acceleration bias stability to <3 mg (milli-acceleration of gravities). Current INS chips employ the use of microcircuit accelerometers, angular rate gyros and magnetometers as input to algorithms (e.g. Kalman Filtering) to enhance the accuracy of the provided position and orientation data. Note also that the use of multiple accelerometers provides an overdetermined system of equations that can be used to improve the position and orientation determination.

Orientation of the tip of the probe, tool, instrument, or alignment jigs or cutting blocks, or similar apparatus, or implants, prostheses or prosthetic components can be as critical as their location. Data defining the tilt with respect to gravity is also available from accelerometers. This data (e.g., tracking data) can be incorporated into the real-time display (e.g., in a surgical tracking display system) to illustrate the orientation of the surgical device (e.g., probe, tool, instrument, alignment jigs or cutting blocks, or similar apparatus, or probes, instruments, instruments or similar apparatuses) held in a physician's or caregiver's hand, or used to automatically guide a robotic arm and gripper, in all three axes simultaneously. This feedback loop can be used to guide the orientation of the probe, tool, instrument, alignment jigs or cutting blocks, or implants, prostheses or prosthetic components to the target. This can also include subcutaneous targets the physician or caregiver may not be able to view directly.

The third vector of orientation is the yaw, or heading, of the probe, tool, instrument, or similar apparatus. The motion and orientation sensing module or device having two tri-axial accelerometers quantifies the yaw of an associated probe, tool, instrument, or similar apparatus. Yaw is measured and tracked by collecting acceleration data from an accelerometer positioned at each end of the longitudinal axis of the enclosure of the motion and orientation sensing module or device. The forward tri-axial accelerometer defines the tilt of the probe, tool, instrument, or similar apparatus with respect to the horizon. The algebraic sum of the acceleration in all of the three Cartesian axes of the forward tri-axial accelerometer determines the distance between the leading edge, or active face, of the probe, tool, instrument, or similar apparatus and the target. The algebraic sum of the acceleration of the tri-axial accelerometer positioned at the trailing edge of the motion and orientation sensing module or device determines the position of the rear of the probe, tool, instrument, or similar apparatus with respect to the distal tip of the probe, tool, instrument, or similar apparatus. From this information the yaw of the probe, tool, instrument, or similar apparatus is calculated. Note that additional embodiments are not limited to determining the position of the rear of the probe as other locations on the probe can be determined. The combination of location and orientation data calculated from acceleration and tilt data produced by the two tri-axial accelerometers enables a user of the motion and orientation sensing module or device to accurately locate and orient a probe, tool, instrument, or similar apparatus precisely at its target location and orientation with no discrepancies in pitch, roll, or yaw.

For example, one can sample the dynamic and static acceleration readings from each accelerometer within both triaxial accelerometer ICs with a constant sample rate. These values can then be captured and recorded in an array of acceleration values. A rectangular approximation of the integral of the acceleration can be used to compute the average velocity of each sample period. Additional approaches can also used, for example a 3rd or 4th order approximation method. The direction of acceleration along one or more axes can reverse during some sample periods, thus the use of algebraic differences in acceleration during each sample period. Once the algebraic average of the velocity during each period is estimated, a rectangular approximation of the integral of the average of velocity can be used to estimate the change in location of the device. These changes in location are algebraically summed as well and when the net change in location is zero within estimated error, the device has returned to its initial location. When both triaxial accelerometers have returned to their initial locations, the heading of the device corresponds to its initial orientation. Whenever the algebraic sum of the changes in tilt of the two triaxial accelerometers in the X-Z and Y-Z planes is zero the orientation of the device in those two planes has returned to their initial values as well.

At least one embodiment uses multiple accelerometers, and a non-limiting example using two accelerometers can be discussed. Motion and orientation sensing modules and devices having two accelerometers are not only capable of providing more accurate yaw data, but two accelerometers also provide a level of redundancy that aids in the confirmation that the instrument is guided accurately to the target position and orientation. If this cannot be achieved to the required level of precision for both accelerometers the tracking procedure may have been compromised and the user can be alerted to the possibility of an exception condition that needs to be addressed.

The precision of the final placement and orientation of the probe, tool, instrument, alignment jigs or cutting blocks, or similar apparatus, as well as implants, prostheses or prosthetic components, depends on three key factors: the precision of the location and orientation of the starting point; the accuracy and resolution of the acceleration data used to guide the movement of the sensing module or device; and the accuracy and resolution of the tilt data used to guide the movement of sensing module or device.

The starting location and orientation can be specified in many ways including physical examination, boney landmarks, imaging, and other methods of identifying anatomical or anomalous features or structures on or within a patient's body. These approaches require an accurate estimate of the change in orientation and distance between the starting point and the final location and orientation for the probe, tool, instrument, or similar apparatus, or implants, prostheses or prosthetic components, at the target location.

A second alternative for estimating the location and orientation of the target location and orientation uses the motion and orientation sensing device to identify the center of rotation or alignment of a symptomatic limb with respect to other joints or portions of the limb. The motion and orientation sensing device is then used to track the movement and orientation of the probe, instrument, alignment jigs or cutting blocks, instrument, or similar apparatus, or implants, prostheses or prosthetic components to guide them to the designated location and orientation.

A third approach to eliminating errors associated with estimating the distance and change in orientation is to begin tracking the movement of the probe, instrument, or instrument having a motion and orientation sensing module or device precisely at the target location and orientation. In this case the objective is to return the probe or instrument to exactly the same location and orientation it had when the tracking procedure was initiated. Starting and ending at the target location and orientation may not be as limiting as it might first appear. This procedure is applicable to many medical procedures wherein something is removed and replaced, or removed, modified, and returned to its original position and orientation. This includes many forms of trialing. It also applies to any procedure wherein the same site on or within a patient's body is accessed two or more times during any medical or surgical procedure.

Regardless of which method is used to establish the starting location and orientation, as well as defining the distance to the target location and its orientation, the sensing module or device can be used to track each incremental movement and change in orientation of probes, instruments, instruments, or similar apparatus. Each of these movements can be captured accurately, and the location and orientation of the sensing module or device precisely updated in real time.

An additional variable arises whenever the target location may move during the tracking procedure. This can be caused by the patient's movement, including movement as small as taking a breath. A marker motion and orientation sensing module or device can be attached to the patient's body in a location that is fixed with respect to the target location. Also, the orientation of the marker device can be fixed with respect to the orientation of the target. When these conditions are met it is a straightforward process to update the target location and orientation whenever it is moved by applying the same software routines that update changes in the location and orientation of the tracking motion and orientation module or device. The data from the tracking device may readily be adjusted to display the correct distance between it and the target, as well as its orientation relative to the orientation of the target, in real time.

The accuracy and resolution of the acceleration sensing elements is critical to achieving the accuracy and resolution required to guide the sensing and tilt module or device. This includes both the accuracy and resolution of the sensing of acceleration as well as the tilt sensitivity of the acceleration sensors. These requirements are driven by several attributes of intentional human motion in the areas of the torso, arm, wrist, and hand. These determinative factors include the range of speed of intentional human arm and hand movements, the dexterity or fine motor control of the human arm, wrist, and hand movements, and the maximum frequency of intentional human arm and hand movements. The required tilt sensitivity of an accelerometer is also determined by the parameters of human arm, wrist, and hand movements.

The maximum speed and frequency of human arm movements determines the required measurement range of each accelerometer within a motion and orientation detection module or device. Small hand motions may include acceleration levels up to 3 g. Vigorous motions may include acceleration levels on the order of 4 g. Therefore an 8 g accelerometer will assure an adequate range of detection, even for a user with extremely high hand speed. An 8 g accelerometer may also enable the capture and analysis of unexpected events such as dropping the probe, tool, instrument, or similar apparatus, or accidentally striking something with it.

The maximum speed and frequency of human arm movements is also a determinative factor in the selection of the range and sample rate of the accelerometer or accelerometers and other circuitry within the motion and orientation detection module or device. Obviously the speed of human arm movements varies widely depending on the individual, as well as speed with which a specific activity may be performed.

But the level of resolution required of the accelerometer or accelerometers is independent of these differences. The level of precision required in medical procedures is the same regardless of how rapidly various individual movements may be performed by individual practitioners. Therefore, although the measurement range of the accelerometer or accelerometers can be set to the level required to capture the most rapid applicable intentional human movements, this does not change the required level of resolution.

For many medical procedures the level of precision may be as small as half a millimeter. Therefore, a resolution of one-quarter millimeter, or less, may be required to assure this level of precision. The tracking element (e.g., INS chip(s), accelerometer or accelerometers) and the circuitry used for quantization, processing, and telemetry of position, velocity, acceleration and tilt data, must have this level of resolution, when needed, to guide probes, instruments, instruments, alignment jigs or cutting blocks, or similar apparatuses, or probes, instruments, or instruments held in a physician's or caregiver's hand, or in a robotic arm and gripper, to the target with this level of precision regardless of the measurement range of the accelerometer or accelerometers.

Intentional human movement tends to be limited to a maximum frequency in the range of 10 to 12 Hz. A bandwidth of 40-60 Hz is adequate to capture the detail of this range of motions.

A delicate medical or surgical procedure is obviously not performed at the maximum speed a human arm or hand can move back and forth. A conservative estimate for the maximum frequency of body motions in these cases may be in the 5 Hz range. Sampling the output of the tracking elements (e.g., accelerometer or accelerometers, INS chip(s)) every 10 milliseconds, or at a 100 Hz rate, will capture an average of 20 points on a single cycle of a 5 Hz signal. This provides an adequate digitized virtual image of movements of this frequency or less.

In the discussion that follows, accelerometers will be used as a non-limiting example of a portion of a tracking element used to obtain positional and orientation data. At the non-limiting example of a sample rate, discussed above (10 Hz), the effective least significant bit output by the accelerometer or accelerometers, as well as digitized by the ADC circuitry and transmitted by the telemetry circuitry, must provide adequate resolution to support a precision level required for the particular use, for example for certain surgical procedures of one-half mm or less. Conservative estimates of the required resolution of intentional motion during a medical procedure may include changes in location and orientation as small as a 0.1 millimeter. Intentional motion of movements this precise may also be as slow as 1 mm a second, especially when the probe, tool, instrument, alignment jigs or cutting blocks, or probes, instruments, or instruments held in a physician's or caregiver's hand are closing on the target.

When needed, the accelerometer or accelerometers, and the circuitry used for quantization, processing, and telemetry of acceleration and tilt data, must have adequate resolution to guide probes, instruments, instruments, alignment jigs or cutting blocks, or similar apparatuses, or implants or prosthetic components to the target with this required level of precision.

Although the following discusses specific examples of the bit requirement of data, other embodiments can use different bit levels depending upon the system requirements. The required number of bits may be estimated based on the following assumptions: an 8 g accelerometer is a conservative range appropriate for capturing human motion during medical and surgical procedures, persons with the high levels of dexterity required for medical and surgical procedures are capable of precise movements of their arm, wrist, and hand with a precision of less than ±0.5 millimeter, these persons also have steady control of extraordinarily slow movements of their arm, and wrist, and hand to as slow as 1 mm a second, thus the levels of acceleration associated with slow movement of this level can be detected. Thus, the quantification of movements on this order can be represented by three or more bits. This provides a resolution of approximately one tenth of the minimum level of acceleration.

The results of the following analysis indicate that the resulting technical requirements are realistic and conservative, note that basing designs on highly conservative assumptions assures headroom to support future advances in the gold standard of treatment for applicable medical and surgical procedures.

Applying the standard equations:

micro g=9.8066 micrometer/s2;

Velocity in μm/s=time×Acceleration in μm/s2;

1000 μm/s=1 s (A μm/s2);

Acceleration=1000 μm/s2=102 micro g;

Based on these equations and assumptions, reliable quantification of the minimum level of acceleration for exacting medical and surgical procedures with an 8 g accelerometer requires a minimum (Effective Number Of Bits) ENOB of between 16 to 17 bits, or approximately 16.5 binary bits of resolution. The term 'effective number of bits,' is a figure of merit that is calculated from signal-to-noise plus distortion (SINAD). A resolution of approximately one tenth of the minimum level of acceleration is conservatively adequate. To have three or more bits of additional resolution at the minimum level of acceleration requires an effective number of bits of 20. This is adequate for tracking intentional movement of the torso, arm, wrist, and hand motion defined during exacting medical and surgical procedures.

The assumptions about intentional human movements may also be used as a basis for defining the required tilt sensitivity for guiding the movement of the motion and orientation sensing module or device. A conservative assumption of tilt sensitivity requirements of an accelerometer or accelerometers can be calculated by once again assuming a precision orientation requirement of ±0.1 millimeters with respect to the central ±0.5 mm of the target orientation. The required precision of the least significant bit is approximately 980.66 micrometer/s2. For an 8 g accelerometer this requires in an ENOB greater 17.5 to achieve a resolution of one-tenth of the minimum required resolution. This equivalent number of bits is less than the resolution required for motion detection. Therefore circuitry that adequately detects, quantizes, and processes motion data will be more than adequate for tilt data as well.

A conservative assumption of sensitivity to yaw achieved by a pair of triaxial accelerometers can be calculated based on the previous assumption of the precision of each accelerometer. This assumption may be restated that each of the two triaxial accelerometers achieves a precision of ±0.1 millimeters when used to calculate positional location, or slightly greater than ±4 mils. Applying this assumption, an example device having two triaxial accelerometer die separated by one inch, center to center, along the longitudinal axis of the motion and orientation sensing module or device can conservatively achieve a precision in detection and quantization of yaw of 13.75 arcminutes. Therefore these assumptions on the precision of intentional human movements produce consistent results for detection and quantization of yaw. Since the precision of measurements of relative distance and orientation is likely to be higher than absolute measurements, acceleration sensing elements and circuitry that adequately detects, quantizes, and processes movement data will be more than adequate for yaw data as well.

This estimated requirement of an ENOB of 20 is based on multiple worst case assumptions. These assumptions include the worst case maximum and minimum rates of acceleration, the worst case maximum and minimum speeds of movement, and the worst case level of required precision for both linear movement and orientation. Obviously this is intended to maximize patient safety as well as contribute to the achievement of highly effective outcomes of medical and surgical procedures.

Twenty bits of effective resolution is approximately one part per million (ppm). Accuracy in the ppm range requires high precision circuitry and components. The requirements of the design, production, and test of precision circuitry of this level of precision are well understood and appropriate approaches are well developed in the electronics industry. This level of resolution may help contribute to the advancement of the precision, repeatability, and documentation of current manual approaches to controlling the movement and orientation of probes, instruments, instruments, alignment jigs or cutting blocks, or similar apparatus, or implants, prostheses or prosthetic components, in medical procedures.

The model of human arm movement outlined here is also applicable to robotic arm movement as well. These movements, especially in the presence of human participants, must not endanger humans within the span of the robotic arm. Therefore constraining it to perform tasks within the limits of human movement may be a reasonable safety precaution. If this constraint is not required, the requirements defined in this description can readily be extrapolated to cover broader requirements for controlling the movement of a robotic arm and gripper. Also, operating a robotic arm and gripper, and the associated motion and orientation module or device, in servo mode can enable even greater levels of accuracy and precision. A robotically assisted extension of some medical and surgical procedures may enhance consistency of outcomes as some literature on robotic-assisted procedures asserts.

In addition to estimating the levels of acceleration and range of frequencies that must to be measured as well as the required sampling frequency and resolution of measurements, determining the selection criteria for accelerometers and analog to digital converters (ADC) requires knowledge of accelerometer and analog to digital conversion operations and performance. There are several types of accelerometers. Common types of accelerometers include: capacitive accelerometers and piezoresistive accelerometers.

Capacitive accelerometers have a moveable micromachined feature that acts as one side of a variable capacitor with respect to a fixed structure within the integrated circuit die. Movement of the integrated circuit causes displacement of this moveable structure resulting in a change in the level of capacitance that is proportional to acceleration, including gravity.

Piezoresistive accelerometers are based on a beam or micromachined feature whose resistance changes as it is flexed by movement of the proof mass. Movement of the proof mass is proportional to acceleration, including gravity.

Bulk MEMS capacitive and piezoresistive accelerometers can have some of the highest accuracy specifications of the commonly available accelerometer technologies for general linear accelerometer applications.

Piezoelectric accelerometers are dynamic accelerometers having a crystal sensing element that emits a charge when compressed by movement of the proof mass.

Magnetoresistive accelerometers convert acceleration to an electrical signal by measuring the resistance of a material whose resistivity changes with changes in the surrounding magnetic field.

Hall Effect sensors convert acceleration to an electrical signal by sensing changes in the surrounding magnetic field.

A thermoelectric accelerometer uses heated gas molecules to detect acceleration. Thermocouples are placed opposite four sides of a heat source suspended within a cavity. Under zero g, the temperature is the same at all four thermocouples. Acceleration in any direction will cause the temperature profile to become asymmetrical creating differences in output voltages of individual thermocouples proportional to the acceleration.

An optoelectronic accelerometer uses an optical position sensor (OPS,) or position sensitive detector (PSD), to provide an analog output voltage from a photodiode surface that is proportional to the position and movement of the centroid of a spot of light influenced by the movement of a proof mass.

An interferometric accelerometer detects the movement of the proof mass with an interferometric fiber optic sensor.

Microelectromechanical (MEMS) accelerometers are rugged, low cost and small in size. They may be discrete components or fabricated as either surface or bulk MEMS structures within integrated circuits. The individual outputs of each accelerometer integrated within an integrated circuit die or multi-circuit package may be oriented along each of axis of the Cartesian coordinates. The output from these acceleration sensing structures may be analog electrical parameters or signals, output frequencies, pulse interval modulation streams, or digital values from an analog to digital convertor. More complex integrated circuits may include additional functions integrated within the individual integrated circuit chip or die.

Just as an accelerometer converts physical acceleration into electrical signals or changes in electrical parameters, the output of an accelerometer can be converted into digital data that can be processed by logic circuits. Conversion from analog signals to digital or binary values inherently involves comparator action where the value of the analog voltage at some point in time is compared with some standard. Basic analog to digital conversion circuits include: successive-approximation; sigma-delta; flash, parallel, or direct conversion; pipeline; digital ramp; and various implementations of slope analog to digital conversion circuits. Resolution is a critical parameter that can drive the selection of specific analog to digital conversion circuits in many applications. Another parameter that can be critical in some applications is sample frequency or conversion rates. Pipeline and flash ADCs may be selected for these applications.

Other functions can also be included within a motion and orientation sensing module or device. For wireless operation telemetry circuitry, or telemetry circuit and antenna is required. Also, some form of control logic is required to coordinate the operation of the circuitry and sensors to assure the data from the acceleration sensing structures is transmitted successfully to an external computer system. This control logic may require inputs from the user and some form of touch sensitive input structures or functions are required. Obviously all these sensors and circuitry require power to operate. Therefore a power source, such as a battery or large-value capacitor, as well as some form of ON/OFF, START/STOP switching structure is required.

Critical factors that can affect the accuracy and resolution of the measurement of acceleration and tilt include: mechanical instability and electrical noise.

Mechanical instability or loose components or wiring can cause mechanical noise that is picked up by an accelerometer, or can even result in erroneous or spurious movement of the acceleration sensors element within an accelerometer, creating spurious acceleration and tilt data.

Electrical noise can limit the ENOB of the data conversion processing chain composed of the acceleration sensors, conversion to digital signals, and interference affecting telemetry transmissions. ADCs and signal conditioning circuitry may generate noise internally. Also cross talk or digital circuitry may create noise on power supply conductors shared with other circuitry.

High-precision analog semiconductor devices are sensitive to physical stress at the die and packaged circuit levels.

Thermoelectric voltages, the Seebeck effect, can be generated at junctions of dissimilar metals. Generated voltages can be as large as a millivolt for a change in temperature of one degree centigrade.

As with all precision circuits, drift of temperature sensitive elements within the electronic components and substrate can be a major source of error.

Long-term stability can also be a factor affecting the performance of high precision sensors and analog circuits as they undergo long-term age-related changes.

Variations in supply voltage can also affect the conversion of the amplitudes and directions of acceleration and tilt to binary outputs. In some circuits a major potential for error in the analog to digital conversion process is the lack of high-precision reference voltages.

Methods for addressing these issues are well defined. The evaluation and application of selected design approaches that can mitigate or eliminate the impact of individual sources of inaccuracy and level of resolution are well known and can support the attainment of ppm performance.

Motion and tilt sensing modules and devices must have high levels of mechanical integrity. At least one embodiment is less than a cubic centimeter, that expert mechanical design, mature electronic manufacturing methods, and careful selection of materials used for the substrate and enclosure can assure the required level of mechanical integrity and stability. This includes securely mounting all components, the substrate, and all wiring so that accelerometers are only subjected to external sources of motion or vibration.

Likewise the connection between the motion and orientation of the sensing module or device and the probe, tool, instrument, or similar apparatus it is attached to, affixed on, or embedded or integrated within, must have high integrity and stability. The small size also facilitates attaching motion and orientation module or device to, affixing it on, or embedding or integrating it within, a probe, tool, instrument, alignment jigs or cutting blocks, or other similar apparatus. It can then be calibrated to provide accurate data on the movement and orientation of the probe, instrument, or instrument while it is moved to simulate worst case usage. This calibration information can be stored within the circuitry of the motion and orientation module or device and used in conjunction with an auto-calibration procedure to assure the required accuracy and precision.

Also, the mechanical design and manufacture of the substrate and enclosure must assure highly accurate orientation of the acceleration sensors within the motion and orientation sensing module or device. To achieve the greatest resolution, the integrated circuit or circuits containing accelerometers can be mounted with the sensitive axes either parallel or normal to the plane of movement, depending on the mechanical design of the sensor. Tilt measurements are also sensitive to the orientation of the sensor. These measurements are most sensitive when the accelerometer is in its 0 g orientation. As a DC accelerometer's sensitive axis is tilted from pointing horizontal to vertical, the influence of gravity varies as a function of the sine of the angle between the horizon and the accelerometer's sensitive axis. Therefore any errors in the mounting of DC accelerometers are highly significant. The substrate can be mounted within the motion and orientation sensing module or device for maximum sensitivity when it is in its final position on or within the instrument, probe, instrument, alignment jigs or cutting blocks, or similar apparatus.

In at least one embodiment noise reduction and noise canceling measures can be included in the design. This includes incorporating filtering, dithering, oversampling, and decimation functions in the analog signal to digital code conversion process. The likelihood of an analog signal being exactly equal to a digital value is small. Therefore a combination of dithering and oversampling is capable of developing an accurate estimate of the actual value of a point on an analog waveform to a greater level of resolution than direct sampling.

Only pure sine waves are harmonic free. Even then, nonlinearity may create harmonics and intermodulation products. Therefore anti-aliasing low-pass filtering is required to remove harmonic signals and intermodulation products and all other signals above the Nyquist frequency that can introduce nonrandom distortions into the oversampled, dithered analog waveforms. Dithering an analog signal adds a white noise or Gaussian noise component that creates a stochastic variable with a mean value of zero for each sample of the analog waveform. The combination of dithering and oversampling enables the interpolation of analog values at each point on the analog waveform. Over-sampling increases the number of discrete samples compromising the digitized representation of an analog waveform. The greater the sample rate of the analog to digital conversion the more accurate the representation of the input signal is when the oversampled digital values are recombined. This sample rate may be as little as twice the Nyquist frequency as much as 256 times the Nyquist frequency. For each desired additional bit of resolution the analog signal can be oversampled by at least four times.

The oversampled analog-to-digital converted signal can be low-pass filtered to limit the effects of quantization noise without affecting DC accuracy. Quantization noise is inherent in the analog to digital conversion process. It is the result of the quantization process as it converts a continuous waveform to discrete values. A low pass quantization filter can also help attenuate higher frequency mechanical and electrical noise and improve the overall signal to noise ratio of the physical acceleration to digital code conversion process.

Decimation is required to digitally down-sample the oversampled digital values by aggregating groups of oversampled digital values with the number of digital values within each group depending on the down-sampling divisor. Each down-sampled digital value is then right shifted to scale the answer correctly to the increased level of resolution required for the final high-resolution digital values.

The combination of anti-alias filtering, dithering, oversampling, quantization filtering, and decimation functions can extend the effective number of bits (ENOB) of the data conversion chain linking physical acceleration to a digitized waveform by three or more least-significant-bits. This may be required to assure ppm resolution in the analog to digital conversion process.

Well-designed electrical conductor widths, routing, partitioning, and shielding on and within the substrate also minimizes noise and cross-talk.

Expert design and good manufacturing process control minimizes the level of physical stress placed on integrated circuit die and packaged devices and eliminates this potential source of error.

The same is true for thermoelectric voltages created by the Seebeck effect. The number of junctions of dissimilar metals, and the magnitude of thermoelectric voltages created where junctions of dissimilar metals must interface, is minimized by appropriate selection of materials and electronic assembly methods.

Changes in the temperature of the environment of the motion and orientation sensing module or device when it is in operation are minimal. First, the environment within operating rooms or other sections of healthcare facility are carefully maintained. Second, the power consumption of the motion and orientation sensing module or device is very low and does not materially raise its operating temperature. These two factors minimize the changes in temperature of sensitive components and effectively eliminate temperature drift as a source of error during the relatively brief time the motion and orientation sensing module or device is active.

An application wherein the starting location and orientation may be used as the target location and orientation provides a substantial advantage in tracking the progress of the motion and orientation sensing module or device. In these applications the sum of distances traveled in all three axes is zero and the sum of changes in orientation in all three axes is also zero, the relative values of acceleration and tilt are more critical, and the absolute values of acceleration are less critical. This greatly reduces the impact of many of the factors that can adversely impact the accuracy and precision of the conversion of physical acceleration to digital values.

Achieving relative accuracy with high levels of resolution is more tractable because even if precision components and circuits, as well as reference and supply voltages, drift slowly over time this will not adversely impact the accuracy, or effective number of bits required for relative measurement results. Therefore aging and temperature changes are not major deterrents to ppm performance of the motion and orientation sensing module or device during the relatively brief time the motion and orientation sensing module or device is active.

Furthermore, precision electronic sensors and components do not age rapidly enough for aging to be a factor in their performance within the time required for an individual surgical or medical procedure. Also, because of sterility requirements in medical procedures and facilities, the motion and orientation sensing modules and devices are limited to single-use in many applications.

In addition to the accuracy and resolution of the conversion of acceleration into electrical signals, the accuracy and resolution of the conversion of analog voltage to digital values is key determinate of the ENOB. The performance of ADC circuits is dependent on many factors. Specifications for the various forms of noise, offset, gain, and linearity specifications are all critical to achieve ppm performance and can be thoroughly reviewed.

A conservative estimate of the requirements for the application of accelerometer technologies for medical applications indicates these accelerometers must detect changes of one millionth of the total capacitance or resistance respectively. Repeatable ppm sensitivity, with no missing codes, in an 8 g accelerometer is required to achieve an ENOB of 20. This requires the application of multiple measures for enhancing the performance of accelerometers, analog to digital converters, and reference voltages, including: High resolution capacitive or piezoresistive accelerometers, or a force-balance, force-feedback, or servo mode operation of variable capacitor accelerometers.

Ratiometric operation incorporated into accelerometer and ADC circuits facilitates the conversion of changes in acceleration and tilt into binary outputs that are independent of drift and variations in supply and reference voltages. Sigma-delta analog to digital conversion can also be used in the ADC circuitry.

The complete analog to digital conversion process can incorporate low pass anti-alias and quantization filtering, dithering, oversampling, and decimation functions in the conversion of physical acceleration to binary outputs with the effective number of bits to achieve ppm resolution. Chopper stabilization of the ADC inputs can also minimize offset and drift.

Executing an automatic calibration procedure as the circuitry is powered-up can mitigate offset and gain errors, aging or temperature sensitivities of the sensors and electronic circuitry, as well as confirming the noise floor and battery voltage and charge of the motion and orientation sensing module or device.

In addition to the level of integration of the acceleration sensors and circuitry, there is also a range of possible software functions that may be integrated into an individual motion and orientation sensor module or device. These features include detection of several exception conditions, including: free-fall, tumbling, spinning, shock, and tap and double tap. In addition to the accelerometer or accelerometers and ADC, filtering or digital signal processing circuitry can be used to detect and quantize the signals necessary for these additional functions. This can include low pass and high pass filters to discriminate among various types of exception condition signals.

Free-fall detection will alert the computer system, and the user, if the motion and orientation sensor module or device is dropped. A free-fall condition is detected whenever the static acceleration average output of all three acceleration sensing elements drops to zero or g. Output from the accelerometers may still have cyclic dynamic output. This may indicate the motion and orientation sensing module or device is also tumbling or spinning while it is falling. Whenever any of these conditions are detected, it can indicate the need to reset and restart the tracking procedure.

A physical transient or shock is detected whenever a high frequency dynamic acceleration signal exceeds a pre-set level in one or more axes. Transient detection is based on signals from a high pass filter that filters out static acceleration and low speed acceleration signals. This may indicate the probe, instrument, or instrument has been subjected to mechanical shock such as striking, or been struck by, a solid object. It may be appropriate to reset and restart the tracking procedure after this condition is detected as well.

Obviously acceleration sensors may also be used to detect tap and double taps on the motion and orientation sensing module or device, or the probe, instrument, or instrument. This capability may enable the surgeon to give START and STOP commands without removing his or her hands from the probe, instrument, or instrument.

These examples of software functions that can be used to leverage the flow of information available from the dynamic and static sensing of acceleration and tilt illustrate the significant real-time utility available, not only by detecting and tracking motion and orientation, but by analyzing its features in real time. Leveraging these capabilities maximizes the information content of these data streams.

There are many possible applications of motion and orientation sensing modules or devices in medical and surgical procedures. For example, the benefit of trialing may enhance the use of a tracking motion and orientation sensing module or device. The addition of a second marker motion and orientation sensing module or device may improve the accuracy and resolution of the replacement of a measurement instrument, trial insert, or prosthetic component if there is any possibility of even microscopic movement by the patient. Data from this market module or device is used to track movement and changes in orientation of the target. Within a trialing application the tracking motion and orientation sensing modules or devices may be used to track the retraction of a measurement instrument, trial insert, or prosthetic component. The same motion and orientation sensing module or device can then be used to guide the positioning and orientation of the chronic implant device in various orthopedic procedures. For example, a spinal disk replacement procedure, or a prosthetic implant in any joint, are examples that illustrate the application of motion and orientation sensing modules or devices to guide the movement and orientation of a medical instrument. There are multiple methods where a chronic implant might be guided back to the precise location and orientation identified with the use of a measurement instrument, trial insert, or prostheses or prosthetic component.

Possible approaches can include: a single instrument that precisely grips different trial inserts, or prostheses or prosthetic components, as well as the final implant, attaching the same motion and orientation sensing module or device to different identical instruments with each one specialized to hold different sized trial inserts as well as the final implant, two instruments, each having a separate motion and orientation device. One instrument optimized for holding trial inserts or prostheses or prosthetic components, and a second instrument optimized for holding the chronic implant. When the instruments are placed in precise physical contact a signal is generated and the computer software computes the location and orientation of the second instrument based on the location and orientation of the first instrument.

The addition of a motion and orientation sensing module or device to a generic instrument illustrates how it may be used to assist in guiding the positioning and orienting the replacement disk accurately within a patient's spine. In addition to a generic instrument having a motion and orientation sensing device, this example also illustrates the role computer hardware and software provide to the development of a systems solution. If the implant site in this example application cannot be assured to be absolutely fixed, a second, marker, motion and orientation sensing device can be pinned to the patient's body near enough to the implant site that its position and orientation are fixed with respect to the site of the implant. The data from this second device can be used to adjust the target location so it continues to accurately correspond with the implant site even if it is moving slightly. This will assure the accuracy of the positioning and orientating of the implant within the required level of precision.

Various example embodiments of example motion and orientation sensing modules or devices, an example application of a disk replacement procedure, example flowcharts of an example approach to the process and role of software within the procedure, as well as example computer display images, are illustrated in the following figures.

The following figures will be used to describe non-limiting examples of a subset of possible embodiments. FIG. 1 is a simplified view 2000 of a physician holding an embodiment of a surgical tracking system including a motion and orientation sensing device (e.g., a surgical device holder portion of a surgical tracking system) with a computer display (e.g., a surgical tracking display system) of its location and orientation at some distance from a pre-specified target. FIG. 1 illustrates the use of real-time data from an example wireless motion and orientation sensing device to provide real-time visual feedback to aid a physician to guide a medical probe or instrument to a predefined location and contacting that location at a predefined orientation. In this example a sagittal view of knee joint 2004 is used as an illustration of an anatomical feature defining a target location and orientation. Computer display 2016, connected to computer 2014 (optionally including a processor that can process tracking data), having computer keyboard 2010 and computer mouse 2012, displays image 2020 of a target location within knee joint 2004. Computer display 2016 also displays image 2018 of the target orientation within knee joint 2004. For example physician 2002 holds a medical instrument 2008 (surgical device) having an example embodiment of a motion and orientation sensing device 2006 (surgical device holder). Physician 2002 is prepared to move instrument 2008 to the target location and orientation within knee joint 2004. The example embodiment of a motion and orientation sensing device 2006 detects, quantizes, and transmits movement, tilt, and yaw data to computer 2014 (e.g., the computer display of a surgical tracking display system). This data will begin updating images 2018, 2020 on display screen 2016 as physician 2002 begins to move instrument 2008.

FIG. 2 is a simplified view 2100 of a physician holding an embodiment of a surgical tracking system including a motion and orientation sensing device (e.g., surgical device holder) with a computer display (e.g., the computer display of a surgical tracking display system) of its location and orientation approaching a pre-specified target. FIG. 2 illustrates the use of tracking data from an example wireless motion and orientation sensing device to provide real-time visual feedback to aid a physician to guide a medical probe or instrument to a predefined location and contacting that location at a predefined orientation. In this example knee joint 2004 is used as an illustration of an anatomical feature having an example a target location and orientation. Computer display 2016 coupled to computer 2014 includes computer keyboard 2010 and computer mouse 2012 whereby image 2120 of the target location within knee joint 2004 is displayed. Computer display 2016 also displays an image 2118 of the target orientation within knee joint 2204. Example physician 2002 holds an example medical instrument 2008 having an example embodiment of a motion and orientation sensing device 2006 that detects, quantizes, and transmits movement, tilt, and yaw data to computer 2014. As physician 2002 moves example medical instrument 2008 motion and orientation sensing device 2006 transmits tracking data to computer 2014. Images of relative orientation 2118 and location 2120 on computer display 2016 are updated in real time. This enables physician 2002 to judge the difference in location and orientation between instrument 2008 and the target location and orientation within knee joint 2004 while he or she continues to move instrument 2008. Updates of images 2118, 2120 on computer display 2016 continually reflect the movement of medical instrument 2008 until it reaches the target location and orientation with the patient's knee 2004. The combination of motion and orientation sensing device 2006 and real-time updates of images 2118 and 2120 on computer display 2016 aids a user (e.g. physician) 2002 to accurately guide instrument 2008 precisely to the target location and orientation within knee joint 2204.

FIG. 3 is a simplified view 2200 of a physician holding an embodiment of a surgical tracking system including a motion and orientation sensing device with a computer display defining its location and orientation at some distance from a pre-specified target plus a second motion and orientation sensing device pinned to a patient to track any movement of the target. FIG. 3 illustrates the use of real-time data from two example wireless motion and orientation sensing devices to provide real-time visual feedback to aid a physician to guide a medical probe or instrument to a predefined relative location and contacting that location at a predefined relative orientation. In this example a sagittal view spine 2204 is used as an illustration of an anatomical feature having a possible target location and orientation 2222. Example physician 2202 holds example medical instrument 2208 (e.g., surgical device) having an example embodiment of a motion and orientation sensing device 2006. In a second embodiment a marker motion and orientation sensing device 2223 is affixed to the body of patient 2224 in a fixed position and orientation with respect to target location and orientation 2222, providing movement information that will affect the position and orientation of the target location. Computer display 2016, connected to computer 2014, having computer keyboard 2010 and computer mouse 2012, displays image 2220 of the distance between instrument 2208 and target location 2222 on spine 2204. Computer display 2016 also displays image 2218 of the difference between the orientation of instrument 2208 and the orientation of target location 2222. Physician 2202 is prepared to move instrument 2008 to the target location and orientation 2222 within spine 2204. The example embodiments of motion and orientation sensing devices 2006, 2223 will detect, quantize, and transmit movement, tilt, and yaw data to computer 2014. Images 2218, 2220 on display screen 2016 can be updated in real time as physician 2202 begins to move instrument 2008.

FIG. 4 is a simplified view 2300 of a physician holding an instrument having an embodiment of a motion and orientation sensing device with a computer display defining its location and orientation approaching a pre-specified target while a second motion and orientation sensing device pinned to a patient tracks any movement of the target. FIG. 4 illustrates the use of real-time data from two example wireless motion and orientation sensing devices to provide real-time visual feedback to aid a physician to guide a medical probe or instrument to a predefined relative and contacting that location at a predefined orientation. In this example a sagittal view of spine 2204 is used as an illustration of an anatomical feature having an example target location 2222. Example physician 2202 holds example medical instrument 2208 having an example embodiment of a motion and orientation sensing device 2006. The example embodiment of a tracking motion and orientation sensing device 2006 detects, quantizes, and transmits acceleration, tilt, and yaw data to computer 2014 in real time as physician 2202 moves example medical instrument 2208. Simultaneously, example embodiment of a marker motion and orientation sensing device 2223 detects, quantizes, and transmits acceleration, tilt, and yaw data to computer 2014 in real time as spine 2204 of patient 2224 moves, even microscopically. Computer display 2016, connected to computer 2014, having computer keyboard 2010 and computer mouse 2012, displays image 2320 of the relative position of instrument 2208 with respect to target location 2222 on spine 2204. Computer display 2016 also displays image 2318 of the relative orientation of instrument 2208 with respect to the orientation of target location 2222. The images of the target location 2320 and the orientation of the target 2318 on display screen 2016 are updated in real time with data from example marker motion and orientation sensing device 2223. Updating image 2320 in real time with data collected from both example motion and orientation sensing devices 2006, 2223 enables physician 2202 to accurately judge the distance between the leading edge of instrument 2208 and target location 2222 even if the target location is not absolutely fixed. Simultaneously, updating image 2318 in real time with data collected from both example motion and orientation sensing devices 2006, 2223 enables physician 2202 to accurately judge the difference in orientation between instrument 2208 and target location 2222 even if the target location is not fixed. The combination of example motion and orientation sensing devices 2006, 2223 and real-time updates of images 2318 and 2320 on computer display 2016 aids physician 2202 to accurately guide instrument 2208 to target location 2222 within spine 2204 with the required orientation and precision even if target location is fixed or moving slowly or slightly.

FIG. 5 is a simplified perspective view 2400 of an example of a motion and orientation sensing device, a cover for the device, and an instrument into which a motion and orientation sensing device may be placed. FIG. 5 illustrates a simplified perspective exploded view of an example medical instrument and an example motion and orientation sensing device, prior to assembly. The example motion and orientation sensing device 2006 detects, quantizes, and transmits data defining the movement, tilt, and yaw of example medical instrument 2402. In this exploded view of example medical instrument 2402 having cavity 2404 and cover 2414 sized to hold example motion and orientation sensing device 2006 securely within its handle 2406. When assembled, example medical instrument 2402 having shaft 2408 and coupling 2410 may be used to track the movement and orientation of example medical inserts or prosthetic components or implants held in interchangeable heads mounted on coupling 2410.

FIG. 6A is a simplified perspective view 2500 of an example instrument having an example motion and orientation sensing device, a cover for the device, an interchangeable head, and an example insert or implant that may be held by the instrument. FIG. 6A illustrates a simplified perspective exploded view of an example medical instrument prior to assembly with an example motion and orientation sensing device, interchangeable head, and example medical insert or prosthetic component or implant. The example motion and orientation sensing device 2006 detects, quantizes, and transmits data defining the movement, tilt, and yaw of an example medical insert, implant, prosthetic component or prostheses 2518. In this exploded view of example medical instrument 2402 having cavity 2404 and cover 2414 sized to hold example motion and orientation sensing device 2006 securely within its handle 2406. Example interchangeable head 2516 may be attached to medical instrument 2402 by plugging its base onto coupling 2410 on the end of shaft 2408. Example interchangeable head 2516 may be used to hold example medical inserts, prosthetic components, prostheses, or implants 2518. This completed assembly may be used to track the movement and orientation of an example medical example medical insert, prosthetic component, prostheses, or implant 2518 in real time.

FIG. 6B illustrates a simplified perspective view of an assembled example medical instrument having an example motion and orientation sensing device for tracking its movement and orientation, an interchangeable head, and an example medical insert or prosthetic component or implant held by the instrument. When assembled the medical instrument 2402 having example motion and orientation sensing device 2006 may be used to track the movement and changes in orientation of example medical insert, prosthetic component, prostheses, or implant 2518. The example motion and orientation sensing device 2006 detects, quantizes, and transmits data defining the movement, tilt, and yaw of example medical insert, prosthetic component, prostheses, or implant 2518 in real time. Example medical instrument 2402 having handle 2406 and shaft 2408, plus cover 2414 securing example motion and orientation sensing device 2006, may be used to track changes in the location and orientation of medical insert, prosthetic component, prostheses, or implant 2518 when positioned securely 2520 within interchangeable head 2516.

FIG. 7 is a simplified example top-level flow chart of the steps performed by an example system having an embodiment of the motion and orientation sensing module or device and a computer system for guiding an instrument to return to its initial position. FIG. 7 illustrates a simplified example flow chart of the steps performed by an example system having an embodiment of the motion and orientation sensing module or device with a real-time display to aid a user in guiding a probe, instrument, alignment jigs or cutting blocks, or similar apparatus having a motion and orientation sensing module or device integrated or embedded into, affixed onto, or attached to it. The instrument may be locally or remotely controlled to accurately orient and position its active tip or member to return precisely to its initial position and orientation. If a second, or marker, example motion and orientation sensing device is positioned to track any change in location or orientation of the target, that device will be referred to as a 'marker device' and the motion and orientation sensing module or device used for tracking movement and changes in orientation of a probe, tool, instrument, alignment jigs or cutting blocks, or similar apparatus will be referred to as a 'tracking device.' The relationships among the nine top-level functions required to perform the tracking procedure include actions by the user, processes executed by the motion and orientation sensing module or device, and software procedures executed by the computer system.

In step 2600 a top level software transfers control to subordinate routines and functions as required to perform the tracking procedure.

In step 2602 the user prepares for tracking a probe, tool, instrument, or alignment jigs or cutting blocks, or similar apparatus, by defining the target location and orientation, and powering the motion and orientation sensing module or device 2700. Powering-up the motion and orientation sensing module or device may be as simple as pressing a START button or icon, or double-tapping the handle of the case of the motion and orientation sensing module or device or the handle of the associated probe, tool, instrument, or alignment jigs or cutting blocks, or similar apparatus.

In step 2604 control is transferred to the motion and orientation sensing module or device to execute its power up procedure 2800 and transmit the results to the computer.

In step 2606 control is transferred to software routine 2900 that directs the example motion and orientation sensing module or device to quantify and transmit the initial orientation tracking data point and the corresponding static acceleration of gravity to the computer.

In step 2608 control is transferred to software routine 3000 that directs the example motion and orientation sensing module or device to detect initial movement and transmit the second tracking data point to the computer.

In step 2610 control is transferred to software routine 3100 that directs the example motion and orientation sensing module or device to detect and transmit tracking data for motion and orientation samples two through one-hundred to the computer.

In step 2612 control is transferred to software routine 3200 that directs the computer to calculate and display the trajectory and orientation of the motion and orientation sensing module or device through the first one hundred data tracking points.

In step 2614 control is transferred to software routine 3300 that calculates and displays the trajectory and orientation of the motion and orientation sensing module or device through each additional successive movement and orientation data point.

In step 2616 if the motion and orientation sensing module or device detects an exception condition it signals an alarm that triggers an alert by the computer. Also, if the user elects to stop tracking, or the tracking procedure is completed, needs to be restarted, or can be aborted, control is transferred to the exception processing routine 3500.

Figure 8:
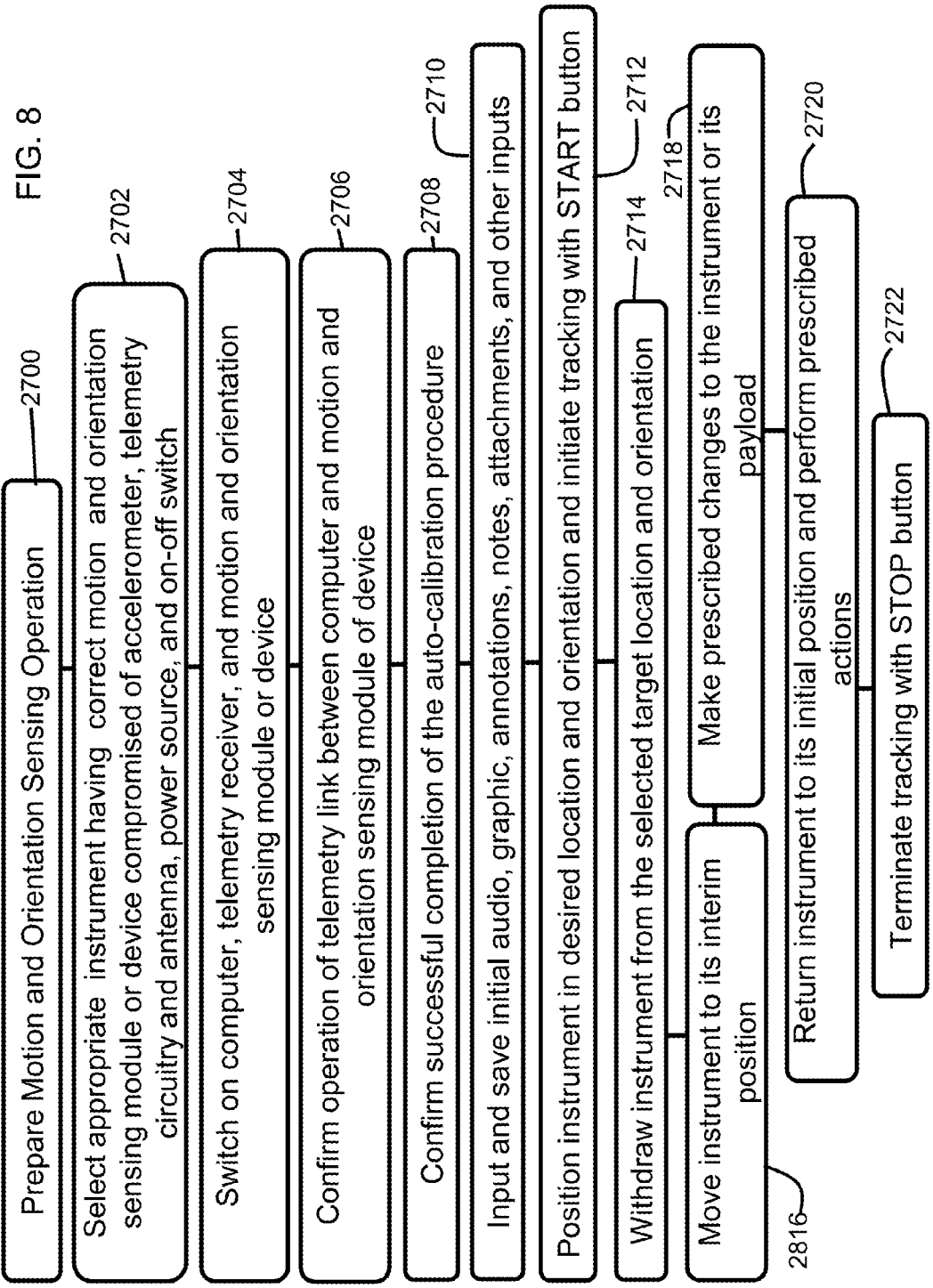
FIG. 8 illustrates a simplified example of a flow chart of the steps performed by a physician or other user preparing to use an example embodiment of the motion and orientation sensing module to guide an instrument to return to its initial location and orientation.

FIG. 8 illustrates a simplified example flow chart of the steps performed by a physician, surgeon, or other user preparing to use an example embodiment of the motion and orientation sensing module or device to guide a medical instrument to return to its initial location and orientation.

In step 2700 the user is alerted by the computer display that the control software is in the proper state for the preparation of the example motion and orientation sensing module or device.

In step 2702 the user begins the preparations for tracking a probe, instrument, alignment jigs or cutting blocks, or similar apparatus by identifying the target location and orientation. The user selects the appropriate probe, instrument, or similar apparatus for the procedure to be performed and prepares it for its role in the procedure. The user also prepares to apply the motion and orientation sensing module or device positioned, affixed, or integrated on or within the probe, instrument, or similar apparatus.

In step 2704 the user powers up the motion and orientation sensing module or device when it is attached or affixed to, embedded in, or integrated with the appropriate probe, instrument, alignment jigs or cutting blocks, or similar apparatus. The user confirms the computer, telemetry receiver, and motion and orientation sensing module or device are powered up and ready to use. Powering up the motion and orientation sensing module or modules or device or devices may be as simple as pressing a POWER button or icon on the handle or case of each motion and orientation sensing module or device or tapping the handle of the associated instrument.

In step 2706 the user checks the screen of the computer and confirms that the telemetry link between the computer and each motion and orientation sensing module or device is operational.

In step 2708 the user checks the screen of the computer and confirms that each motion and orientation sensing module or device has adequate battery voltage and charge, the temperature is within elements, the auto-calibration procedure was successful, and the identification code is correct.

In step 2710 the user inputs initial audio, graphic, annotations, notes, attachments, and other information into the electronic health record being assembled on the computer for this procedure on this patient.

In step 2712 the user positions the instrument, and the marker device if one is needed, in the desired locations and orientations and initiates tracking. Initiating tracking may be as simple as pressing each START button or icon a second time, or double-tapping the handle of the handle of the instrument a second time.

In step 2714 the user withdraws the instrument from the selected target location and orientation after confirming that the target location and orientation has registered with the computer. The user continually monitors the computer display for any alarm conditions and taking any appropriate actions or entering appropriate instructions or data to the computer as required.

In step 2716 the user moves the instrument to its interim position while continuing to monitor the computer display for any alarm conditions and taking any appropriate actions or entering appropriate instructions or data to the computer as required.

In step 2718 the user makes the prescribed adjustments, changes, or replacements to the instrument or its payload while continuing to monitor the computer display for any alarm conditions and taking any appropriate actions or entering appropriate instructions or data to the computer as required.

In step 2720 the user moves the instrument back to its initial position and performs the prescribed actions at the target location and orientation while continuing to monitor the computer display for any alarm conditions and taking any appropriate actions or entering appropriate instructions or data to the computer as required.

In step 2722 the user terminates tracking with a STOP button, icon, or double tap on the motion and orientation sensing module or device or tapping the handle of the instrument. This transfers control to the Exception Processing routine 3500. Within that procedure the user inputs any final audio, graphic, annotations, notes, attachments, and other information into the electronic health record assembled by the computer and stores the file in the appropriate database and execution of the tracking procedure is terminated.

Figure 9:
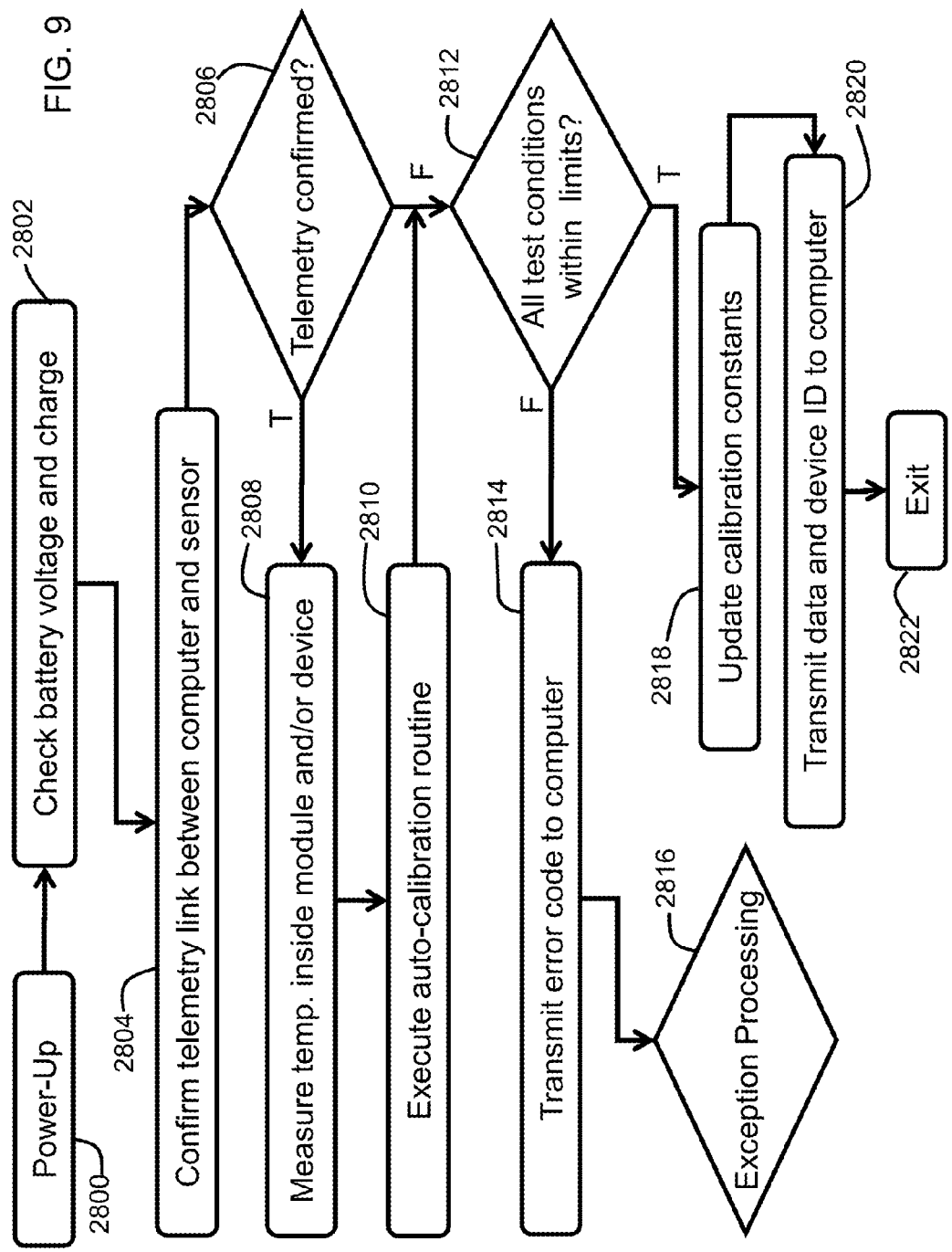
FIG. 9 illustrates a simplified example of a flow chart of the steps performed by an example embodiment of the motion and orientation sensing module to prepare for tracking of changes in its location and orientation.

FIG. 9 is a simplified example flow chart of the steps performed by an example embodiment of the motion and orientation sensing module to prepare for tracking of changes in its location and orientation. FIG. 9 illustrates a simplified example flow chart of the steps performed by an example embodiment of each motion and orientation sensing module or device to prepare for tracking changes in its location and orientation. An automatic calibration procedure is executed whenever power is applied to each motion and orientation sensing module or device. This assures the accuracy of accelerometers by assuring there is no offset voltage under 0 g conditions. It also uses the acceleration of gravity as a second calibration point for confirming scale parameters. This assures the accuracy of the sensing, conversion, and transmission of acceleration and tilt in all three axes. The effects of offset and gain errors in the ADC are also addressed by the automatic calibration routine. Confirming operating temperature, reference voltage, and adequate power level during the start-up of each motion and orientation sensing module or device minimizes the risk of inaccuracies or inconsistent tracking operation.

Whenever a motion and orientation sensing module or device is switched on power-up procedure 2800 is executed. This includes the steps: 2802 the battery voltage and level of charge within each motion and orientation sensing module or device are measured; 2804 each motion and orientation sensing module or device transmits an initial telemetry signal to the telemetry receiver connected to the computer; 2806 does the computer display confirm reception of each initial telemetry signal? If not, go to step 2812. This will result in the conditional expression at step 2812 to fail and control will be transferred to the Exception Processing routine 3500. Then 2808 the temperature within each motion and orientation sensing module or device is measured; 2810 the auto-calibration routine within each motion and orientation sensing module or device is executed; and the control is transferred to step 2812 to confirm correct results for all start-up tests. In step

2812 Battery voltage and charge, temperature, and calibration results are checked against specification to assure reliable operation of each motion and orientation sensing module or device. If all measurements have the required values and telemetry is functional control is transferred to step 2818.

In step 2814 if one or more measurements did not have the required values, an error code is transmitted to the telemetry receiver connected to the computer defining the exception condition that has been detected. If the failure condition results from failure to establish a telemetry link this step will execute without any effect on the computer display.

In step 2816 control is transferred to the Exception Processing routine 3500.

In step 2818 if all measurements are within limits, the calibration constants for each motion and orientation module or device are updated and stored in nonvolatile memory within each device.

In step 2820 the data and device ID code of each motion and orientation module or device are transmitted to the computer.

In step 2822 control is returned to the control program at step 2606. The tracking procedure is now ready to begin as soon as the computer system displays the necessary data for the user to verify the ID codes.

Figure 10:
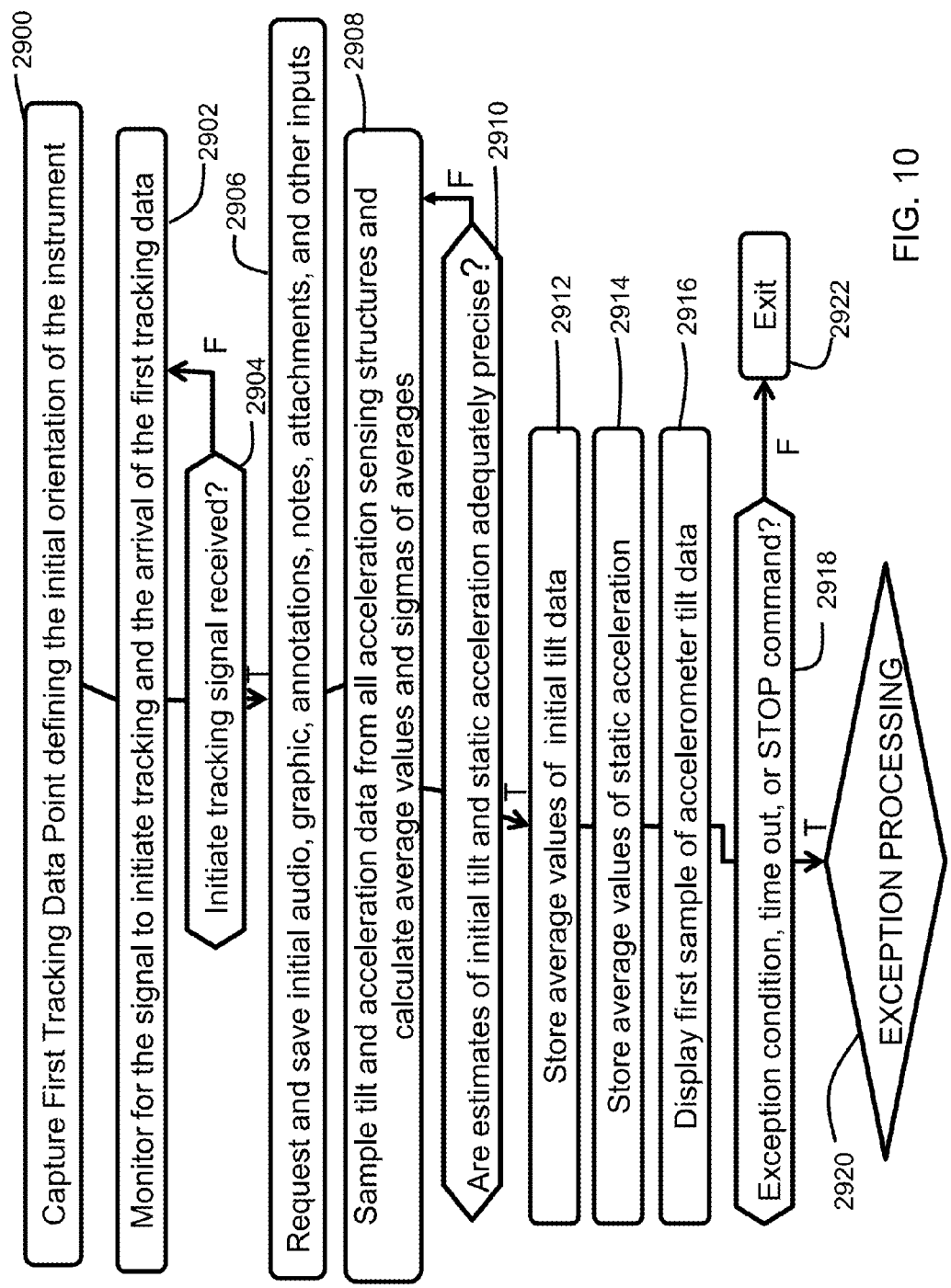
FIG. 10 illustrates a simplified example of a flow chart of the steps performed by a computer to capture the initial orientation data from an example embodiment of the motion and orientation sensing module or device.

FIG. 10 is a simplified example flow chart of the steps performed by a computer to capture the initial orientation data point and static acceleration of gravity corresponding to that orientation from an example embodiment of the motion and orientation sensing module or device.

In step 2900 control is transferred to the software routine that performs the necessary actions to capture the data point defining the initial orientation of an example probe, tool, instrument, or alignment jigs or cutting blocks, or similar apparatus and a marker motion and orientation sensing module or device.

In step 2902 the computer software monitors the output of the telemetry receiver for the command to initiate capturing accelerometer data transmitted by the tracking motion and orientation sensing module or device. The data defining the tilt in the gravity-sensitive axes of each motion and orientation sensing module or device are transferred through the telemetry receiver.

In step 2904 when the command to initiate the data capturing procedure is received the software proceeds to the next step 2906.

In step 2906 the computer screen displays a request for the user to enter any initial audio, graphic, annotations, notes, attachments, or other data input. An electronic health record is opened and all forms of the data input by the user are stored with the appropriate identifiers and tags.

In step 2908 each motion and orientation sensing module or device starts sampling the static acceleration of gravity data defining tilt and the strength of the corresponding static acceleration from each accelerometer sensing element of the triaxial accelerometers. The software updates the calculated averages of this data for each additional sample. Published values of the acceleration of gravity are not used for estimating the static component of the accelerometer readings because the actual acceleration of gravity is specific to geographic location on the surface of the earth.

In step 2910 if the sigma values of the averages of the tilt and static acceleration are too large to achieve the required precision of the initial tilt and static acceleration values, control is returned to step 2908. When the sigma values of the averages of the tilt and static acceleration achieve the required precision of the initial tilt and static acceleration control is transferred to step 2912.

In step 2912 the data defining the tilt of the tracking motion and orientation sensing module or device is stored in the orientation data array of the tracking software. This data may be adjusted with respect to the tilt of the tracking motion and orientation sensing module or device if a second, marker, example motion and orientation sensing device is active. The adjusted data from the tracking and marking devices are stored.

In step 2914 the values of the strength of static acceleration on each Cartesian axis is stored and subsequent samples of acceleration data are adjusted to estimate the dynamic acceleration during each sample period. Because the initial location defines the target location, the dynamic acceleration and the location values of each device are set to zero for each of the Cartesian coordinates aligned with the zenith and tangents to the surface of the earth. This data for the tracking module or device is stored in the acceleration data and location data arrays of the tracking software. The initial location of the marker device is also assumed to be 0,0,0 if one is in use.

In step 2916 the computer screen is updated to display the orientation the target location with the image of the instrument having the motion and orientation sensing module or device centered on that display.

In step 2918 the software examines the telemetry data to determine if a STOP command has been received or an exception condition detected.

In step 2920 whenever a STOP command or exception condition has been detected, control is passed to the Exception Processing routine 3500.

In step 2922 if no STOP command has been received and no exception condition detected, the control is returned to the top level of the tracking software program at step 2608.

Figure 11:
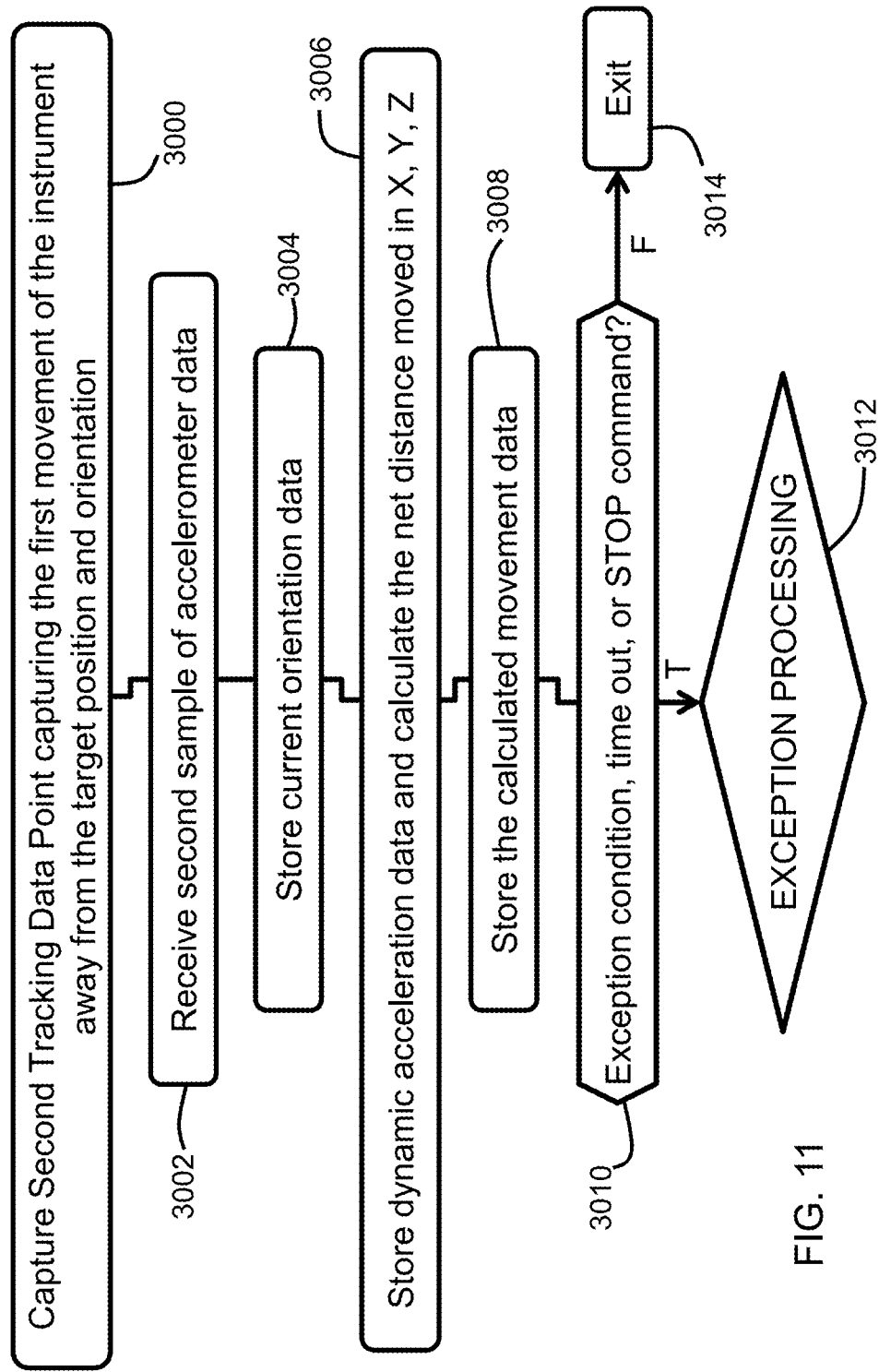
FIG. 11 illustrates a simplified example of a flow chart of the steps performed by a computer to capture the distance and direction of the initial movement of an example embodiment of the motion and orientation sensing module or device.

FIG. 11 is a simplified example flow chart of the steps performed by a computer to capture the distance and direction of the initial movement of an example embodiment of the motion and orientation sensing module or device.

In step 3000 control is transferred to the software routine that performs the necessary actions to capture the second data point defining the initial movement and the resulting location and orientation of an example probe, tool, instrument, or alignment jigs or cutting blocks, or similar apparatus.

In step 3002 the data defining the acceleration in all three Cartesian axes of each motion and orientation sensing module or device with respect to the zenith and tangents to the surface of the earth are transferred to the computer through the telemetry receiver. If a second, or marker, example motion and orientation sensing device is positioned to track any change in location or orientation of the target, the acceleration data may be adjusted for any changes in the location and orientation of the target before the tracking data is stored.

In step 3004 the data defining the orientation of the motion and orientation sensing module or device in all three Cartesian axes is stored in the orientation data array. If a second, or marker, example motion and orientation sensing device is active, the orientation data may be adjusted for any changes in the orientation of the target before the tracking data is stored.

In step 3006 the adjusted data defining the level of dynamic acceleration along each Cartesian axis are stored in the acceleration data array. The net average velocity along each Cartesian axis is calculated for the duration of each sample interval. If a second, or marker, example motion and orientation sensing device is positioned to track any change in location or orientation of the target, this net average velocity may be net of any changes in the location or orientation of the marker device. The calculated average net velocity of the tracking device with respect to any movement of the target is stored in the velocity data array.

In step 3008 the net change in distance traveled along each Cartesian axis during each sample interval is calculated and stored in the location data array. If a second, or marker, example motion and orientation sensing device is positioned to track any change in location or orientation of the target, this net average velocity will be net of any changes in the location or orientation of the target as well.

In step 3010 the software examines the telemetry data to determine if a STOP command has been received and also checks if an exception condition has been detected.

In step 3012 whenever a STOP command is received, or an exception condition has been detected, control is passed to Exception Processing routine 3500.

In step 3014 if no STOP command has been received or exception condition detected the computer returns control to the top level of the tracking software program at step 2610.

Figure 12:
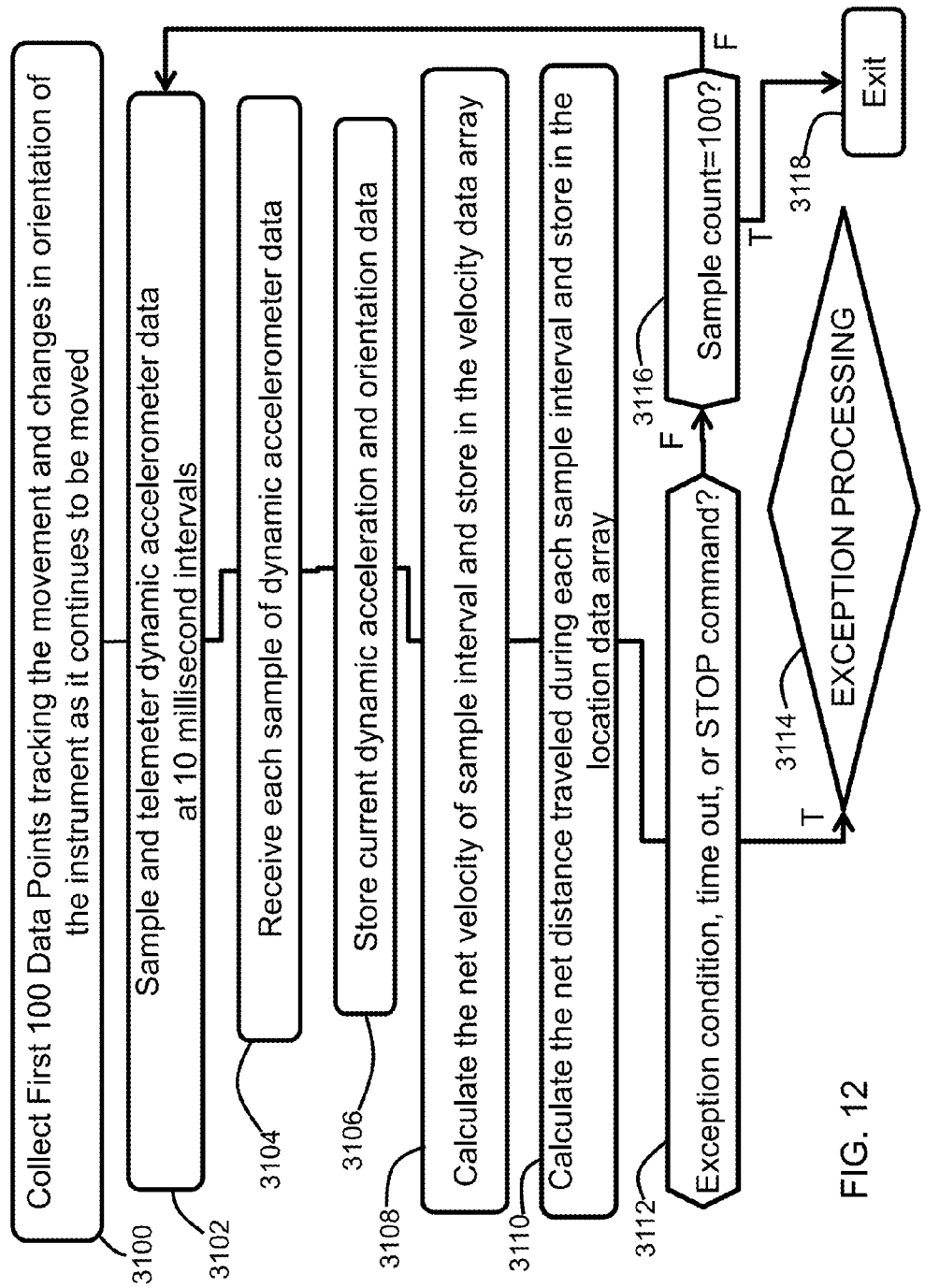
FIG. 12 illustrates a simplified example of a flow chart of the steps performed by a computer to capture the initial 100 movements of an example embodiment of the motion and orientation sensing module or device.

FIG. 12 illustrates a simplified example flow chart of the steps performed by the motion and orientation sensing module or device in conjunction with the computer to capture the initial 100 movements of an example embodiment of the tracking motion and orientation sensing module or device.

In step 3100 control is transferred to the software routine that performs the necessary actions to collect data points 2 through 100 defining the movement, location, and orientation of an example probe, tool, instrument, or alignment jigs or cutting blocks, or similar apparatus. If a marker device is active, the data may be adjusted based on movement or changes in orientation of the target.

In step 3102 each motion and orientation sensing module or device samples the dynamic accelerometer data every 10 milliseconds.

In step 3104 the dynamic acceleration and tilt data in all three Cartesian axes, defined with respect to the zenith and tangents to the surface of the earth, of the tracking motion and orientation sensing module or device are transferred to the computer through the telemetry receiver. If there is an example marker motion and orientation sensing device, data from tracking device may be adjusted to account for any movement or change in the location or orientation of the target before the data are transmitted.

In step 3106 the data defining the net levels of dynamic acceleration and tilt of the example tracking motion and orientation sensing module or device in all three Cartesian axes is stored in the acceleration and orientation data arrays. If an example marker motion and orientation sensing device is used in the procedure, the dynamic acceleration and orientation data can be adjusted for any changes in the location and orientation of the target.

In step 3108 the data defining the net average velocity along each Cartesian axis is calculated for the duration of each sample interval. The calculated average net velocity is stored in the velocity data array.

In step 3110 the net change in distance traveled along each Cartesian axis during each sample interval is calculated and stored in the location data array.

In step 3112 the software examines the telemetry data to determine if a STOP command has been received or the time without receiving data from the telemetry receiver has been exceeded.

In step 3114 whenever a timeout or other exception condition is detected, or the STOP command is received, control is passed to the Exception Processing routine 3500.

In step 3116 if all 100 tracking data points have not been captured, control is transferred to step 3102 to continue sampling the accelerometer data.

In step 3118 if no STOP command has been received, or exception condition detected, the computer returns control to the top level of the tracking software routine at step 2612.

Figure 13:
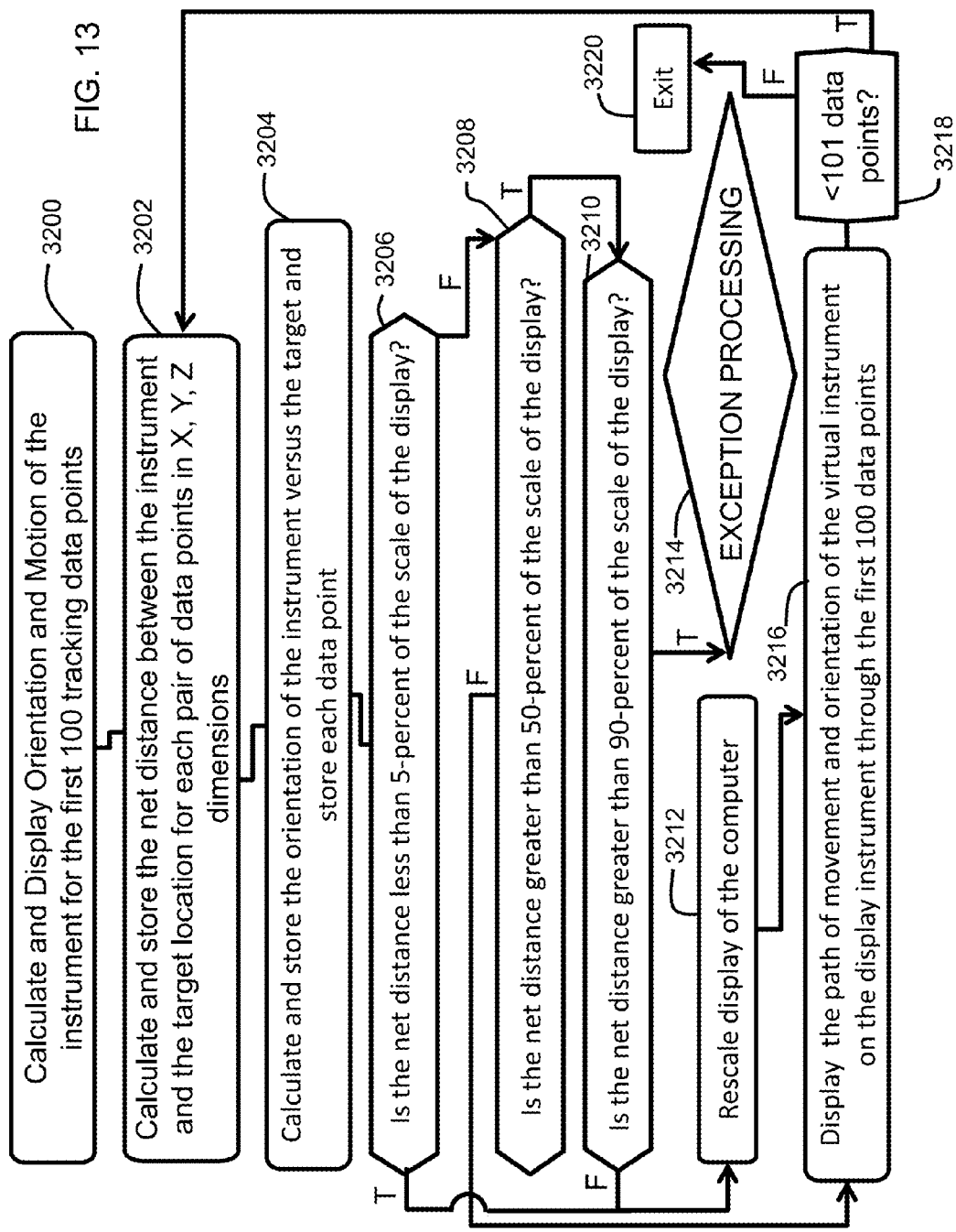
FIG. 13 illustrates a simplified example of a flow chart of the steps performed by a computer to analyze and display the initial 100 movements and changes in orientation of an example embodiment of the motion and orientation sensing module or device.

FIG. 13 is a simplified example flow chart of the steps performed by a computer to analyze and display the initial 100 movements and changes in orientation of an example embodiment of the motion and orientation sensing module or device.

In step 3200 control is transferred to the software routine that performs the necessary actions to analyze and display the first 100 data points defining the movement, location, and orientation of an example probe, tool, instrument, or alignment jigs or cutting blocks, or similar apparatus.

In step 3202 the distance between the active end of the instrument and the target location is calculated by the computer for each sample data point and stored in the distance array. If a second, or marker, example motion and orientation sensing device is positioned to track any change in location or orientation of the target, the location data may previously have been adjusted for any changes in the location of the target before the real-time display is updated.

In step 3204 the computer calculates and stores the difference of orientation between the active end of the instrument and the target orientation in the orientation array. If a second, or marker, example motion and orientation sensing device is positioned to track any change in orientation of the target, the orientation data may previously have been adjusted for any changes in the orientation of the target before the real-time display is updated.

In step 3206 if the net distance less than 5-percent of the scale of the display the display can be re-scaled to improve the visibility of the relative locations and orientations of the instrument and the target.

In step 3208 if the net distance greater than 50-percent of the scale of the display the display can be re-scaled to improve the visibility of the relative locations and orientations of the instrument and the target.

In step 3210 if the net distance greater than 90-percent of the maximum scale of the display an exception condition may exist and exception processing may be required.

In step 3212 the computer software rescales the real-time display to assure effective visibility of the movement and changes in orientation of the motion and orientation sensing module or device whenever the net distance is less than 5-percent or greater than 50-percent of the scale of the display.

In step 3214 whenever the distance is greater than 90-percent of the maximum scale of the display or an exception condition is detected, control is passed to the Exception Processing routine 3500.

In step 3216 the computer displays the trajectory of the motion and orientation of the active end of the instrument with respect to the target location and orientation for each of the first 100 data points.

In step 3218 the tracking software running on the computer checks if 100 data samples have been processed. If equal to or greater than 100 data points the computer returns control to the top level of the tracking software at step 2614.

Figure 14:
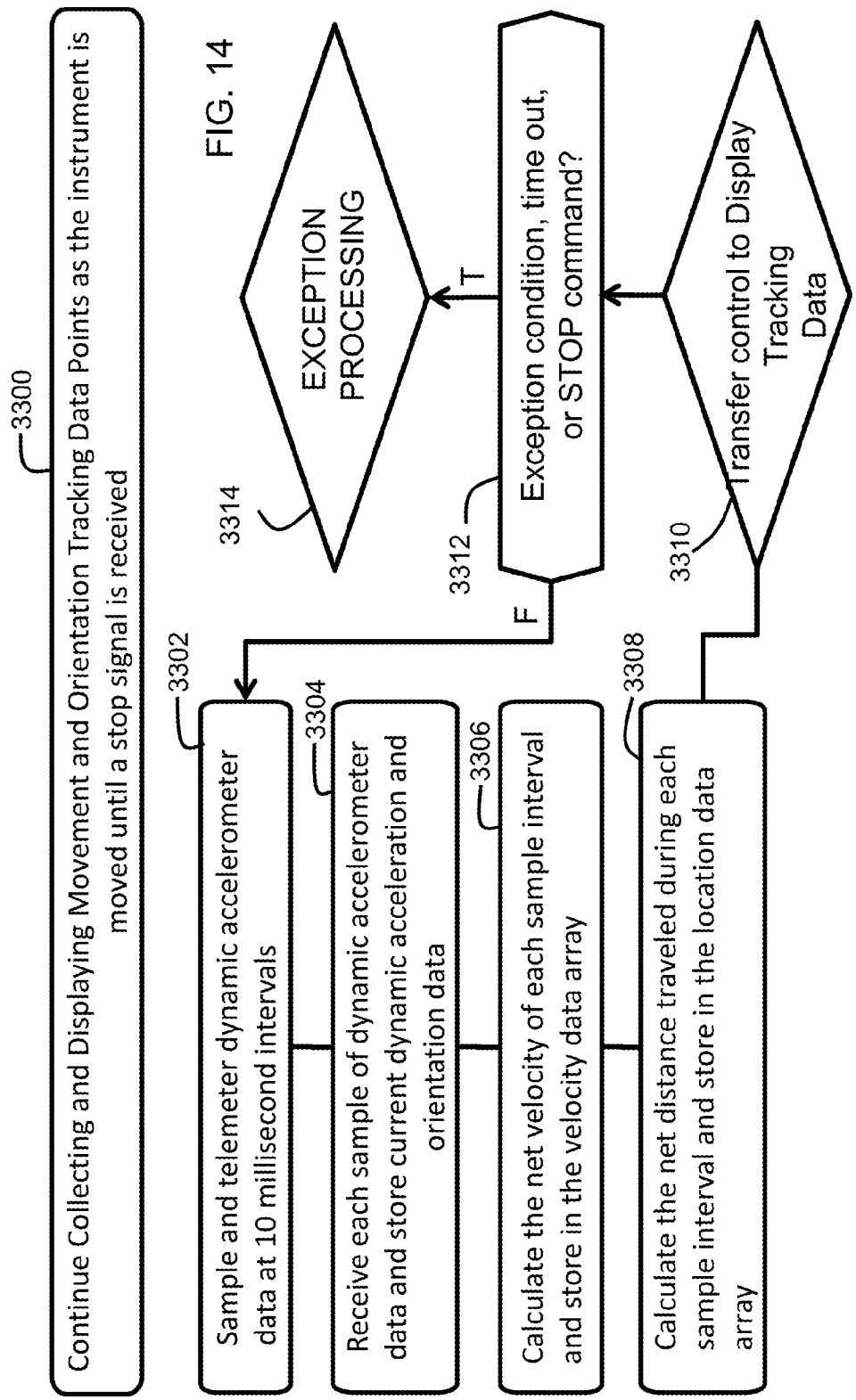
FIG. 14 illustrates a simplified example of a flow chart of the steps performed by a computer to analyze each additional movement and change in orientation of an example embodiment of the motion and orientation sensing module or device.

FIG. 14 illustrates a simplified example flow chart of the steps performed by each motion and orientation sensing module or device in conjunction with the computer to analyze each additional movement and change in orientation beyond the first 100 tracking data samples of an instrument, probe, instrument, or equivalent equipment.

In step 3300 control is transferred to the software routine that performs the necessary actions to collect and display all remaining data points defining the movement, location, and orientation of an example probe, tool, instrument, or alignment jigs or cutting blocks, or similar apparatus with respect to the target location and orientation in real time.

In step 3302 the motion and orientation sensing module or device continues to sample the dynamic acceleration data every 10 milliseconds throughout the tracking procedure and transmits the data to the telemetry receiver connected to the computer. If a second, or marker, example motion and orientation sensing device is positioned to track any change in location or orientation of the target, the orientation and dynamic acceleration data from that device is also sampled every 10 milliseconds. The data from the tracking device is adjusted by the data from the marker device to account for any changes in the orientation and location of the target. The adjusted data is transmitted to the telemetry receiver connected to the computer.

In step 3304 the orientation and dynamic acceleration data for all three Cartesian axes with respect to the zenith and tangents to the surface of the earth from all three accelerometers is analyzed by the computer for real-time display. The adjusted data is stored in the orientation and acceleration data arrays.

In step 3306 the data defining the net average velocity along each Cartesian axis is calculated for the duration of each sample interval and stored in the velocity data array.

In step 3308 the data defining the net change in distance traveled along each Cartesian axis during each sample interval is calculated and stored in the location data array.

In step 3312 control is passed to the Display Tracking Data routine 3400.

In step 3314 when control returns from the Display Tracking Date routine 3400, the software examines the telemetry data to determine if a STOP command has been received, an exception condition detected, or the time without receiving data from the telemetry receiver has been exceeded.

In step 3316 whenever an exception condition is detected, a timeout condition occurs, or the STOP command is received, control is passed to the Exception Processing routine 3500. If no exception condition or Stop command is detected, control is transferred to step 3312 and data collection operations are continued.

Figure 15:
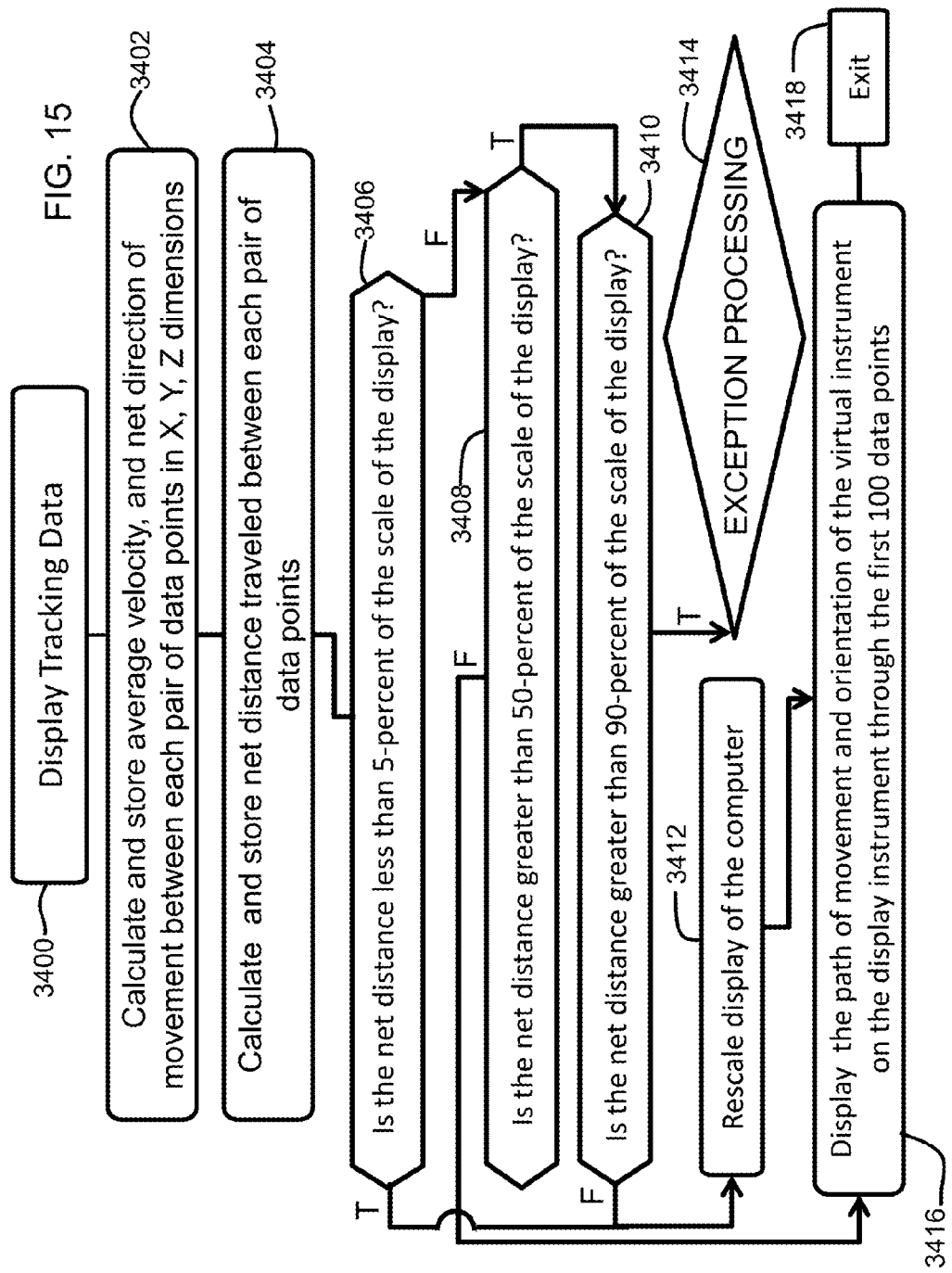
FIG. 15 illustrates a simplified example of a flow chart of the steps performed by a computer to display each additional movement and change in orientation of an example embodiment of the motion and orientation sensing module or device.

FIG. 15 illustrates a simplified example flow chart of the steps performed by a computer to display each additional movement and change in orientation of an example embodiment of the motion and orientation sensing module or device. If a second, or marker, example motion and orientation sensing device is positioned to track any change in location or orientation of the target, the tracking data can be adjusted to account for any movement or change in orientation of the target.

In step 3400 control is transferred to the software routine that performs the necessary actions to display all remaining data points defining the movement, location, and orientation of an example probe, tool, instrument, or alignment jigs or cutting blocks, or similar apparatus.

In step 3402 the computer calculates and stores the average velocity, and net direction of movement between each pair of data points in the velocity array.

In step 3404 the computer calculates and stores the net distance traveled between each pair of data points in the location array.

In step 3406 if the net distance less than 5-percent of the scale of the display the display is rescaled to improve the visibility of the relative locations and orientations of the instrument and the target.

In step 3408 if the net distance greater than 50-percent of the scale of the display the display is rescaled to improve the visibility of the relative locations and orientations of the instrument and the target.

In step 3410 if the net distance greater than 90-percent of the maximum scale of the display an exception condition may exist and exception processing may be required.

In step 3412 the computer software rescales the real-time display to assure effective visibility of the movement and changes in orientation of the motion and orientation sensing module or device whenever the net distance is less than 5-percent or greater than 50-percent of the scale of the display.

In step 3414 whenever the distance is greater than 90-percent of the maximum scale of the display or an exception condition is detected, control is passed to the Exception Processing 3500 routine.

In step 3416 the distance and differences in orientation of the instrument with respect to the target location and orientation is plotted on the display screen in real time.

In step 3418 the computer returns control to Continue Collecting and Displaying Movement and Orientation Tracking Data at step 3312.

Figure 16:
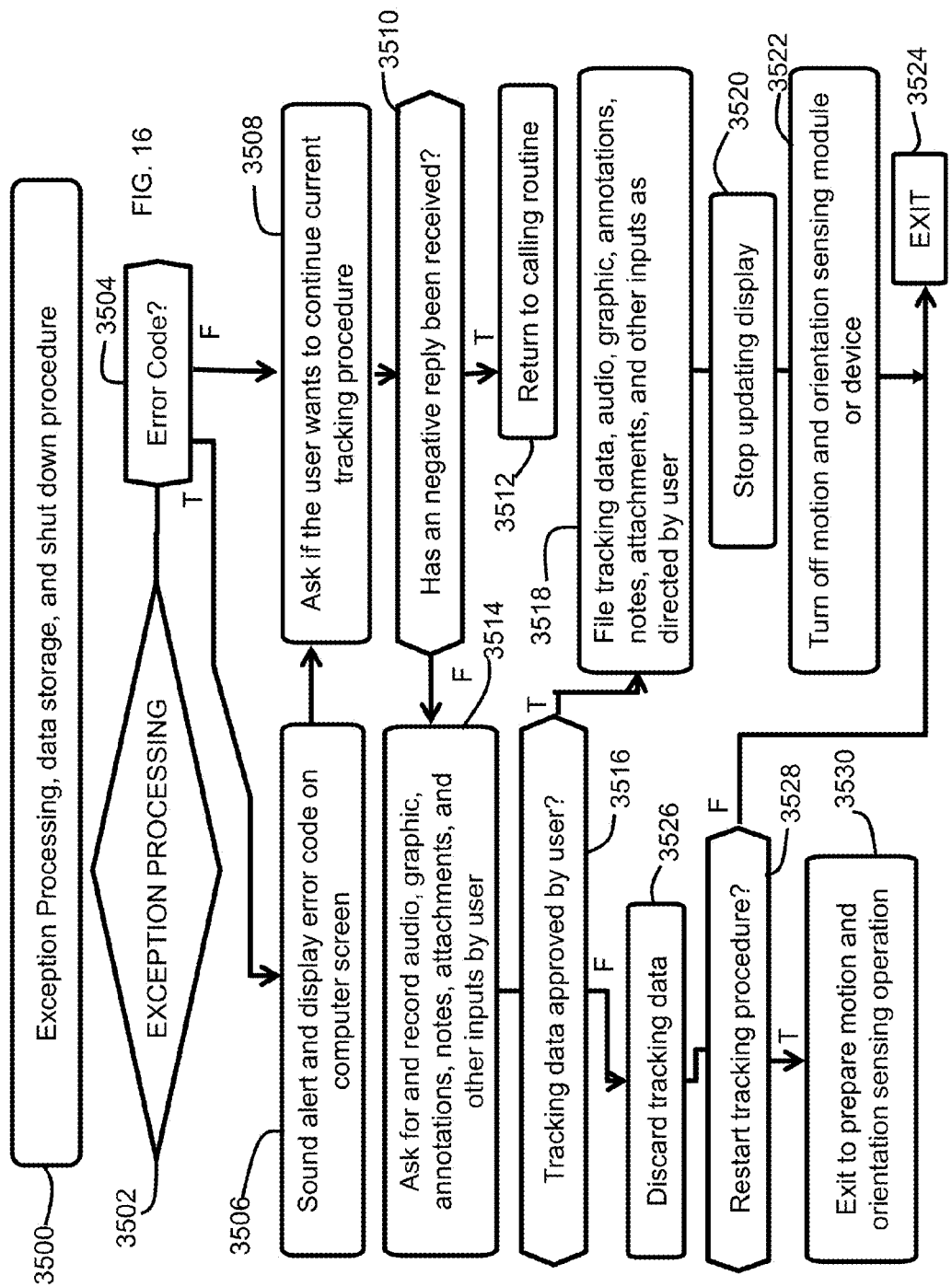
FIG. 16 illustrates a simplified example of a flow chart of the steps performed by a computer to process exception conditions and automatically trigger the shutdown procedure if that becomes necessary to protect the integrity of the tracking procedure while maintaining data integrity.

FIG. 16 is a simplified example flow chart of the steps performed by a computer to process exception conditions and automatically trigger the shutdown procedure if that becomes necessary to protect the integrity of the tracking procedure while maintaining data integrity. A simplified example flow chart is illustrated of the steps performed by a computer to process time-outs, exception conditions, or STOP commands. This routine maintains the integrity of the data while completing the capture and storage of unprocessed tracking data if it is valid. The tracking software is shut down if that becomes necessary to assure the integrity of the tracking procedure.

In step 3500 control is transferred to the software routine that performs the necessary actions to process exception conditions, restart the tracking procedure, or perform an orderly shutdown of the tracking procedure depending on codes included in the call to this routine.

In step 3502 execution of other software routines is suspended while exception processing is performed.

In step 3504 the computer checks for the presence of any error codes.

In step 3506 if an error code is active, the computer sounds an alert and displays the error code or codes on the display screen.

In step 3508 the computer places a question on the display screen asking the user if the current tracking procedure is to be terminated.

In step 3510 if the answer is 'no' control will be returned to the calling routine.

In step 3512 control is returned to the calling routine so collection, processing, and display of the distance and difference in orientation between the tracking motion and orientation sensing module or device and the target can continue.

In step 3514 if the answer is not 'no' or there is no answer, the computer displays a request for, and records, audio, graphic, annotations, notes, attachments, and other inputs the user wants appended to the data records of the current tracking procedure.

In step 3516 the computer places a question on the display screen asking the user if the current tracking data is approved to be added to the record of the current tracking procedure.

In step 3518 if the user approves the current tracking data, all associated data records, audio files, graphic files, annotations, notes, attachments, and other inputs are stored within the record of the current tracking procedure as the first step in the shutdown procedure.

In step 3520 the shutdown procedure continues and the computer ceases to update the display.

In step 3522 the user is reminded to turn off each motion and orientation sensing module or device.

In step 3524 execution of the motion and Orientation Tracking Software Program 2600 is terminated and the shutdown procedure is complete.

In step 3526 if the current tracking data is not approved, all current data records are deleted.

In step 3528 the computer places a question on the display screen asking the user if the current tracking procedure is to be restarted. If not, Execution of the motion and Orientation Tracking Software Program 2600 is terminated without saving any of the tracking data or any other records.

In step 3530 if the user directs the software to restart the tracking procedure, control is transferred to the routine for Prepare Motion and Orientation Sensing operation 2700 and the tracking process is re-started.

Figure 17:
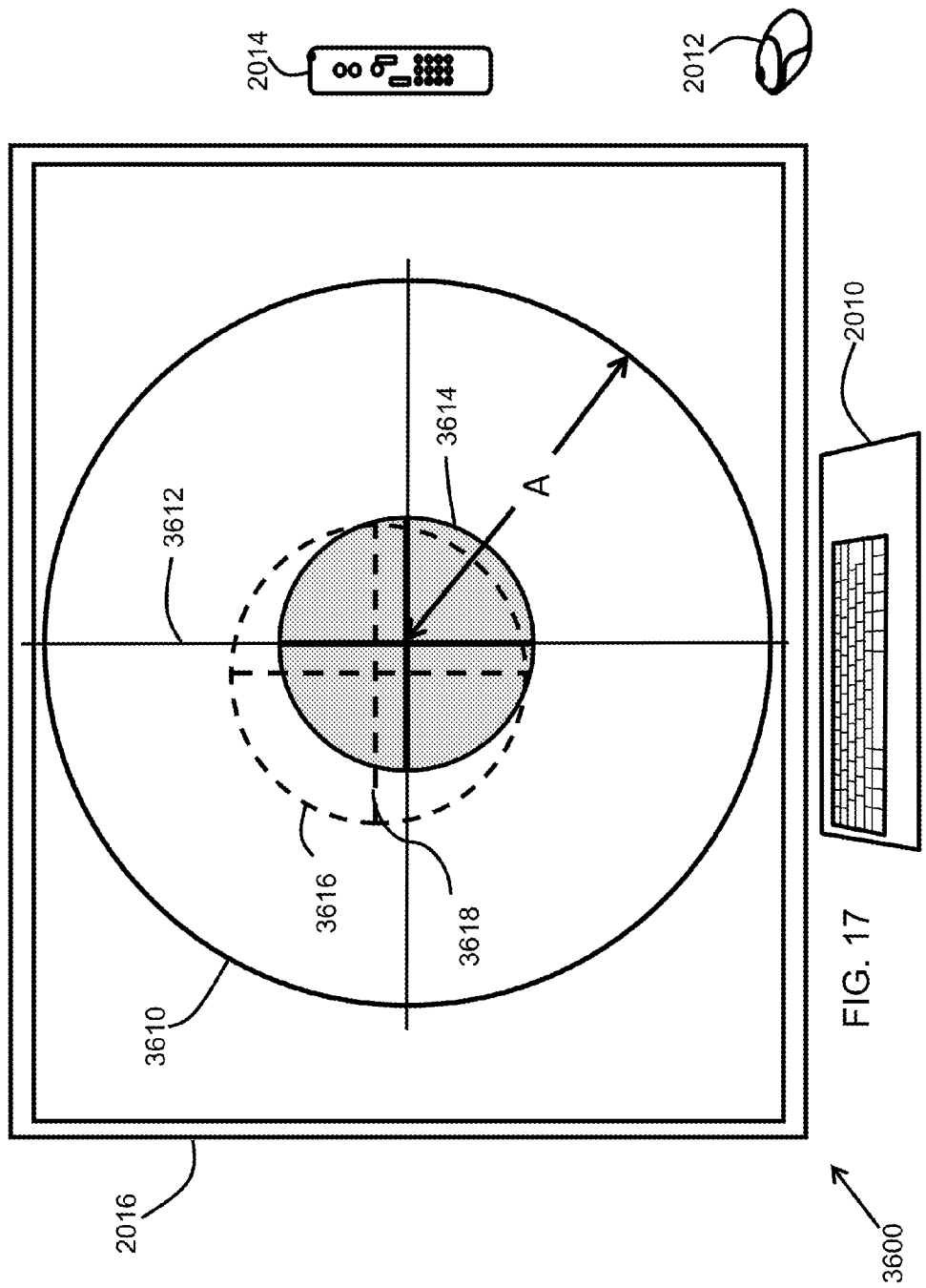
FIG. 17 illustrates a simplified example of an initial computer display screen that can be used to guide the movement and orientation of an instrument having an example embodiment of a motion and orientation sensing module or device.

FIG. 17 is a simplified example of an initial computer display screen that may be used to guide the movement and orientation of an instrument having an example embodiment of a motion and orientation sensing module or device. FIG. 17 illustrates 3600 a simplified example of an initial image on a computer display screen 2016 that may be used to guide the movement and orientation of an instrument having an example embodiment of the motion and orientation sensing module or device. With the reception of the initial telemetry data packet computer 2014, having computer keyboard 2010 and computer mouse 2012, defines the initial position of the active end of the example medical instrument as the target location. The target orientation is equal to the initial tilt and yaw of the instrument with respect to all three Cartesian axes aligned with the zenith and tangents to the surface of the earth. The representation of the physical location and orientation and target location and orientation is displayed on computer display screen 2016. The target position and alignment image consists of an outer ring of a bulls-eye image 3610, with radius A representing the scale of the bulls-eye in millimeters, an inner ring of the bulls-eye image 3614, and crosshairs 3612 within the bulls-eye image 3610 on computer display screen 2016. The initial representation of the active end of the instrument have an example motion and orientation sensing module or device is an image of a virtual circumference 3616 centered within the inner ring 3614 of the bulls-eye and likewise the Image of virtual crosshairs 3618 coinciding with the central portion of the image of the crosshairs 3612 of the target bulls-eye.

Figure 18:
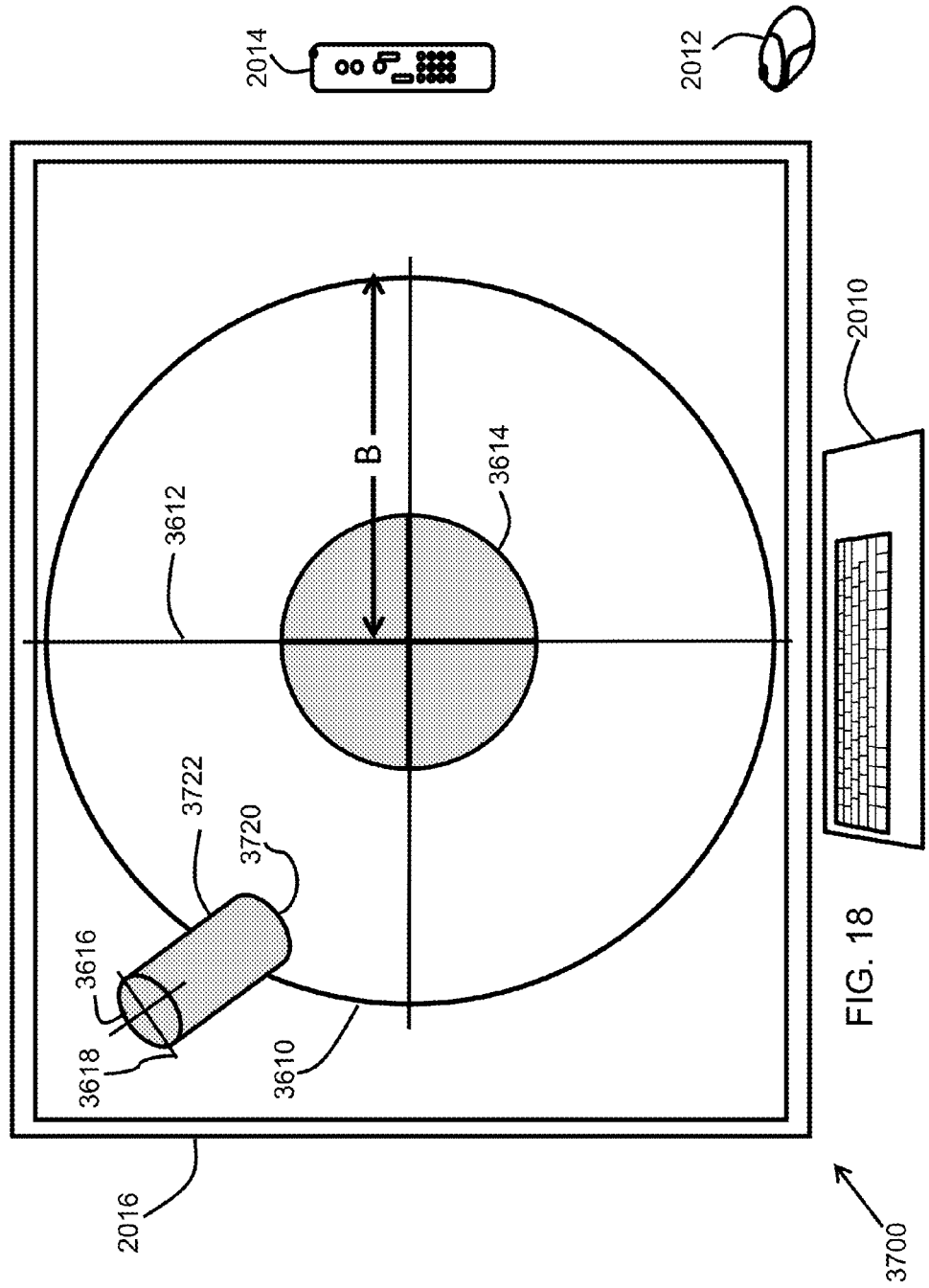
FIG. 18 illustrates a simplified example of a computer display screen illustrating the position and location of an instrument having an example embodiment of a motion and orientation sensing module or device as it is starting to approach the pre-defined target location and orientation.

FIG. 18 is a simplified example of a computer display screen illustrating the position and location of an instrument having an example embodiment of a motion and orientation sensing module or device as it is starting to approach the pre-defined target location and orientation. FIG. 18 illustrates 3700 a simplified example of a tracking image on a computer display illustrating the position and orientation of an instrument having an example embodiment of the motion and orientation sensing module or device attached, affixed, embedded, or integrated within it. The computer 2014, having computer keyboard 2010 and computer mouse 2012, presents images on display 2016 representing the orientation, movement, and location of an example instrument with respect to the target location and orientation. The target position and alignment image consists of an outer ring of a bulls-eye image 3610, with radius B representing the scale of the bulls-eye in decimeters, an inner ring of the bulls-eye image 3614, and crosshairs 3612 within the bulls-eye image 3610 on computer display screen 2016. In this figure the instrument is positioned at a distance from the physical target. Computer display 2016 is updated in real time whenever the user moves the example instrument. To assure alignment in all three dimensions, the image of the example instrument is represented as a cylinder 3722 with crosshairs 3618 circumferences 3616, 3720 at both ends. The degree of alignment of both circumferences 3616, 3720 of the ends of cylinder 3722 represent orientation in the third dimension and may be easier to correlate with physical space than the usual two dimensional representation of three dimension graphs. This example representational of three dimensional spaces may be readily presented on 3D displays.

The heading of a motion and orientation sensing module or device is measured and tracked by two tri-axial accelerometers positioned at the longitudinal ends of an example motion and orientation sensing module or device. The tilt of the forward tri-axial accelerometer with respect to the orientation of the physical target is represented by the orientation of the image of the virtual crosshairs 3618 with respect to target crosshairs 3612 on display screen 2016. The second integral of the algebraic sum of the acceleration in all a three Cartesian axes of the forward tri-axial accelerometer determines the distance between the active edge of the example instrument and the target. The differences between the calculated locations of each end of the example motion and orientation sensing module or device along its longitudinal axis defines its relative heading, or the yaw required to align longitudinal axis of the example motion and orientation sensing module or device in the X, Y plane. The estimate of the difference in location determines the relative size and location of the image 3616, 3618, 3720, 3722 of the instrument with respect to the image of the inner circle of the target location 3614.

As the example instrument approaches the target location the magnification of the display may be automatically increased to facilitate more precise movement and orientation of the example instrument as it gets closer to the target location.

Figure 19:
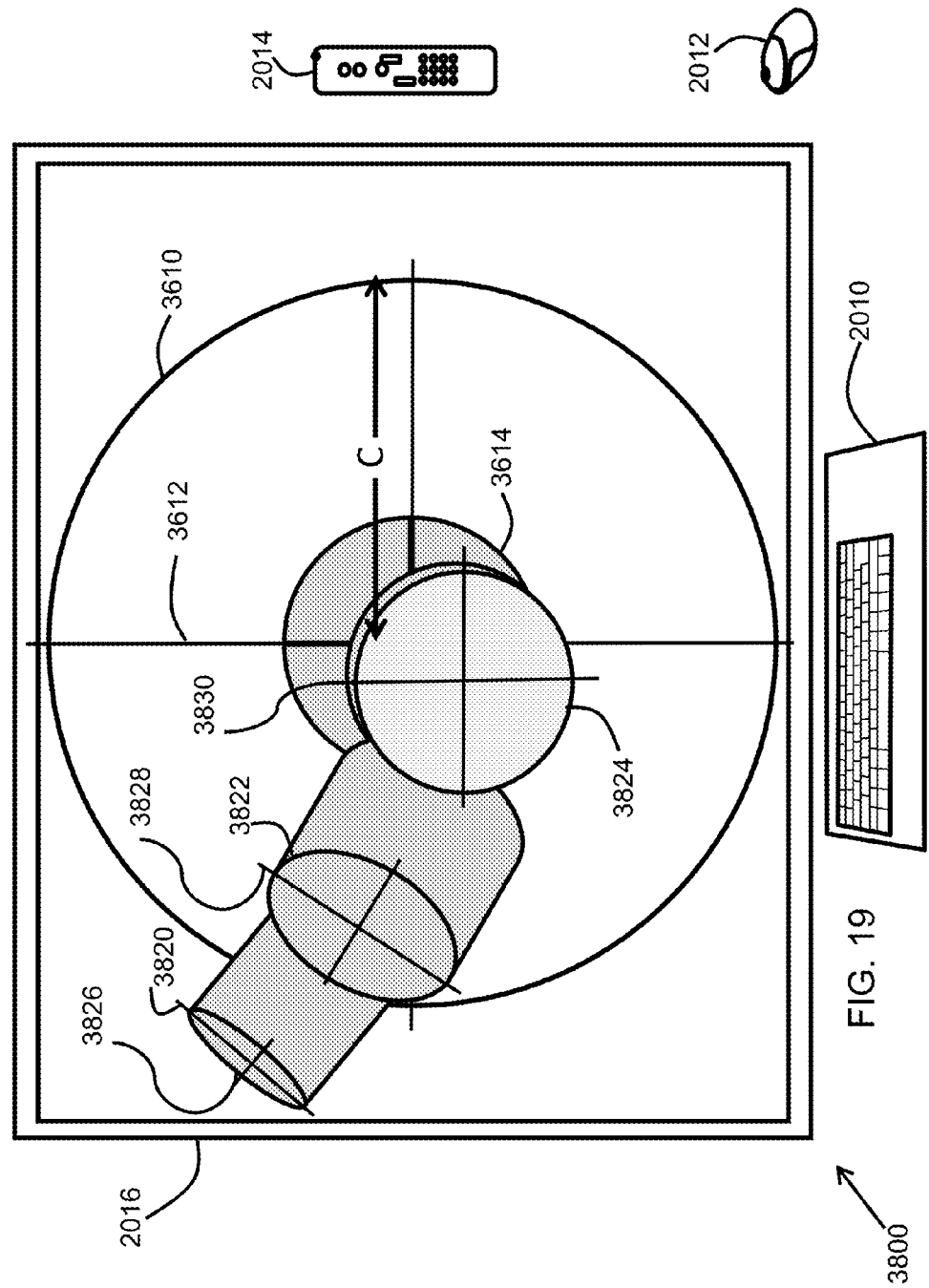
FIG. 19 illustrates a simplified example of a computer display screen illustrating changes in the display as an instrument having an example embodiment of a motion and orientation sensing module or device is moved towards the target location and orientation.

FIG. 19 is a simplified example of a computer display screen illustrating changes in the display as an instrument having an example embodiment of a motion and orientation sensing module or device is moved towards the target location and orientation. FIG. 19 illustrates 3800 a simplified example of a computer display 2016 illustrating the movement of an instrument having an example embodiment of the motion and orientation sensing module or device attached, affixed, embedded, or integrated within it as it moves towards a physical target. Computer 2014, having computer keyboard 2010 and computer mouse 2012, processes all orientation and movement data with respect to the initial location and orientation of the example instrument. Computer display 2016 is updated in real time whenever the user moves the example instrument with respect to the target orientation and orientation. The target position and alignment image consists of an outer ring of a bulls-eye image 3610, with radius C representing the scale of the bulls-eye in centimeters, an inner ring of the bulls-eye image 3614, and crosshairs 3612 within the bulls-eye image 3610 on computer display screen 2016. This movement is illustrated as multiple images of virtual cylinders on computer display 2016. The three cylinders 3820, 3822, 3824 illustrated in this figure represent the same physical device with each image representing its location and orientation as it is moved towards the target location and orientation.

The target location and orientation is represented by the image of a bulls-eye with crosshairs 3612 and circles 3610, 3614. To assure alignment in all three dimensions, the representation of the example instrument is represented by images of virtual cylinders 3820, 3822, and 3824 with images of virtual crosshairs 3826, 3828, and 3830. The degree of alignment of the virtual crosshairs 3826, 3828, 3830 with bulls-eye crosshairs 3612 illustrates the relative orientation of the instrument being tracked in two axes. The degree of alignment of the ends of the images of each of the virtual cylinders 3820, 3822, 3824 represents the relative orientation in the third dimension. The degree of alignment and relative size of the circumferences of virtual cylinders 3820, 3822, and 3824 with the inner bulls-eye ring 3614 illustrates the relative location of the instrument being tracked with respect to the target.

As the example instrument approaches the target location the magnification of the display may continue to automatically increase to facilitate more precise movement and orientation of the example instrument as it gets closer to the target location.

Figure 20:
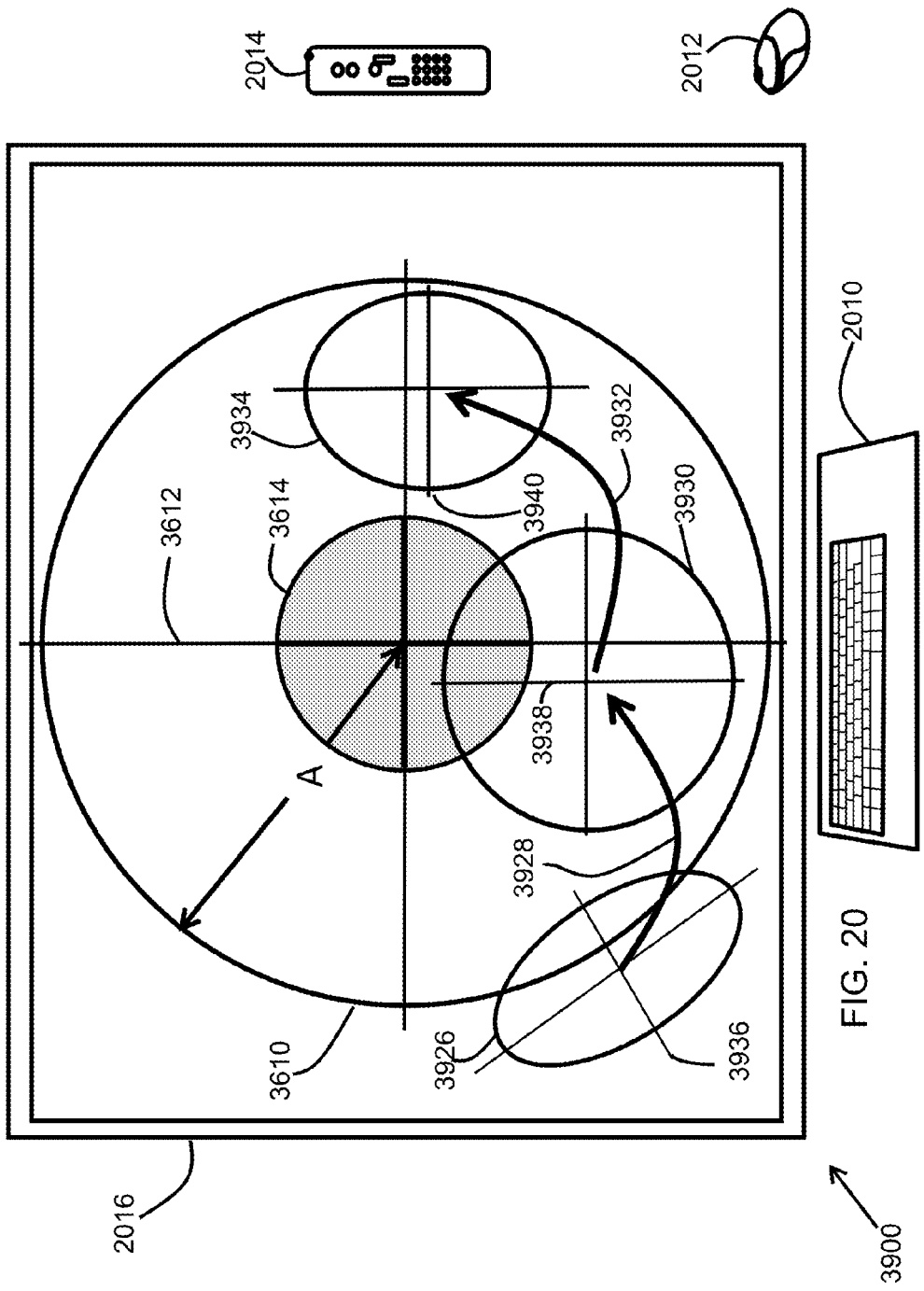
FIG. 20 illustrates a simplified example of a computer display screen illustrating changes in the display as an instrument having an example embodiment of a motion and orientation sensing module or device approaches the target location and orientation.

FIG. 20 is a simplified example of a computer display screen illustrating changes in the display as an instrument having an example embodiment of a motion and orientation sensing module or device approaches the target location and orientation. FIG. 20 illustrates 3900 a simplified example of a computer display 2016 illustrating the movement of an instrument having an example embodiment of the motion and orientation sensing module or device attached, affixed, embedded, or integrated within it as it moves towards a physical target. Computer display 2016 is updated whenever the user moves the example instrument with respect to the target orientation and orientation. Computer 2014, having computer keyboard 2010 and computer mouse 2012, processes all orientation and movement data with respect to the initial location and orientation of the example instrument and updates computer display 2016 in real time as the motion and orientation sensing module or device is moved. The target position and alignment image consists of an outer ring of a bulls-eye image 3610, with radius A representing the scale of the bulls-eye in millimeters, an inner ring of the bulls-eye image 3614, and crosshairs 3612 within the bulls-eye image 3610 on computer display screen 2016.

The three virtual circumferences 3926, 3930, 3934, with images of virtual crosshairs 3936, 3938, 3940 in this figure represent the same physical device with each image representing its location and orientation as it is moved towards the target location and orientation. This movement is illustrated by separating these multiple images representing the instrument being tracked by arrows 3928, and 3932. The target location and orientation is represented by the image of a bulls-eye with crosshairs 3612 and circles 3610, 3614. The degree of alignment of the virtual circumferences 3926, 3930, 3934 with the inner bulls-eye ring 3614 illustrates the relative location of the instrument being tracked with respect to the target. The degree of alignment of the virtual crosshairs 3936, 3938, 3940 with bulls-eye crosshairs 3612 illustrates the relative orientation of the instrument being tracked with respect to the target.

As the example instrument approaches the target location the magnification of the display may continue to automatically increase to facilitate more precise movement and orientation of the example instrument as it gets closer to the target location.

Figure 21:
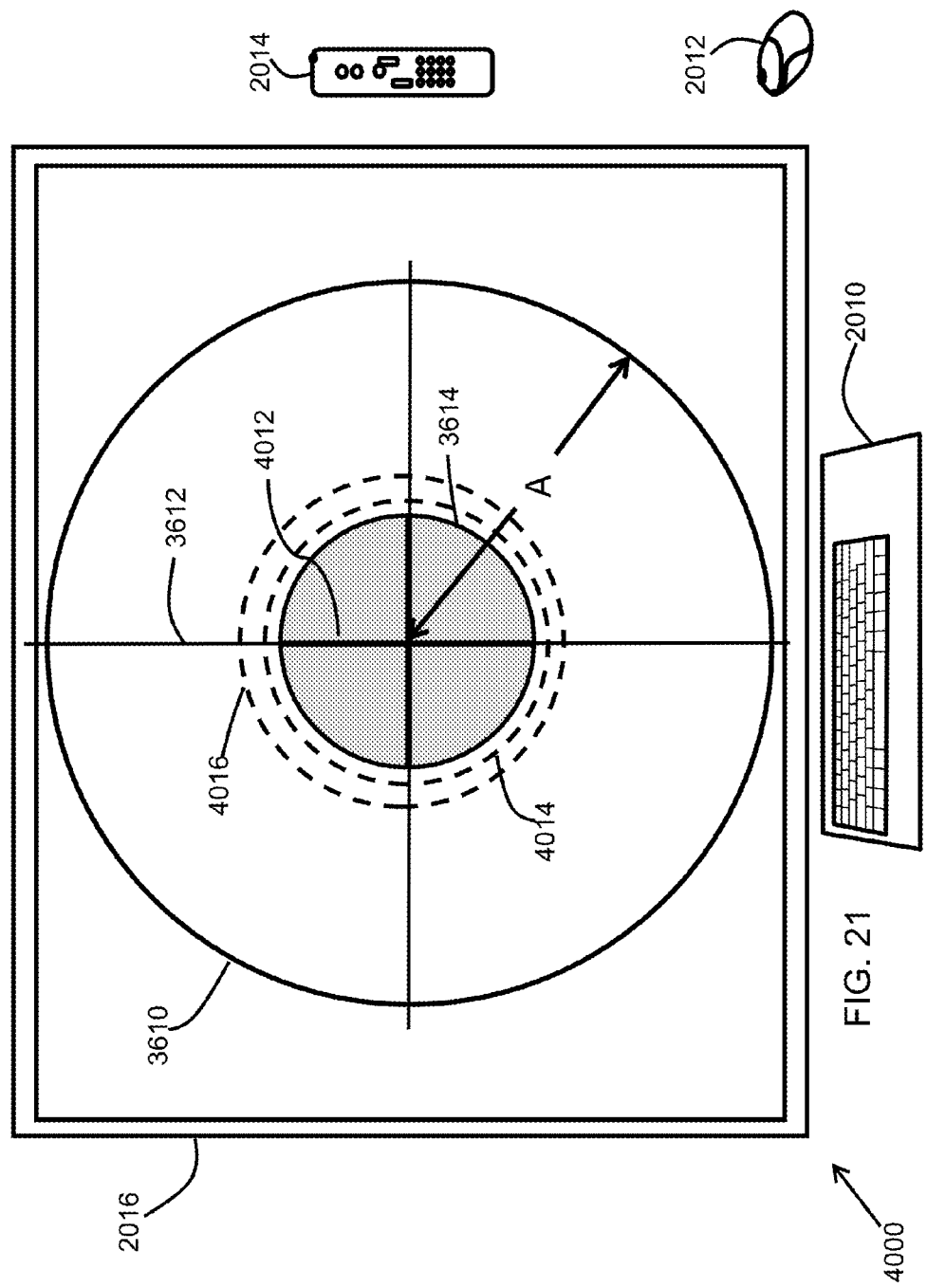
FIG. 21 illustrates a simplified example of a computer display screen illustrating the final position and orientation of an instrument having an example embodiment of a motion and orientation sensing module or device precisely aligned with the target location and orientation.

FIG. 21 is a simplified example of a computer display screen illustrating the final position and orientation of an instrument having an example embodiment of a motion and orientation sensing module or device precisely aligned with the target location and orientation. FIG. 21 illustrates 4000 a simplified example of a computer display 2016 illustrating the location and orientation of an instrument having an example embodiment of the motion and orientation sensing module or device attached, affixed, embedded, or integrated within it when it arrives at the target location and is aligned with the target orientation. The target position and alignment image consists of an outer ring of a bulls-eye image 3610, with radius A representing the scale of the bulls-eye in millimeters, an inner ring of the bulls-eye image 3614, and crosshairs 3612 within the bulls-eye image 3610 on computer display screen 2016. Computer 2014, having computer keyboard 2010 and computer mouse 2012, processes all orientation and movement data with respect to the initial location and orientation of the example instrument. In this figure the example instrument is in contact with the physical target, even if the target itself is not visible to the physician. Concentric circles 4014, 4016, representing the virtual circumferences of the longitudinal axis of the example instrument, are centered on a third circle 3614 representing the inner bulls-eye ring of the image of the target location. Virtual crosshairs 4012, representing the orientation of the cross-section of the longitudinal axis of the example instrument, are coincident with crosshairs 3612 representing the orientation of the target location. The combination of these three concentric circles along with the alignment of the crosshairs indicates that the example medical instrument is positioned precisely at the target location and aligned precisely with the target orientation in all three Cartesian coordinates aligned with the zenith and tangents to the surface of the earth.

Figure 22:
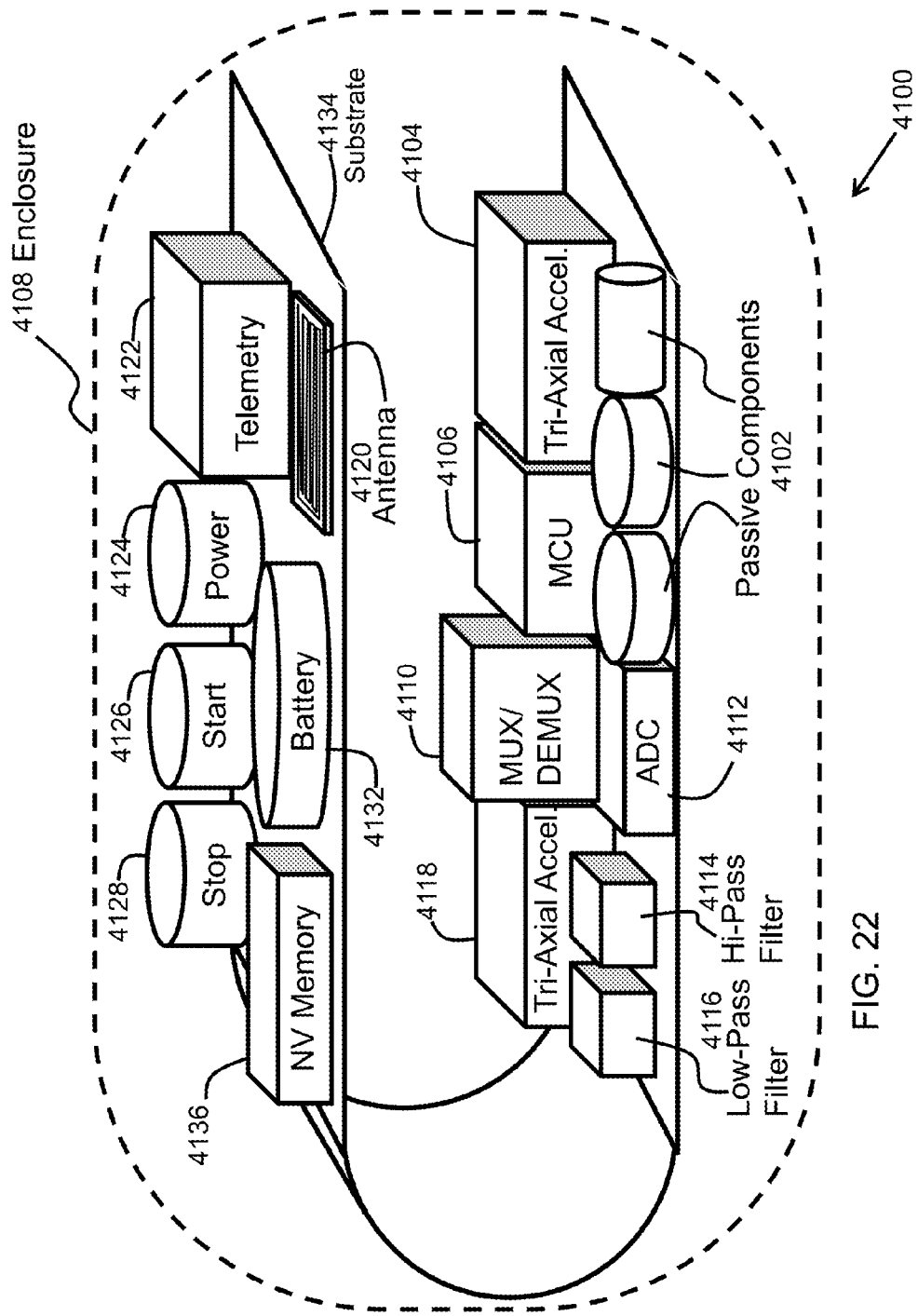
FIG. 22 illustrates a simplified perspective of a cut-away view of an example motion and orientation sensing module or device.

FIG. 22 is a simplified perspective cut-away view of an example motion and orientation sensing module or device. FIG. 22 illustrates 4100 a simplified perspective cut-away view of an example motion and orientation sensing module or device enclosed in encapsulating shell. Enclosure 4108 may be either hermetic or non-hermetic depending on the application. Substrate 4134 provides mechanical support for the internal components of the motion and orientation sensing module or device, as well as electrical interconnect for the electronic circuitry. POWER switch 4124 is used to turn the motion and orientation sensing module or device on and off. START switch 4126 is used to initiate the tracking procedure or restart it if it has been interrupted. STOP switch 4128 is used to pause or terminate the tracking procedure. Battery 4132, or an equivalent energy storage device, provides power for the operation of the electronic circuitry and telemetry transmissions by telemetry transmitter or transceiver 4122 through antenna 4120. Passive components 4102 support the integrated circuits to implement the full electrical schematic. The electrical Non-volatile memory 4136 stores the identification code of the motion and orientation sensing module or device as well as calibration constants, battery voltage, temperature, and other programmable data. Tri-axial accelerometer 4104 detects movement in all three Cartesian axes and tilt with respect to the zenith and tangents to the surface of the earth. It is positioned at one end of the longitudinal axis of the motion and orientation sensing module or device, and tracks the distance between the leading or active edge of a medical instrument and the target. Accelerometer 4104 also tracks the orientation of the cross section of the motion and orientation sensing module or device. MUX/DEMUX 4110 interfaces between the individual sensing elements within the accelerometers to enable their analog outputs to be processed by analog to digital conversion (ADC) circuitry 4112. Hi-pass filter 4114 provides inputs to event detection circuitry. Low-pass filter 4116 limits the bandwidth of analog signals coupled to the analog to digital conversion circuitry 4112 to reduce electrical noise and out-of-band signals. Tri-axial accelerometer 4118 detects movement in all three Cartesian axes and tilt with respect the zenith and tangents to the surface of the earth. It is positioned at the opposite end of the longitudinal axis of the motion and orientation sensing module or device from triaxial accelerometer 4104. Accelerometer 4118 tracks the distance between the trailing edge of an example medical instrument and the target. Micro control unit 4106 controls the operation of the motion and orientation sensing module or device as well as data processing functions performed within it.

Motion and orientation sensing modules and devices having dual accelerometers are not only capable of providing more accurate yaw data, but have an inherent level of redundancy that aids in the confirmation that the instrument is guided accurately to the target position and orientation. This combination of electrical, mechanical, and RF components enables the construction of extremely small, high resolution, low-power, hermetic, wireless motion and orientation sensing devices.

Figure 23:
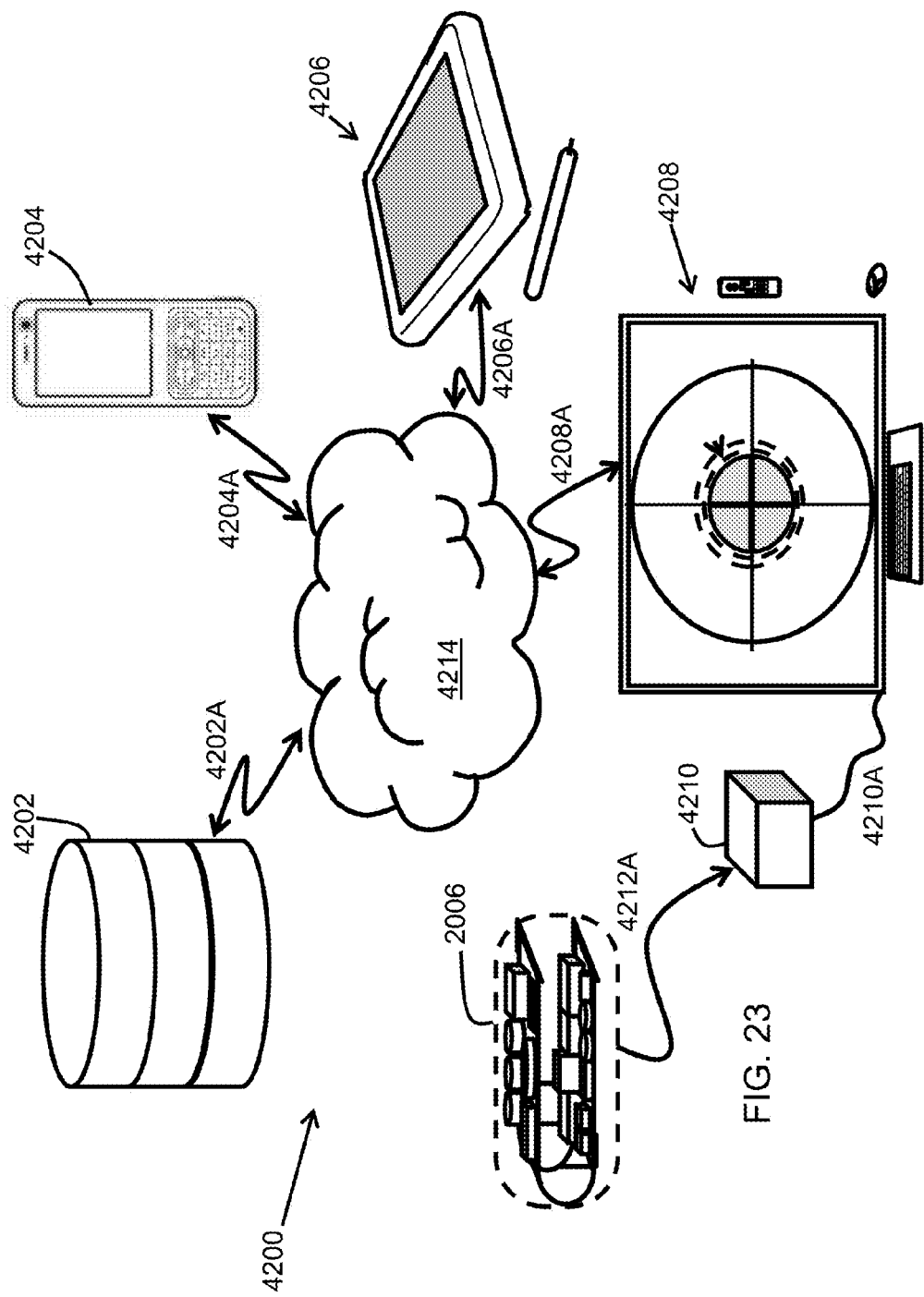
FIG. 23 illustrates a simplified block diagram of an example information technology system and components integrating the data captured by a motion and orientation sensing module or device and displaying its progress in real time.

FIG. 23 is a simplified block diagram 4200 of an example information technology system and components integrating the data captured by a motion and orientation sensing module or device and displaying its progress in real time. This network of devices enables the real-time acquisition and sharing of information to enable more effective decision making as well as collective understanding of medical histories and conditions. The motion and orientation sensing module or device 2006 includes a telemetry transmitter or transceiver. This transmits data 4212A to telemetry receiver 4210 networked or connected 4210A to computer system 4208. Computer system 4208 is also connected online 4208A to internet cloud services 4214. This enables data to be stored within cloud services 4214 within the internet or within dedicated electronic health record databases 4202 that are connected 4202A to the internet. It also facilitates accessing data through other computers and other information devices such as smartphones 4204 that are wirelessly connected 4204A to the internet and tablets 4206 that are also connected wirelessly 4206A to the internet. This network and collection of services and data peripherals enable patient data to be shared worldwide among appropriate physicians and healthcare facilities as needed to assure patient care and safety.

FIG. 24 illustrates a simplified block diagram 4300 of the basic construction of a generic accelerometer. The general sensing structure of most accelerometers is a proof mass 4306 that is restrained by some form of resistive mechanical supports 4302 such as springs or flexible supports having anchor points 4304. The proof mass 4306 and resilient mechanical supports 4302 may be fabricated with micromachining processes in combination with standard integrated circuit fabrication processes. At rest or under constant velocity the electrical sensing element 4310 maintains a constant level of capacitance, resistance, charge, voltage, or current. Electrical signals output by electrical sensing element 4310 may be converted into digital signals by additional circuitry integrated within the accelerometer integrated circuit or connected to it. This digital data may be used to track, analyze, store, and display the movement and changes in orientation of an accelerometer.

FIG. 25 illustrates a simplified block diagram 4400 of the basic construction of a generic accelerometer subjected to acceleration vector 4408. The acceleration may be constant, such as acceleration due to the force of gravity, or variable. The general sensing structure of most accelerometers is a proof mass 4306 that is restrained by some form of resistive mechanical supports 4302 such as springs or elastic supports having anchor points 4304. The proof mass 4306 and resilient mechanical supports 4302 may be fabricated with micromachining processes in combination with standard integrated circuit fabrication processes. Vectors of acceleration 4408 normal to the support axis cause the proof mass 4306 to move relative to the anchor points 4304. The movement of the proof mass 4306 displaces portions of electrical sensing element 4310 changing its electrical parameters or outputs. These parameters may include capacitance or resistance, or the output of charge, voltage, or current. The acceleration due to gravity may also hold the proof mass 4306 in a position that is electrically detectable. This enables the detection of tilt with respect to the earth's surface. Electrical signals output by electrical sensing element 4310 may be converted into digital signals by additional circuitry integrated within the accelerometer integrated circuit or connected to it. This digital data may be used to track the movement and changes in orientation of the accelerometer.

Figure 26:
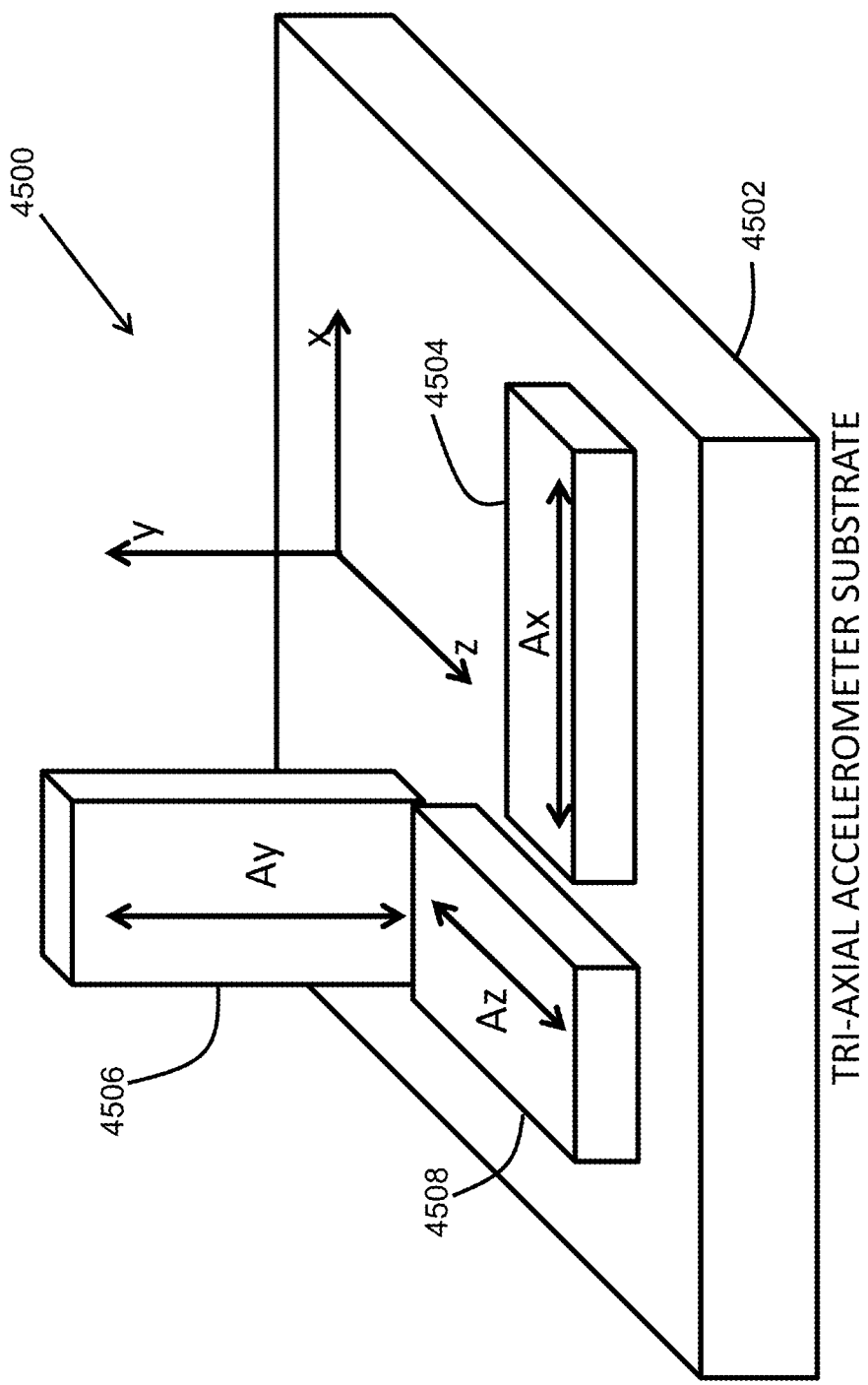
FIG. 26 illustrates a simplified block diagram of the orientation of generic accelerometers within a tri-axial accelerometer.

FIG. 26 illustrates a simplified block diagram 4500 of the orientation of generic accelerometers within a tri-axial accelerometer die, chip, integrated circuit, hybrid circuit, or electronic module. Most MEMS accelerometers operate in-plane, that is, they are designed to be sensitive only to a direction in the plane of the die. By integrating two devices 4504, 4508 at right angles on a single die a two-axis accelerometer can be fabricated. By adding an additional out-of-plane device 4506 all three Cartesian axes can be detected and quantized with a single triaxial accelerometer device. The out-of-plane device 4506 may be fabricated with additional MEMS processes integrating all three accelerometers within the same integrated circuit die or chip. One determinate of the accuracy of a tri-axial accelerometer is the precision of the relative orientation of each of the three acceleration sensing elements. Integration of all three acceleration sensing elements on a single die or chip may result in lower misalignment error than three discrete accelerometers combined within a single package or mounted directly onto a silicon die or chip, PWB, or other substrate 4502.

Figure 27:
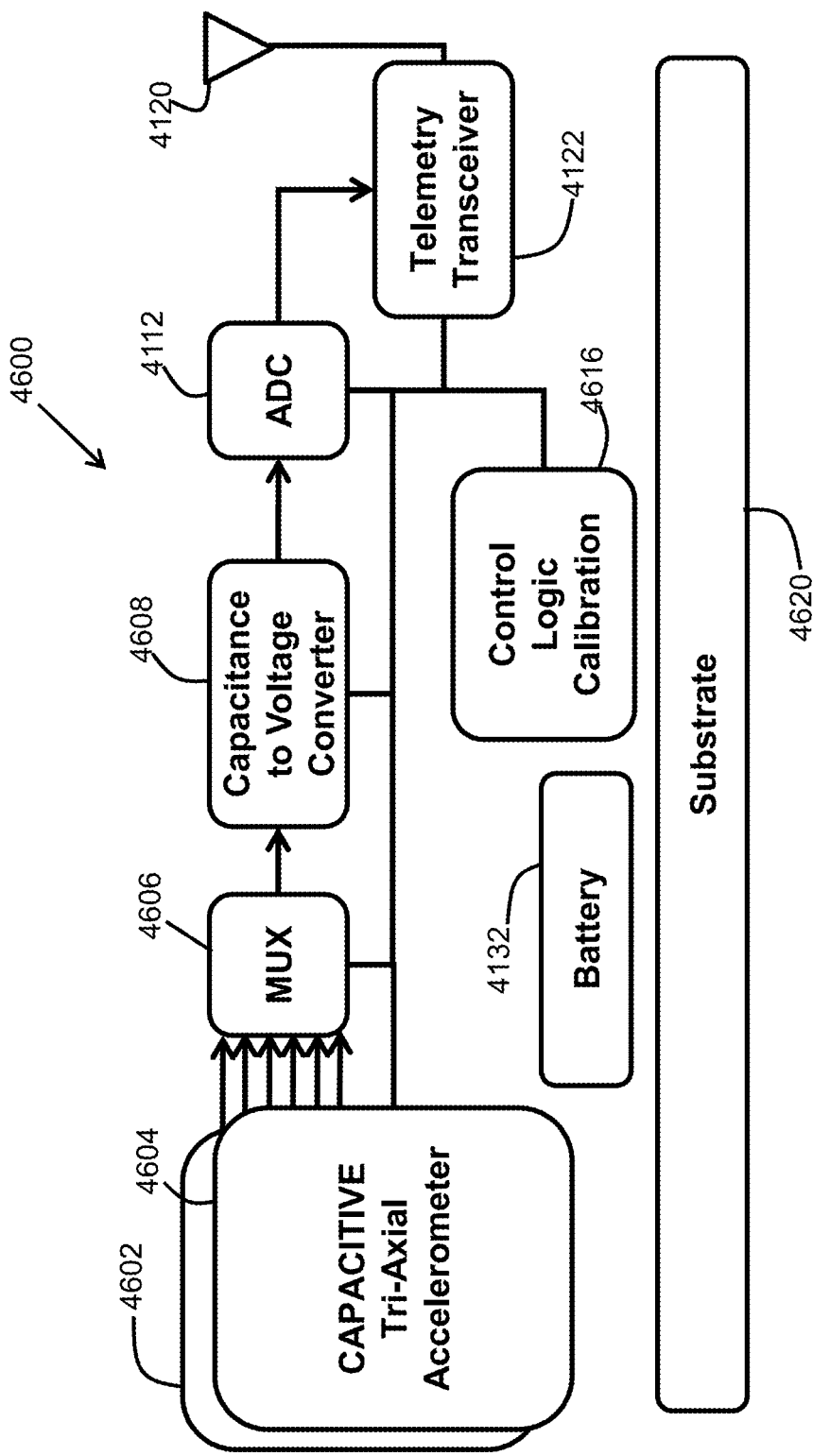
FIG. 27 illustrates a simplified schematic block diagram of an example motion and orientation sensing module or device having tri-axial capacitive accelerometers.

FIG. 27 illustrates a simplified schematic block diagram 4600 of an example motion and orientation sensing module or device having two tri-axial capacitive accelerometers. Capacitive accelerometers fabricated on integrated circuit die are primarily bulk MEMS structures. Capacitive accelerometers have a moveable micromachined feature that acts as one side of a variable capacitor with respect to a fixed structure within the integrated circuit die. Movement of the integrated circuit causes displacement of this moveable structure resulting in a change in the level of capacitance. The change in capacitance produces a change in output frequency or analog voltage that is proportional to the sum of dynamic and static acceleration. Capacitive accelerometers are DC-responding with high sensitivities, narrow bandwidth, and outstanding temperature stability. These devices are well suited for measuring low-frequency vibration, motion, and steady-state acceleration such as gravity.

Two accelerometers 4602, 4604 are positioned at each end of the longitudinal axis of the motion and orientation sensing module or device. The forward tri-axial accelerometer 4604 tracks the movement of the leading edge or active face of an example instrument. This accelerometer 4604 also tracks the orientation of the cross section of the motion and orientation sensing module or device. The trailing accelerometer 4602 tracks the orientation of the longitudinal axis of the motion and orientation module or device. The combination of the two tri-axial accelerometers 4602, 4604 can be used to measure heading and yaw in the X-Y plane with high accuracy. The sensing elements within capacitive tri-axial accelerometers 4602, 4604 generate analog electrical signals whenever the motion and orientation sensing module or device is moved or rotated. These analog signals also have a DC component depending on their orientation with respect to the nadir. The effective number of bits of a capacitive, or a variable capacitance, accelerometer depends on the resolution of changes in capacitance resulting from displacement of the plates of the sensing capacitors within the accelerometer. The combination of the two accelerometers 4602, 4604 assures the motion and orientation sensing module or device can be guided precisely to the target location and orientation in all three Cartesian axes with no discrepancies in pitch, roll, or yaw.

Motion and orientation sensing modules and devices having two accelerometers are not only capable of providing more accurate yaw data, but two accelerometers also provide a level of redundancy that aids in the confirmation that an instrument is guided accurately to the target position and orientation. If data generated by the two accelerometers 4602, 4604 contain a discrepancy, the tracking procedure may have been compromised and the user can be alerted to the possibility of an exception condition that needs to be addressed.

Multiplexor (MUX) 4606 interfaces the acceleration sensing elements of accelerometers 4602, 4604 with the input of capacitance to voltage convertor 4608. The analog signals output by the capacitance to voltage conversion circuitry 4608 drive the input of the analog to digital conversion circuitry (ADC) 4112. The digital values output by ADC 4112 are transmitted by telemetry transceiver or transmitter 4122 through antenna 4120. This enables an external computer system or other information technology appliance to receive the radio frequency signal broadcast by the motion and orientation sensing module or device for subsequent processing, storage, and display in real time.

Control logic and calibration circuitry 4616 controls the operation of the electronic components within an example motion and orientation sensing module or device as well as additional data processing required before transmitting data to a computer system. Battery 4132, or an equivalent energy storage device, provides the power to operate the electronic circuitry within the motion and orientation sensing module or device. Substrate 4620 provides mechanical support and electrical interconnect for the electronic components and battery within the example motion and orientation sensing module or device.

The illustrated components and interconnect will enable tracking the movement and orientation of a medical probe, tool, instrument, alignment jig, cutting block, or similar equipment having a motion and orientation sensing module or device, accurately with a high level of precision.

Figure 28:
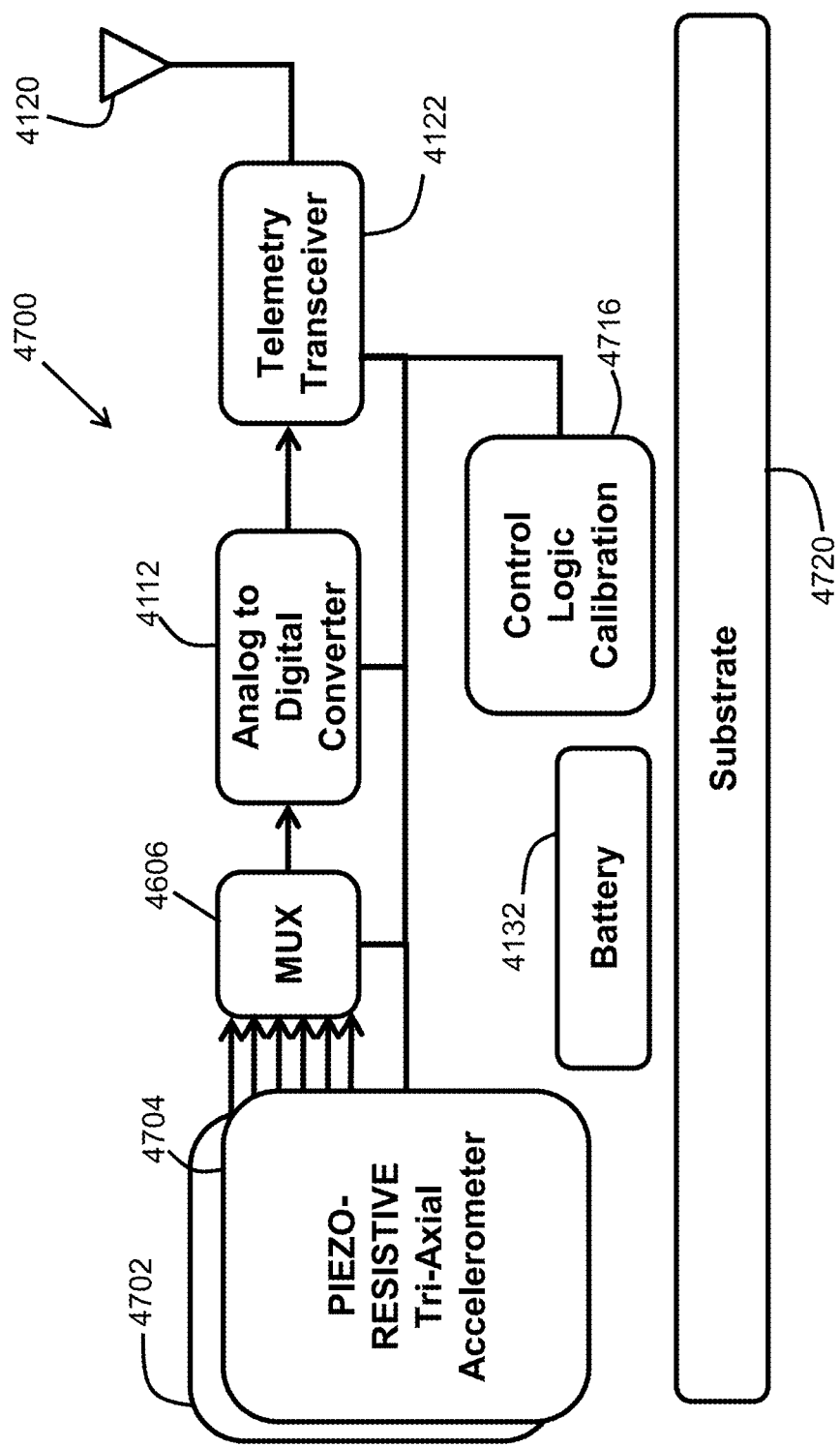
FIG. 28 illustrates a simplified schematic block diagram of an example motion and orientation sensing module or device having tri-axial piezoresistive accelerometers.

FIG. 28 illustrates a simplified schematic block diagram 4700 of an example motion and orientation sensing module or device having two tri-axial piezoresistive or piezoelectric accelerometers. Piezoresistive accelerometers fabricated on integrated circuit die are primarily bulk MEMS structures. Piezoresistive accelerometers have a beam or micromachined feature whose resistance changes as it is flexed by movement of the proof mass. The change in resistance produced by flexing the cantilever produces a change in resistance that is proportional to the sum of dynamic and static acceleration. The effective number of bits of a piezoresistive accelerometer depends on the resolution of changes in resistance as acceleration flexes the cantilever within the accelerometer. Piezoresistive accelerometers are DC-responding with high sensitivities, narrow bandwidth, and outstanding temperature stability. These devices are well suited for measuring low-frequency vibration, motion, and steady-state acceleration.

The two accelerometers 4702, 4704 are positioned at each end of the longitudinal axis of an example motion and orientation sensing module or device. The forward tri-axial accelerometer 4704 tracks the movement of the leading edge or active face of the example instrument. This accelerometer 4704 also tracks the orientation of the cross section of the motion and orientation sensing module or device. The trailing accelerometer 4702 tracks the orientation of the longitudinal axis of the example motion and orientation module or device. The combination of the two tri-axial accelerometers 4702, 4704 can be used to measure heading and yaw in the X-Y plane with high accuracy. The sensing elements within piezoresistive tri-axial accelerometers 4702, 4704 generate analog electrical signals whenever the example motion and orientation sensing module or device is moved or rotated. These analog signals also have a DC component depending on their orientation with respect to the nadir. The combination of the two accelerometers 4702, 4704 assures the motion and orientation sensing module or device can be guided precisely to the target location and orientation in all three Cartesian axes with no discrepancies in pitch, roll, or yaw.

Motion and orientation sensing modules and devices having two accelerometers are not only capable of providing more accurate yaw data, but also two accelerometers provide a level of redundancy that aids in the confirmation that the example instrument is guided accurately to the target position and orientation. If data generated by the two accelerometers 4702, 4704 contain a discrepancy, the tracking procedure may have been compromised and the user can be alerted to the possibility of an exception condition that needs to be addressed.

Multiplexor (MUX) 4606 interfaces the acceleration sensing elements of accelerometers 4702, 4704 with the input to analog conversion circuitry (ADC) 4112. The digital values output by ADC 4112 are transmitted by telemetry transceiver or transmitter 4122 through antenna 4120. This enables an external computer system or other information technology appliance to receive the radio frequency signal broadcast by the motion and orientation sensing module or device for subsequent processing, storage, and display in real time.

Control logic and calibration circuitry 4716 controls the operation of the electronic components within the motion and orientation sensing module or device as well as additional data processing that may be required before transmitting the data to a computer system. Battery 4132, or an equivalent energy storage device, provides the power to operate the electronic circuitry within the motion and orientation sensing module or device. Substrate 4720 provides mechanical support and electrical interconnect for the electronic components and battery within the motion and orientation sensing module or device. The illustrated components and interconnections will enable tracking the movement and orientation of a medical probe, tool, instrument, alignment jig, cutting block, or similar equipment having a motion and orientation sensing module or device, accurately with a high level of precision.

Figure 29:
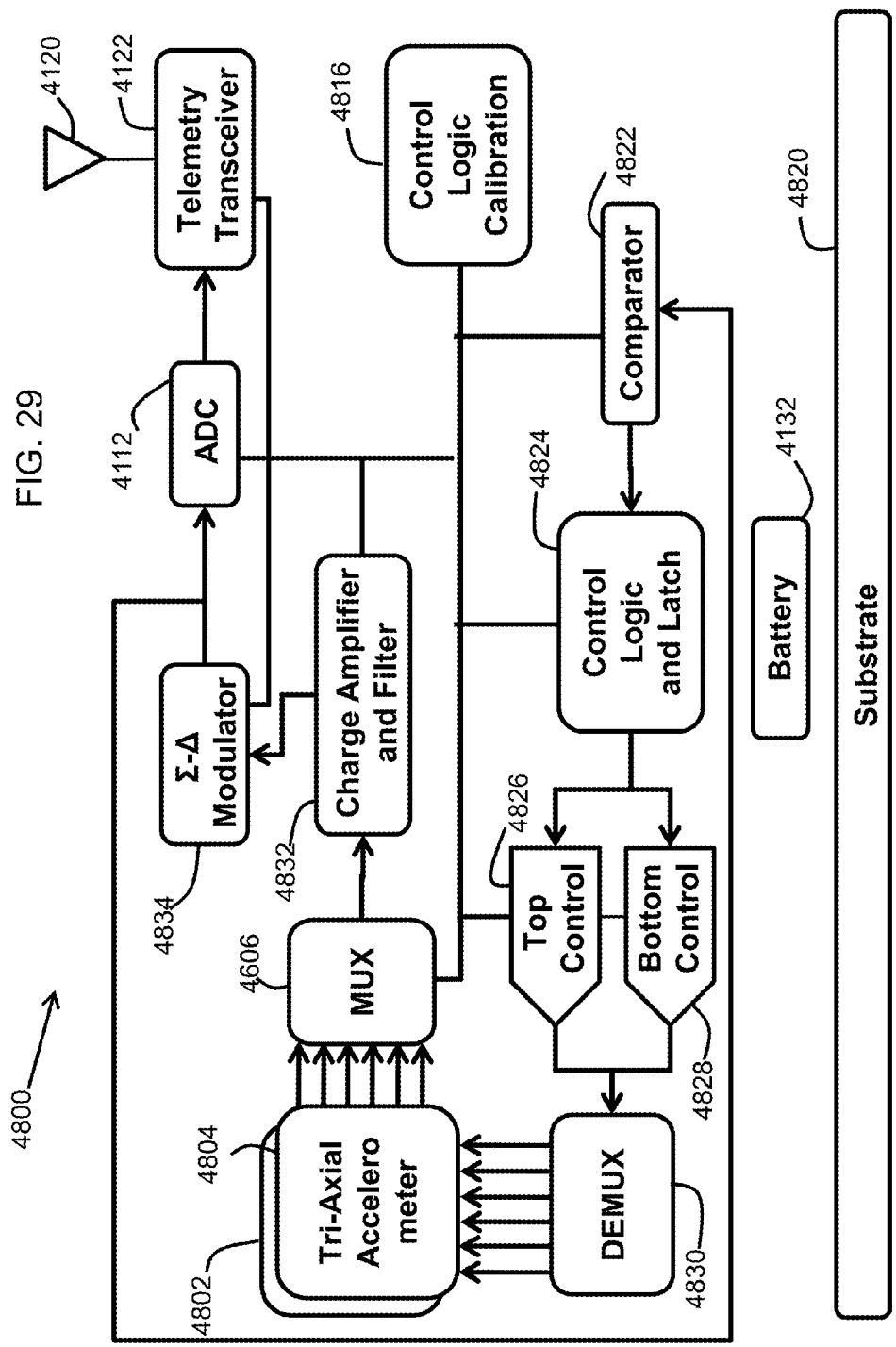
FIG. 29 illustrates a simplified schematic block diagram of an example motion and orientation sensing module or device having tri-axial force-balanced capacitive accelerometers.

FIG. 29 illustrates a simplified schematic block diagram 4800 of an example motion and orientation sensing module or device having tri-axial force-balanced or force feedback capacitance bridge accelerometers. The sensing elements within capacitive tri-axial force-balanced accelerometers generate analog electrical signals whenever an example motion and orientation sensing module or device is moved or rotated as well as a constant output component depending on each accelerometer's orientation with respect to the nadir. In a force-balanced capacitive accelerometer the signal generated by changes in capacitance is amplified and fed back to the sensing structure to counteract the displacement of the moveable capacitor plates. This negative feedback signal is also routed to input of the analog to digital converter. Because the output is dependent only on the feedback force, and displacements of the moveable capacitor plates are minimized, minimizing nonlinearities from the mechanical system and the electronics interface as well. The change in the feedback voltage is proportional to the sum of dynamic and static acceleration. This feedback voltage is output to the analog to digital circuitry for transmission to a computer system having a real-time display. Force-balance capacitive accelerometers are DC-responding with very high sensitivities, narrow bandwidth, and outstanding temperature stability. These devices are well suited for measuring low-frequency vibration, motion, and steady-state acceleration such as gravity.

The effective number of bits of a force-balanced capacitor bridge accelerometer depends on the resolution of changes in capacitance caused by acceleration displacing the moveable plates of the capacitor bridge within the accelerometer. In many instances reduction in nonlinearities and noise improves the effective number of bits achieved with force-balanced capacitor bridge accelerometers.

The two accelerometers 4802, 4804 are positioned at each end of the longitudinal axis of the motion and orientation sensing module or device. The forward tri-axial accelerometer 4804 tracks the movement of the leading edge or active face of a medical instrument. This accelerometer 4804 also tracks the orientation of the cross section of the example motion and orientation sensing module or device. The trailing accelerometer 4802 tracks the orientation of the longitudinal axis of the motion and orientation module or device. The combination of the two tri-axial accelerometers 4802, 4804 can be used to measure heading and yaw in the X-Y plane with high accuracy and assure the motion and orientation sensing module or device can be guided precisely to the target location and orientation in all three Cartesian axes with no discrepancies in pitch, roll, or yaw.

Motion and orientation sensing modules and devices having two accelerometers are not only capable of providing more accurate yaw data, but also two accelerometers provide a level of redundancy that aids in the confirmation that the example instrument is guided accurately to the target position and orientation. If data generated by the two accelerometers 4802, 4804 contain a discrepancy, the tracking procedure may have been compromised and the user can be alerted to the possibility of an exception condition that needs to be addressed.

Multiplexor (MUX) 4606 interfaces the acceleration sensing elements with the input of charge amplifier and filter 4832. The analog signals output by charge amplifier and filter 4832 drive the input of sigma-delta modulator 4834. The signals output by sigma-delta modulator 4834 drive the input of analog to digital conversion circuitry (ADC) 4112. The binary values output by ADC 4112 are transmitted by telemetry transceiver or transmitter 4122 through antenna 4120. This enables an external computer system or other information technology appliance to receive the radio frequency signal broadcast by the motion and orientation sensing module or device for subsequent processing, storage, and display.

The output of sigma-delta modulator 4834 also drives comparator 4822. Comparator 4822 drives control logic and latch 4824. The outputs of control logic and latch 4824 drive the top control 4826 and bottom control 4828 circuits of the feedback loop of the force balanced sensing elements with tri-axial accelerometers 4802, 4804. These controls are connected, through de-multiplexor 4830, to fixed structures within tri-axial accelerometers 4802, 4804. The outputs of the top and bottom controls 4826, 4828 act through fixed structures within tri-axial accelerometers 4802, 4804 to re-center the proof masses that are displaced by movement or tilt of the motion and orientation sensing module or device. Tri-axial accelerometers 4802, 4804 continue to output analog signals through MUX 4606 to charge amplifier 4832 and sigma-delta modulator 4834 until each of the proof masses have been pulled back to their center position. The electrical signal that is required to offset displacement of each proof mass is also the analog input to ADC 4112.

Control logic and calibration circuitry 4816 controls the operation of the electronic components within the example motion and orientation sensing module or device as well as additional data processing that may be required before transmitting the data to a computer system. Battery 4132, or equivalent energy storage device, provides the power to operate the electronic circuitry within the example motion and orientation sensing module or device. Substrate 4820 provides mechanical support and electrical interconnect for the electronic components and battery within the motion and orientation sensing module or device. The illustrated components and interconnection will enable tracking the movement and orientation of a medical probe, tool, instrument, alignment jig, cutting block, or similar equipment having a motion and orientation sensing module or device, accurately with a very high level of precision.

Figure 30:
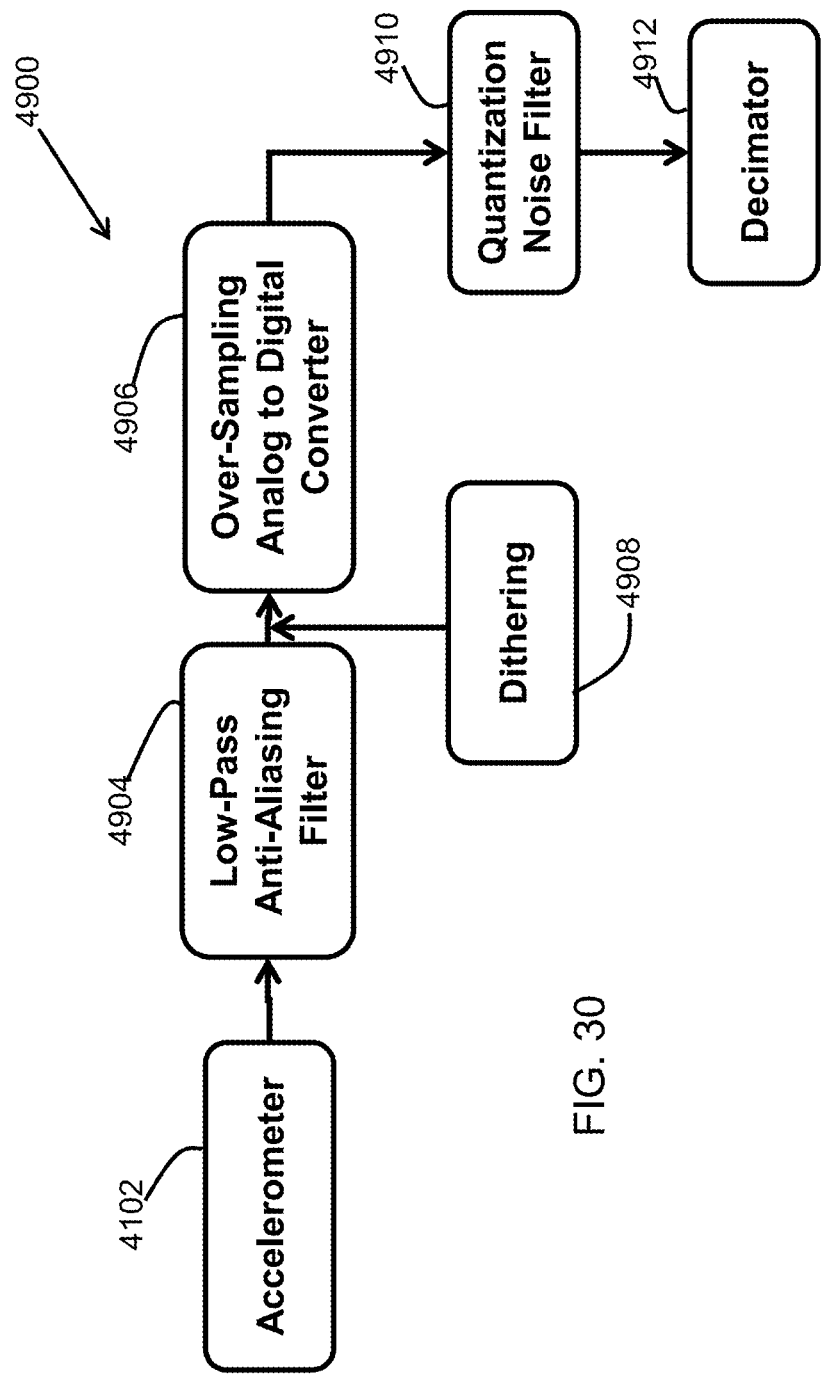
FIG. 30 illustrates a simplified schematic block diagram of a basic generic accelerometer embodiment integrated with filtering, dithering, oversampling, and decimation functions to improve the signal to noise ration and the effective number of bits.

FIG. 30 illustrates a simplified schematic block diagram 4900 of a basic generic accelerometer with the associated circuitry needed to incorporate dithering, oversampling, and decimation functions to improve the signal to noise ration and the effective number of bits. These functions can be combined to extend the effective number of bits of accelerometer 4102 by three or more least-significant-bits. Over-sampling the analog signal from the sensing element of accelerometer 4102 with analog to digital converter 4906 increases the number of discrete samples compromising the digitization of the analog waveform. Low pass anti-aliasing filter 4904 removes the aliases, harmonics, intermodulation products, and other out-of-band signals and reduces the noise passed on to the analog to digital converter 4906. Quantization filter 4910 can reduce quantization noise without reducing the binary output of the ADC 4906. Decimator 4912 digitally down-samples the stream of over-sampled, dithered 4908, digital values. The combination of these functions extends the effective number of bits of the data conversion chain linking physical acceleration to a digitized waveform.

The likelihood of an analog signal being exactly equal to a digital value is small. Therefore, with the combination of dithering and oversampling, it is possible to develop an accurate estimate of the actual value of a point on an analog waveform to greater levels of resolution than the least significant bit of the analog to digital converter 4906. The intermediate result is the creation of more digital readings than specified by the Nyquist frequency. Anti-alias filtering 4904 can be applied before sampling the analog waveform. Only pure sine waveforms are harmonic free. Even then, non-linarites may create harmonics and intermodulation products. Therefore anti-aliasing must remove these harmonic signals and intermodulation products because they introduce nonrandom distortions into the oversampling of dithered analog waveforms. Low-pass anti-aliasing filter 4904 also eliminates other frequencies above the Nyquist frequency before the analog signal is over-sampled. To minimize the risk of higher frequency artifacts falling into the oversampled pass-band and reducing the signal-to-noise ratio.

Dithering 4908 the analog input signal adds a noise component to the signal on the order of a least significant bit or more. Adding this white or Gaussian noise component creates a stochastic variable with a mean value of zero for each voltage sample from the analog waveform. The combination of dithering 4908 and oversampling 4906 enables the interpolation of analog values at each point on the analog waveform. For each desired additional bit of resolution the analog signal can be oversampled by four times. Over sampling by this amount halves the quantization noise introduced by the quantization steps. This can increase the resolution of the measurement by one-half bit.

The greater the samples rate of the analog to digital conversion circuitry the better the representation of the input signal, when samples are subsequently combined. This sample rate may be as little as twice the Nyquist frequency to as much as 256 times the Nyquist frequency, filtering with quantization noise filter 4910 and down-sampling these over-sampled digital values with decimator 4912 increases the signal-to-noise ratio of the analog to digital conversion process. Decimation 4912 down-samples the over-sampled digital values by aggregating groups of over-sampled digital values with the number of digital values within each group depending on the down-sampling divisor. Each down-sampled digital value is right shifted to scale the answer correctly for the increased level of resolution to develop the final high-resolution digital output. The illustrated components and interconnect can enable improvement of the resolution of the analog to digital conversion process, and therefore the least significant bit, by several bits.

Figure 31:
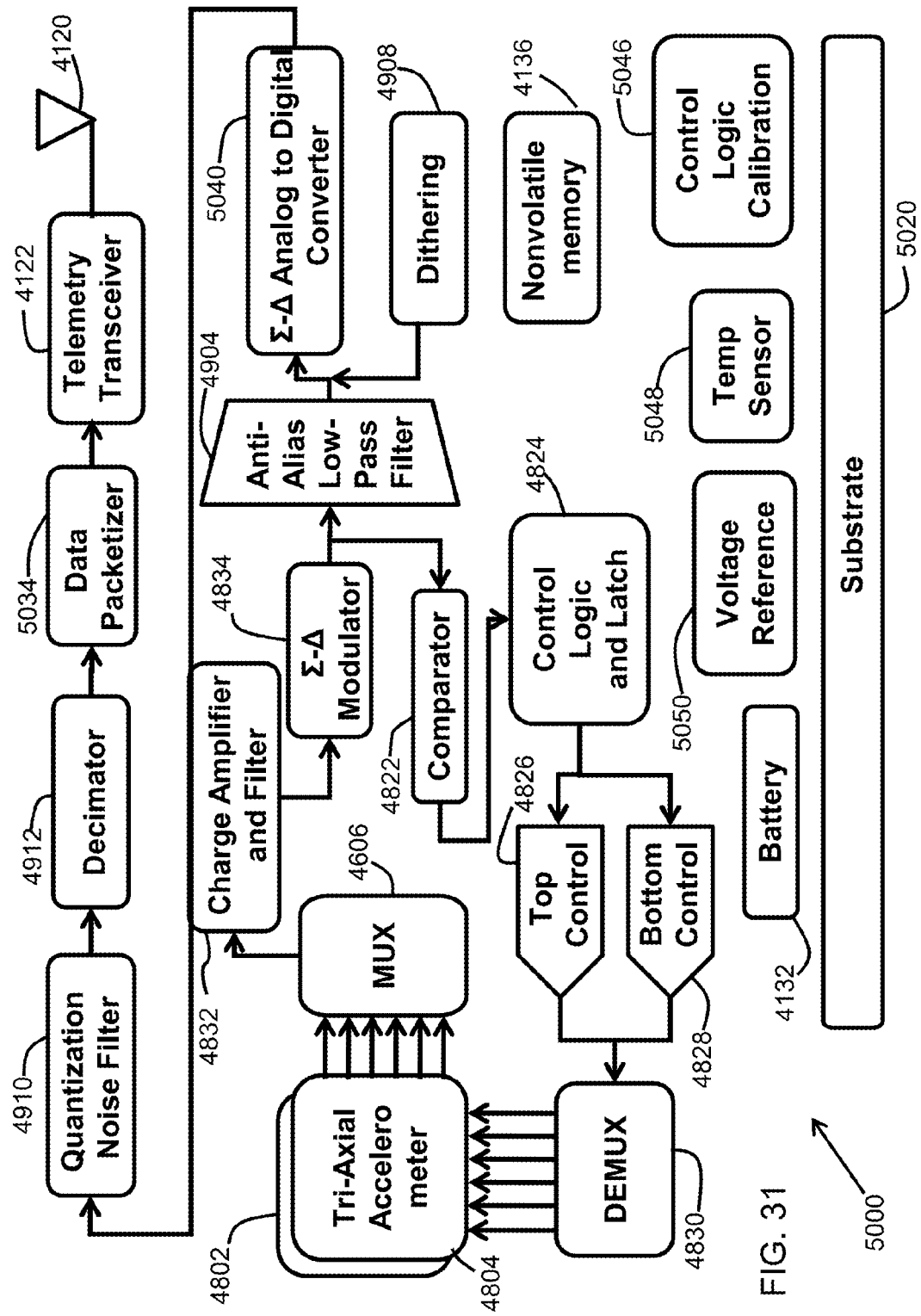
FIG. 31 illustrates a simplified schematic block diagram of an example motion and orientation sensing module or device having tri-axial force-balanced capacitive accelerometers incorporating filtering, dithering, oversampling, decimation, ratiometric, and temperature sensing functions to improve the signal to noise ration and the effective number of bits.

FIG. 31 is a simplified schematic block diagram 5000 of an example motion and orientation sensing module or device having tri-axial force-balanced, force feedback, servo mode capacitance bridge accelerometers, capacitive accelerometers incorporating filtering, dithering, oversampling, decimation, ratiometric, and temperature sensing functions to improve the signal to noise ration and the effective number of bits. The sensing elements within capacitive tri-axial force-balanced accelerometers generate analog electrical signals whenever an example motion and orientation sensing module or device is moved or rotated as well as a constant output component depending on each accelerometer's orientation with respect to the nadir. In a force-balanced capacitive accelerometer the signal generated by changes in capacitance is amplified and fed back to the sensing structure to counteract the displacement of the moveable capacitor plates. This negative feedback signal is also routed to input of the analog to digital to analog converter. Because the output is dependent only on the feedback force, and displacements of the moveable capacitor plates are minimized, minimizing nonlinearities from the mechanical system and the electronics interface as well. The change in the feedback voltage is proportional to the sum of dynamic and static acceleration. This feedback voltage is output to the analog to digital circuitry for transmission to a computer system having a real-time display. Force-balance capacitive accelerometers are DC-responding with very high sensitivities, narrow bandwidth, and outstanding temperature stability. These devices are well suited for measuring low-frequency vibration, motion, and steady-state acceleration such as gravity.

The effective number of bits of a force-balanced capacitor bridge accelerometer depends on the resolution of the feedback voltage required to offset changes in capacitance caused by acceleration of the moveable plates of the capacitor bridge within the accelerometer. This feedback voltage is an analog value, and in continuously operating accelerometers, is a point on an analog waveform. The likelihood of an analog signal being exactly equal to a digital value is small. Therefore, the analog to digital conversion circuitry outputs a digital value either slightly higher or lower than the analog value. This determines the resolution, or least significant bit, of the conversion of acceleration, a continuous physical phenomenon, into a digital value, an electrical code. It is possible to develop a more accurate estimate of the actual value of a point on an analog waveform and achieve greater levels of resolution with the addition of anti-alias filtering, dithering, oversampling, filtering quantization noise, and decimating the filtered, over-sampled signal. This can improve least significant bit of the analog to digital conversion process by several bits.

The sigma-delta modulator is a key component of sigma-delta analog to digital conversion circuitry, but it may not be the same as the sigma-delta modulator used to drive the force-feedback loop in a force-balanced capacitive bridge accelerometer. In practice some of the functions may be merged. But it is important to note that the effective resolution of a Delta-Sigma ADC is dependent on the sample rate. This may not be the same as the optimal sample rate for centering proof masses with the force-feedback control loop.

The two accelerometers 4802, 4804 are positioned at each end of the longitudinal axis of the example motion and orientation sensing module or device. The forward tri-axial accelerometer 4804 tracks the movement of the leading edge or active face of a medical instrument. This accelerometer 4804 also tracks the orientation of the cross section of the example motion and orientation sensing module or device. The trailing accelerometer 4802 tracks the orientation of the longitudinal axis of the motion and orientation module or device. The combination of the two tri-axial accelerometers 4802, 4804 can be used to measure heading and yaw in the X-Y plane with high accuracy and assure the motion and orientation sensing module or device can be guided precisely to the target location and orientation in all three Cartesian axes and with no discrepancies in pitch, roll, or yaw.

Motion and orientation sensing modules and devices having two accelerometers are not only capable of providing more accurate yaw data, but also two accelerometers provide a level of redundancy that aids in the confirmation that the example instrument is guided accurately to the target position and orientation. If data generated by the two accelerometers 4802, 4804 contain a discrepancy, the tracking procedure may have been compromised and the user can be alerted to the possibility of an exception condition that needs to be addressed.

Multiplexor (MUX) 4606 interfaces the force feedback signals from accelerometers 4802 and 4804 with the input of charge amplifier and filter 4832. The analog signals output by charge amplifier and filter 4832 drive the input of sigma-delta modulator 4834. The sigma-delta analog to digital converter 5040 over-samples the analog signal output by the sigma-delta modulator 4834 and filtered through anti-alias low-pass filter 4904. Low-pass anti-aliasing filter 4904 eliminates frequencies above the Nyquist frequency. Harmonics, inter-modulation products, and other high frequency artifacts can be removed before oversampling the analog waveform because they can introduce nonrandom distortions into the oversampled, dithered analog waveforms. Dithering 4908 is introduced into the filtered analog waveform and the analog signal is over-sampled by sigma-delta analog to digital converter 5040. The combination of dithering 4908 and oversampling by the sigma-delta analog to digital converter 5040 enables the interpolation of analog values at each point on the analog waveform. The digital values output by sigma-delta analog to digital conversion circuitry 5040 are filtered through quantization filter 4910 and input to decimator 4912. Filtering with quantization noise filter 4910 and down-sampling the over-sampled digital values with decimator 4912 further increases the signal-to-noise ratio of the analog to digital conversion process. Decimator 4912 digitally down-samples the stream of over-sampled digital values, and in conjunction with dithering 4908 and oversampling 5040, can extend the effective number of bits by several least significant bits. The output of decimator 4912 drives data packetizer 5034. Data packetizer 5034 assembles data into the appropriately formatted packets for transmission by telemetry transceiver or transmitter 4122. The telemetry broadcasts are radiated by antenna 4120. This enables an external computer system or other information technology appliance to receive the radio frequency signal broadcast by the motion and orientation sensing module or device for subsequent processing, storage, and display in real time.

The output of sigma-delta modulator 4834 also drives comparator 4822. Comparator 4822 determines the value of feedback voltage required to force-balance the moveable capacitor plates within the capacitance bridge of the acceleration sensing structure with each of the tri-axial accelerometers 4802, 4804. This is input to control logic and latch 4824. The outputs of control logic and latch 4824 drives the top control 4826 and bottom control 4828 circuits to drive the moveable capacitor plates within the capacitance bridge of the acceleration sensing structure back to their center points. These control signals are connected, through de-multiplexor 4830, to the feedback structures within tri-axial accelerometers 4802, 4804. The outputs of the top and bottom controls 4826, 4828 act through the feedback structures within tri-axial accelerometers 4802, 4804 to re-center proof masses that have been displaced by movement or changes in orientation of the motion and orientation sensing module or device. Tri-axial accelerometers 4802, 4804 continue to output analog signals through MUX 4606 to charge amplifier 4832 and sigma-delta modulator 4834 until each of the proof masses have been returned to their center position. The electrical signal that is required to offset displacement of each proof mass is also the analog input to sigma-delta analog to digital converter 5040 as described in the previous paragraphs.

Control logic and calibration circuitry 5046 controls the operation of the electronic components within the motion and orientation sensing module or device as well as additional data processing that may be required before transmitting the data to a computer system. Data from temperature sensor 5048 is incorporated into the automatic calibration routine executed whenever a motion and orientation sensing module or device is powered up. The data gathered during the automatic calibration routine are stored in nonvolatile memory 4136 within the motion and orientation sensing module or device. Battery 4132, or equivalent energy storage device, provides the power to operate the electronic circuitry within the motion and orientation sensing module or device. Ratiometric design reduces sensitivity of the data capture and conversion circuitry to fluctuations in supply and reference voltages as well as noise on power conductors. Precision voltage reference 5050 provides additional protection against variations in reference voltages. Substrate 5020 provides mechanical support and electrical interconnect for the electronic components and battery within the motion and orientation sensing module or device. The illustrated components and interconnect will enable tracking the movement and orientation of a medical probe, tool, instrument, alignment jig, cutting block, or similar equipment having a motion and orientation sensing module or device, accurately with a very high level of precision.

Figure 32:
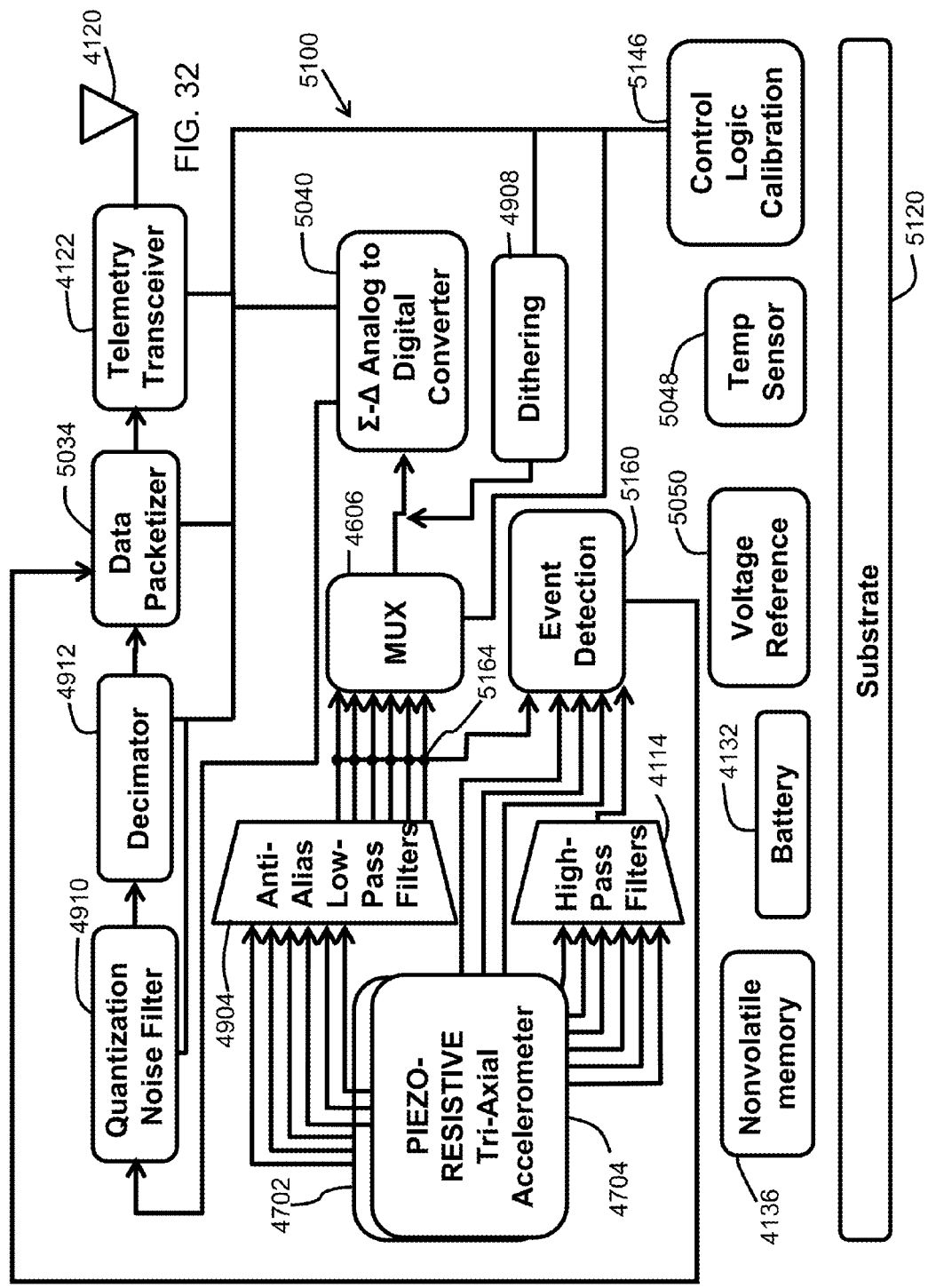
FIG. 32 illustrates a simplified schematic block diagram of an example motion and orientation sensing module or device having tri-axial piezoresistive accelerometers incorporating filtering, dithering, oversampling, decimation, ratiometric, temperature sensing, and event detection functions to improve the effective number of bits and repeatability of data collection and processing.

FIG. 32 is a simplified schematic block diagram 5100 of an example motion and orientation sensing module or device having tri-axial piezoresistive accelerometers incorporating filtering, dithering, oversampling, decimation, ratiometric, temperature sensing, and event detection functions to improve the effective number of bits and repeatability of data collection and processing. The sensing elements within piezoresistive tri-axial accelerometers generate analog electrical signals whenever an example motion and orientation sensing module or device is moved or rotated as well as a constant output component depending on each accelerometer's orientation with respect to the nadir. Piezoresistive accelerometers have a beam or micromachined feature whose resistance changes as it is flexed by movement of the proof mass. The change in resistance produced by flexing the cantilever is proportional to the sum of dynamic and static acceleration. Piezoresistive accelerometers are DC-responding with high sensitivities, narrow bandwidth, and outstanding temperature stability. These devices are well suited for measuring low-frequency vibration, motion, and steady-state acceleration such as gravity.

The effective number of bits of a piezoresistive accelerometer depends on the resolution of changes in resistance as acceleration flexes the resistive cantilever within the accelerometer. Changes in resistance are analog values, and in continuously operating accelerometers, are points on an analog waveform. The likelihood of an analog signal being exactly equal to a digital value is small. Therefore, the analog to digital conversion circuitry outputs a digital value either slightly higher or lower than the analog value. This determines the resolution, or least significant bit, of the conversion of acceleration, a continuous physical phenomenon, into a digital binary value. It is possible to develop a more accurate estimate of the actual value of a point on an analog waveform and achieve greater levels of resolution with the addition of anti-alias filtering, dithering, oversampling, filtering quantization noise, and decimating the filtered, over-sampled signal. This can improve the least significant bit of the analog to digital conversion process by several bits.

The two accelerometers 4702, 4704 are positioned at each end of the longitudinal axis of an example motion and orientation sensing module or device. The forward tri-axial accelerometer 4704 tracks the movement of the leading edge, or active face, of the example instrument. This accelerometer 4704 also tracks the orientation of the cross section of the example motion and orientation sensing module or device. The trailing accelerometer 4702 tracks the orientation of the longitudinal axis of the motion and orientation module or device. The combination of the two tri-axial accelerometers 4702, 4704 can be used to measure heading and yaw in the X-Y plane with high accuracy and assure the motion and orientation sensing module or device can be guided precisely to the target location and orientation in all three Cartesian axes with no discrepancies in pitch, roll, or yaw.

Motion and orientation sensing modules and devices having two accelerometers are not only capable of providing more accurate yaw data, but also two accelerometers provide a level of redundancy that aids in the confirmation that the example instrument is guided accurately to the target position and orientation. If this cannot be achieved to the required level of precision for both accelerometers the tracking procedure may have been compromised and the user can be alerted to the possibility of an exception condition that needs to be addressed.

The accelerometer 4702, 4704 outputs are routed to multiplexor (MUX) 4606 through anti-alias low-pass filter 4904. Low-pass anti-aliasing filter 4904 eliminates frequencies above the Nyquist frequency. Harmonics, intermodulation products, and other high frequency artifacts can be removed before oversampling the analog waveform because they can introduce nonrandom distortions into the oversampling of dithered analog waveforms. The sigma-delta analog to digital converter 5040 over-samples the analog signals output by accelerometers 4702, 4704 and filtered through anti-alias low-pass filter 4904. Dithering 4908 is introduced into the filtered analog waveform and the analog signal is oversampled by sigma-delta analog to digital converter 5040. The combination of dithering 4908 and oversampling by the sigma-delta analog to digital converter 5040 enables the interpolation of analog values at each point on the analog waveform. The digital values output by sigma-delta analog to digital conversion circuitry 5040 are filtered through quantization filter 4910 and input to decimator 4912. Filtering with quantization noise filter 4910 and down-sampling the oversampled digital values with decimator 4912 increases the signal-to-noise ratio of the analog to digital conversion process. Decimator 4912 digitally down-samples the stream of over-sampled digital values, and in conjunction with dithering 4908 and oversampling 5040, can extend the effective number of bits by several least significant bits. The output of decimator 4912 drives data packetizer 5034. Data packetizer 5034 assembles data into the appropriately formatted packets for transmission by telemetry transceiver or transmitter 4122. The telemetry broadcasts are radiated by antenna 4120. This enables an external computer system or other information technology appliance to receive the radio frequency signal broadcast by the motion and orientation sensing module or device for subsequent processing, storage, and display in real time.

High-pass filter 4114 outputs high frequency signals form accelerometers 4702, 4704 to event detection circuitry 5160. These signals are also input to data packetizer 5034 for inclusion in the telemetry packets. In addition to high-pass filter 4114, event detection circuitry 5160 also has inputs from low-pass filter 4904 and directly from the acceleration sensing elements of accelerometers 4702, 4704, the voltage on battery 4132, and readings from temperature sensor 5048. With this combination of inputs it is possible to detect a wide range of potential exception conditions that could compromise the integrity of the tracking procedure and data. The analysis of event detection circuitry 5160 is transmitted to the computer to alert the user.

Data from temperature sensor 5048 are also incorporated into the automatic calibration routine executed whenever a motion and orientation sensing module or device is powered up. The data gathered during the automatic calibration routine are stored in nonvolatile memory 4136 within the motion and orientation sensing module or device.

Control logic and calibration circuitry 5146 controls the operation of the electronic components within the motion and orientation sensing module or device as well as additional data processing that may be required before transmitting the data to a computer system. Battery 4132, or equivalent energy storage device, provides the power to operate the electronic circuitry within the motion and orientation sensing module or device. Ratiometric design reduces sensitivity of the data capture and conversion circuitry to fluctuations in supply and reference voltages as well as noise on power conductors. Precision voltage reference 5050 provides additional protection against variations in reference voltages. Substrate 5120 provides mechanical support and electrical interconnect for the electronic components and battery within the motion and orientation sensing module or device. The illustrated components and interconnect will enable tracking the movement and orientation of a medical probe, tool, instrument, alignment jig, cutting block, or similar equipment having a motion and orientation sensing module or device, accurately with a high level of precision.

Figure 33:
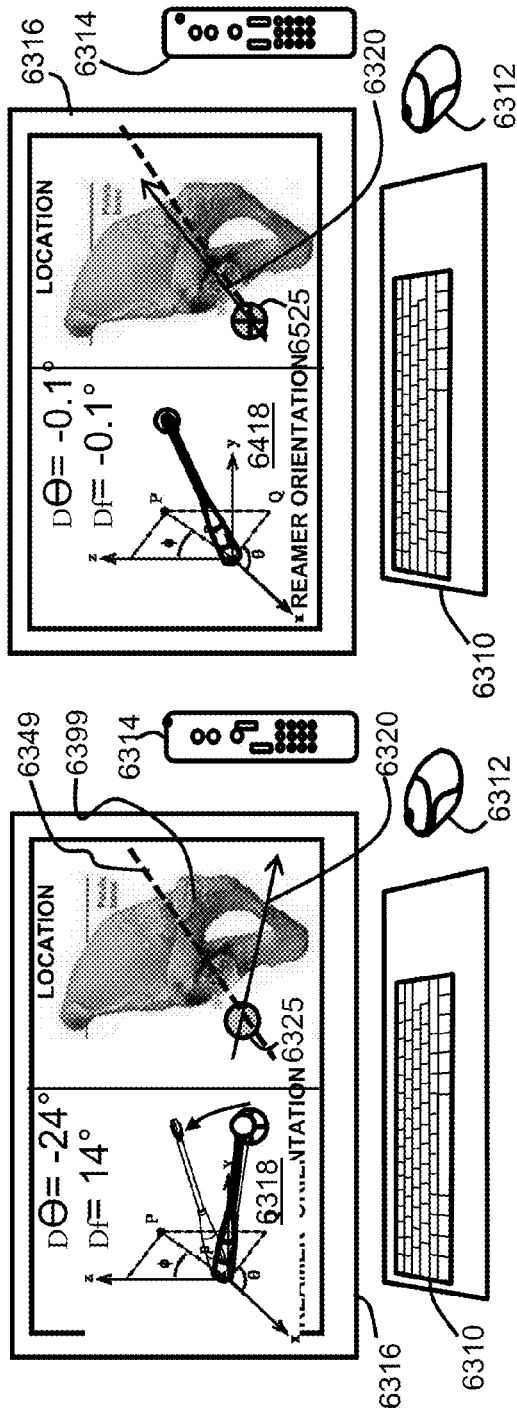
FIG. 33 illustrates a simplified view of a physician using at least one embodiment of a motion and orientation sensing device (e.g., used to guide a reaming tool) with a computer display (e.g., a surgical tracking display system)
Figure 34:
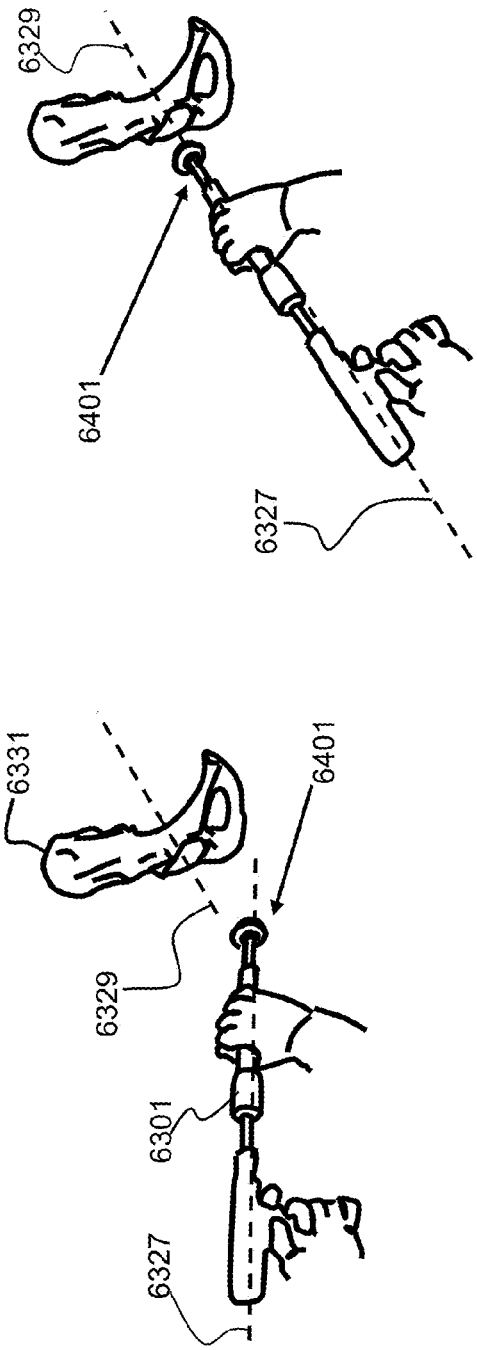
FIG. 34 illustrates a simplified view of a physician using at least one embodiment of a motion and orientation sensing device (e.g., used to guide a reaming tool) with a computer display (e.g., a surgical tracking display system) to orient the tool in a correct orientation.

FIG. 33 illustrates a simplified view of a physician using at least one embodiment of a motion and orientation sensing device (e.g., used to guide a reaming tool 6401) with a computer display (e.g., a surgical tracking display system) and FIG. 34 illustrates a simplified view of a physician using at least one embodiment of a motion and orientation sensing device (e.g., used to guide a reaming tool 6401) with a computer display (e.g., a surgical tracking display system) to orient the surgical tool in a correct orientation.

FIG. 33 is a simplified view of a physician holding an embodiment of a surgical tracking system including a motion and orientation sensing device 6301 (e.g., a surgical device holder portion of a surgical tracking system) with a computer display 6316 (e.g., a surgical tracking display system) of its location and orientation at some distance from a pre-specified target. In the non-limiting example the physician is holding a reamer 6401 used to prepare a hip socket 6331 for artificial hip replacement, where the reamer 6401 includes at least one sensor (e.g., GPS sensor, magnetometer, accelerometer, MEMs devices, gyro) for determining position (e.g., translational x, y, z, translational velocity, acceleration). Reamer 6401 includes a cutting head at a proximal end of the tool. The cutting head removes and shapes bone in the pelvic region to receive a prosthetic component such as an acetabular cup. The performance and reliability of the artificial hip is related to the position and placement of the acetabular cup into the prepared bone surface by reamer 6401. In the example, the pelvic region is reamed by reamer 6401 to support insertion of a prosthetic component. In one embodiment, orientation sensing device 6301 supports reaming of the pelvic region in a predetermined orientation and location that supports installation of a prosthetic component in an optimal position.

Orientation sensing device 6301 can include a clip or attaching mechanism for coupling to reamer 6401. The clip or attaching mechanism can be coupled to a predetermined location to reference to other locations on reamer 6401. Alternatively, orientation sensing device 6301 can be part of reamer 6401. Orientation sensing device 6301 is a tracking element for providing tracking data on reamer 6401. FIG. 33 further illustrates the use of real-time data from an example wireless motion and orientation sensing device to provide real-time visual feedback to aid a physician to guide a medical probe or instrument to a predefined location and contacting that location at a predefined orientation. In this example a view of hip joint 6331 is used as an illustration of an anatomical feature defining a target location and orientation. The reamer 6401 has a device axis 6327, while the hip joint has a desired orientational axis 6329. The desired orientational axis 6329 represents the orientation that the device axis 6327 should be in prior to device (e.g., reamer 6401) contact with the hip joint 6331. A physician can use the computer display 6316 as a remote system to view the device 6401 orientation, for example computer display 6316 illustrates the device axis 6327 as a device orientation line 6320. The desired orientational axis 6329 is displayed as desired orientation line 6349, with the hip 6331 displayed as image 6399. In one embodiment, computer display 6316 as a remote system would be placed outside of the surgical field within an operating room for viewing by the surgeon and team.

As a user moves the surgical tool, along with a motion and orientation sensing device 6301, and reamer 6401, the device orientation line 6320 changes as the user moves the device 6301. Another part of the display 6318 can display the angle needed for the user to rotate the device 6301 so that the device axis 6327 matches the desired orientational axis 6329. Feedback can provide the user information when the device axis 6327 is approaching the desired orientation axis 6329, for example temporally spaced beeps, which get shorter when the correct orientation is approached, or a color display on the screen. Note that the feedback examples described are non-limiting, other methods using a computer display and/or audio can be used.

The computer display 6316 can be connected to a computer 6314 (optionally including a processor that can process tracking data), having a computer keyboard 6310 and a computer mouse 6312. The computer display 6316 displays image 6399, with a target location 6325 and desired orientational line 6349. FIG. 34 illustrates the case where the user has the device 6301 at the proper target location 6325 (e.g., the tip of the reamer is at the correct translational location to begin a procedure) with the device axis 6327 within acceptable tolerance (e.g., within ½ mm positional location and less than 1 degree angular orientation) of the desired orientational axis 6329, where the display illustrates device orientation line 6320 (corresponding to the device axis 6327) and its orientation to the desired orientational line 6349. Note in FIG. 34 the target location indicator 6525 has been changed to provide a feedback symbol (e.g. a cross in a circle).

The example embodiment of a motion and orientation sensing device, which in FIGS. 33 and 34 are incorporated into the device 6301, detects, quantizes, and transmits movement, tilt, and yaw data to computer 6314. This data updates images 6318, 6320, 6349 on display screen 6316 as the user moves the device 6301. The display 6316 illustrates the use of tracking data from an example wireless motion and orientation sensing device to provide real-time visual feedback to aid a physician to guide a medical probe or instrument to a predefined location and contacting that location at a predefined orientation. This enables a user to judge the difference in location and orientation between device 6301 and the target location 6525 and desired orientational axis 6329 within hip joint 6331 while he or she continues to move device 6301. The combination of motion and orientation sensing device, in this example embedded in device 6301, and real-time updates of images aids a user (e.g. physician) to accurately guide device 6301 precisely to the target location and orientation within hip joint 6331.

Referring briefly to FIG. 31, the tracking element of motion and orientation sensing device 6301 of FIG. 33 includes a tri-axial accelerometer 4704, a multiplexer 4606, a converter 4834, an analog to digital converter (ADC) 5040, a transceiver 4122, and control logic 4824. Tri-axial accelerometer 4704 couples to multiplexer 4606 for providing tracking data. Converter 4834 couples to multiplexer 4606 for receiving the tracking data. Alternatively, a magnetometer, gyroscope MEMs chip, or an INS chip can be used to generate tracking data or for redundant measurements. In one embodiment, the tracking element can comprise a first sensor and a second sensor. The first and second sensors can be of different types to provide redundant tracking data when one sensor fails or provides compromised data. Analog to digital converter 5040 couples to converter 4834 to convert analog data to digital data. Transceiver 4122 couples to ADC 5040 to wirelessly transmit the tracking data to a remote system. Control logic 4824 couples to tri-axial accelerometer 4704, multiplexer 4606, converter 4834, and transceiver 4122 to control the position and orientation measurement of reamer 6401. The tracking element of sensing device 6301 is responsive to tracking the movement of the hand holding reamer 6401 in a surgical environment. The tracking element of sensing device 6301 such as tri-axial accelerometer 4704 is sampled at a minimum of 40 times per second to track hand movements. Generating tracking data at 40 times per second provides a precision of the tracking data that has an error of less than 1 millimeter over a path length of 5 meters or less. Similarly, the tracking element of sensing device 6301 provides a precision to provide orientation tracking data within 1 degree. Thus, the tracking element of sensing device 6301 is sufficient to orient and position a tool or prosthetic component for optimal installation for performance and reliability of the component. The tracking element in sensing device 6301 can register or store points in 3D space to support location identification and repositioning. The tracking data is sent to computer display 6316. Computer display 6316 (also known as a remote system) wirelessly receives tracking data from sensing device 6301. The remote system can include control logic, a microprocessor, or digital signal processor to further process the tracking data. Computer display 6316 can include a GUI to support the surgeon in positioning reamer 6401. For example, the remote system can be configured to support positioning of reamer 6401 to a predetermined inclination and anteversion related to anatomical planes. Thus, reamer 6401 can be positioned to ream a region of the pelvis that allows optimal installation of an acetabular cup.

FIG. 33A illustrates a simplified view of a physician using at least one embodiment of a motion and orientation sensing device (e.g., used to guide an impactor tool with a computer display (e.g., a remote system for processing tracking data and displaying and visualizing the data) and FIG. 34A illustrates a simplified view of a physician using at least one embodiment of a motion and orientation sensing device (e.g., used to guide an impactor tool) with a computer display (e.g., a surgical tracking display system) to orient the surgical tool (e.g., impactor or reamer) in a correct orientation. In one embodiment, the motion and orientation sensing device can be removed from reamer 6401 of FIGS. 33 and 34 and coupled to the impactor tool at a predetermined location. Alternatively, the impactor tool can have the motion and orientation sensing device built therein. Landmarks or identifiable points can be used to register points to reference one motion and orientation sensing device to another.

FIG. 33A is a simplified view of a physician holding an embodiment of a surgical tracking system including a motion and orientation sensing device 6661 (e.g., a surgical device holder portion of a surgical tracking system) with a computer display 6616 (e.g., a surgical tracking display system) of its location and orientation at some distance from a pre-specified target. In the non-limiting example illustrated the physician is holding an impactor 6701 used to prepare a hip socket 6631 for artificial hip replacement, where the impactor 6701, having either an attached module 6661 or where the tool includes at least one sensor (e.g., GPS sensor, magnetometer, accelerometer, MEMs devices, gyro) for determining position (e.g., translational x, y, z, translational velocity, acceleration).

Reamer 6401 of FIGS. 33 and 34 shapes bone for receiving a prosthetic component. Referring back to FIGS. 33A and 34A impactor 6701 holds the prosthetic component and is used to forcibly place the prosthetic component in a shaped bone region. In one embodiment, a prosthetic component such as an acetabular cup is placed into the shaped bone region. Motion and orientation sensing device 6661 supports placement of the prosthetic component into the shaped bone region at a precise location and trajectory. FIG. 33A further illustrates the use of real-time data from an example wireless motion and orientation sensing device to provide real-time visual feedback to aid a physician to guide a medical probe or instrument to a predefined location and contacting that location at a predefined orientation. In this example a view of hip joint 6631 is used as an illustration of an anatomical feature defining a target location and orientation. The impactor 6701 has a device axis 6627, while the hip joint has a desired orientational axis 6629. The desired orientational axis 6629 represents the orientation that the device axis 6627 should be in prior to device (e.g., impactor 6701) contact with the hip joint 6631. A physician can use the computer display 6616 to view the device 6661 orientation, for example computer display 6616 illustrates the device axis 6627 as a device orientation line 6620. The desired orientational axis 6629 is displayed as desired orientation line 6649, with the hip 6631 displayed as image 6699.

As a user moves the device 6701 (e.g., impactor), the device orientation line 6620 changes as the user moves the device 6701. Another part of the display 6618 can display the angle needed for the user to rotate the device 6701 so that the device axis 6627 matches the desired orientational axis 6629. Feedback can provide the user information when the device axis 6627 is approaching the desired orientation axis 6629, for example temporally spaced beeps, which get shorter when the correct orientation is approached, or a color display on the screen. Note that the feedback examples described are non-limiting, other methods using a computer display and/or audio can be used. Additionally if the placement of the sensing module 6661 on the second device 6701 is shorter or longer with respect to the desired second device position (e.g., with respect to the second device's tool tip) than the first device 6301, the manufacturing data of both can be used to calculate an offset DX, DY, DY, that must be added/subtracted from the values obtained from sensing module 6661 to orient the second device 6701 (e.g., the tip of the impactor) at the same original translational and angular orientation of the first device 6301 (e.g., the tip of the reamer).

The computer display 6616, can be connected to a computer 6614 (optionally including a processor that can process tracking data), having a computer keyboard 6610 and a computer mouse 6612. The computer display 6616 displays image 6699, with a target location 6625 and desired orientational line 6649. FIG. 34A illustrates the case where the user has the device 6701 at the proper target location 6625 (e.g., the tip of the impactor is at the correct translational location to begin a procedure) with the device axis 6627 within acceptable tolerance (e.g., within ½ mm positional location and less than 1 degree angular orientation) of the desired orientational axis 6629, where the display illustrates device orientation line 6620 (corresponding to the device axis 6627) and its orientation to the desired orientational line 6649. Note in FIG. 34A the target location indicator 6825 has been changed to provide a feedback symbol (e.g. a cross in a circle). In the example, impactor 6701 would be holding an acetabular cup. Motion and orientation sensing device 6661 would support aligning the acetabular cup to the prepared bone surface. The user would be viewing a remote system such as computer display 6616 to ensure correct alignment. A hammer or mallet would be used to impart a force to impactor 6701 that installs the acetabular cup into the pelvic region.

The example embodiment of a motion and orientation sensing device, which in FIGS. 33A and 34A are incorporated into the device 6701, detects, quantizes, and transmits movement, tilt, and yaw data to computer 6614. This data updates images 6618, 6620, 6649 on display screen 6616 as the user moves the device 6701 (e.g., impactor). The display 6616 illustrates the use of tracking data from an example wireless motion and orientation sensing device to provide real-time visual feedback to aid a physician to guide a medical probe or instrument to a predefined location and contacting that location at a predefined orientation. This enables a user to judge the difference in location and orientation between device 6601 and the target location 6825 and desired orientational axis 6629 within hip joint 6631 while he or she continues to move device 6701. The combination of motion and orientation sensing device, in this example embedded in device 6701, and real-time updates of images aids a user (e.g. physician) to accurately guide device 6701 precisely to the target location and orientation within hip joint 6631.

Referring briefly to FIG. 31, the tracking element of motion and orientation sensing device 6661 of FIGS. 33A and 34A includes a tri-axial accelerometer 4704, a multiplexer 4606, a converter 4834, an analog to digital converter (ADC) 5040, a transceiver 4122, and control logic 4824. Tri-axial accelerometer 4704 couples to multiplexer 4606 for providing tracking data. Converter 4834 couples to multiplexer 4606 for receiving the tracking data. Alternatively, a magnetometer, gyroscope MEMs chip, or an INS chip can be used to generate tracking data or for redundant measurements. In one embodiment, the tracking element can comprise a first sensor and a second sensor. The first and second sensors can be of different types to provide redundant tracking data when one sensor fails or provides compromised data. Analog to digital converter 5040 couples to converter 4834 to convert analog data to digital data. Transceiver 4122 couples to ADC 5040 to wirelessly transmit the tracking data to a remote system. Control logic 4824 couples to tri-axial accelerometer 4704, multiplexer 4606, converter 4834, and transceiver 4122 to control the position and orientation measurement of impactor 6701. The tracking element of sensing device 6661 is responsive to tracking the movement of the hand holding impactor 6701 in a surgical environment. The tracking element of sensing device 6661 such as tri-axial accelerometer 4704 is sampled at a minimum of 40 times per second to track hand movements. Generating tracking data at 40 times per second provides a precision of the tracking data that has an error of less than 1 millimeter over a path length of 5 meters or less. Similarly, the tracking element of sensing device 6661 provides a precision to provide orientation tracking data within 1 degree. Thus, the tracking element of sensing device 6661 is sufficient to orient and position a tool or prosthetic component for optimal installation for performance and reliability of the component. The tracking element in sensing device 6661 can register or store points in 3D space to support location identification and repositioning. The tracking data is sent to computer display 6661. Computer display 6616 (also known as a remote system) wirelessly receives tracking data from sensing device 6661. The remote system can include control logic, a microprocessor, or digital signal processor to further process the tracking data. Computer display 6616 can include a GUI to support the surgeon in positioning impactor 6701. For example, the remote system can be configured to support positioning of impactor 6701 to a predetermined inclination and anteversion related to anatomical planes. Thus, impactor 6701 can be positioned to supply a force to install a prosthetic component into a prepared region of the pelvis that allows optimal installation of an acetabular cup.

FIG. 35A illustrates an example of a surgical hip implant 7500 that can be aligned via a motion and orientation sensing system in accordance with at least one exemplary embodiment. The hip implant 7500 can include elements such as a stem 7650, a femoral head 7640, a liner 7630, and an acetabular shell 7625. At least one embodiment can have an embedded device (e.g., a small permanent magnet with a particular axial orientation) to aid in orientation of the other elements of the hip implant 7500. For example, FIG. 35B illustrates the inserted acetabular shell 7625 having a reference magnetic field 7610 inserted into a socket of the hip 7600. One of the other elements in the hip implant 7500 can include a sensor (e.g., the stem 7650 with magnetometer) to measure the reference magnetic field 7610 so that the stem's 7650 insertion into the femoral bone has the correct orientation with respect to the hip joint 7600. Although a non-limiting example of a hip implant is described other surgical procedures can use multiple position and orientation determining sensors. For example FIGS. 36, 38, 39, 40, 42 and 43 illustrate the use of embodiments in knee surgery, while FIGS. 44 and 45 illustrate the use of embodiments in spinal surgery. In a typical hip implant surgery (FIGS. 33, 34, 35A and 35B) the femur is cut into sections. The implant 7500 is inserted into the femur. The femur is then closed (e.g., with a wire for healing) the femoral head 7640 is attached to the stem 7650. The liner 7630 is attached to the femoral head 7640, and the liner 7630 attached to the acetabular shell 7625. The acetabular shell 7625 is inserted into the prepared hip socket (e.g., via reamer 6301). The hip socket is cleared and filled with morselized bone to aid in growth.

Figures 36, 37:
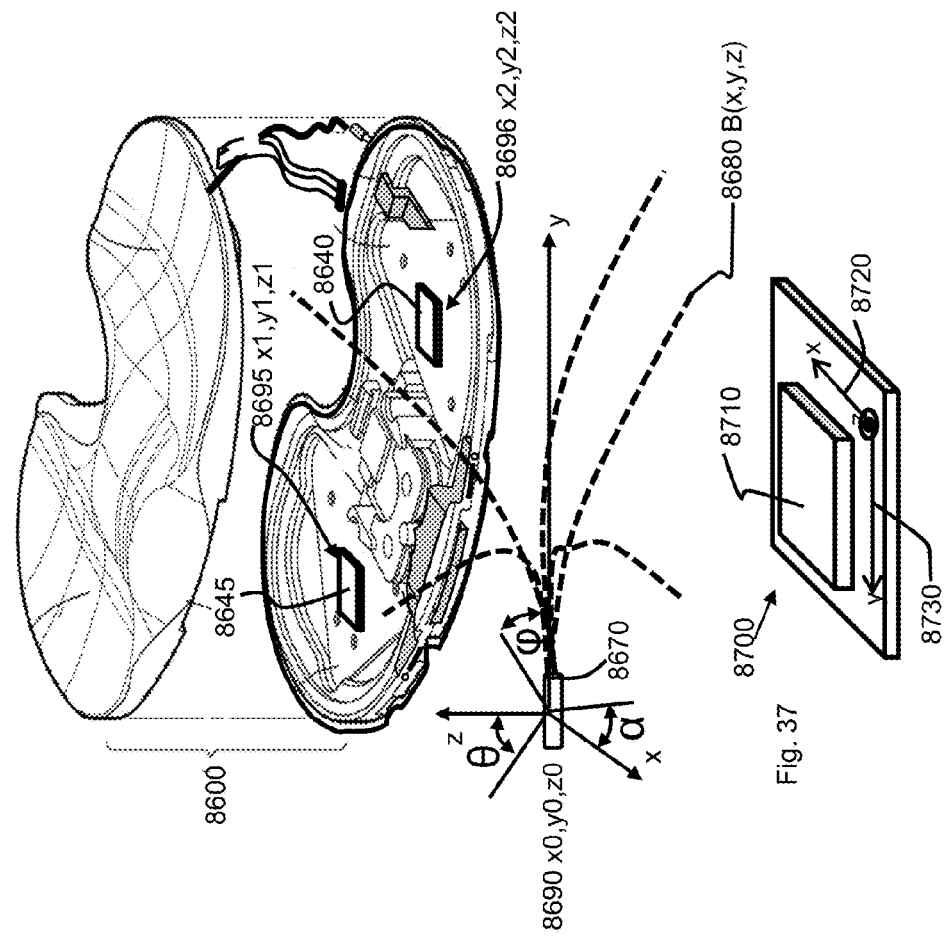
FIG. 36 illustrates an example of an insert device including elements of an orientation sensing system in accordance with at least one exemplary embodiment.
FIG. 37 illustrates an example of an element of an orientation sensing system in accordance with at least one exemplary embodiment.

FIG. 36 illustrates an example of an insert device 8600, used in knee surgery, including elements of an orientation sensing system (e.g., sensors 8645, 8640, reference field emitter 8670) in accordance with at least one exemplary embodiment and FIG. 37 illustrates an example of an element 8700 of an orientation sensing system in accordance with at least one exemplary embodiment. The orientation sensing system (e.g., angular orientation and translational position sensing) can include multiple sensors 8645, 8640, for example GPS MEMS chips, accelerometer chip, gyro chip, magnetometer chip, and magnetic and electric field measuring chips). For example one of the sensors 8645 or 8640 could be a magnetometer that could measure a field strength (e.g. 8680 B(x,y,z)) and the field orientation generated for example by a reference field generator 8670 (e.g., permanent magnet).

As discussed several MEMs type sensors can be used. The following examples are non-limiting and are for illustrative purposes only. For example a Triple Axis Magnetometer Breakout—HMC5843, including a simple I2D interface, 2.5 to 3.3 VDC supply range, a low current draw, with 7 milligauss resolution, and dimensions of about 0.5×0.5" (12.7× 12.7 mm). An additional non-limiting example is a compass, such as Honeywell's HMC5883L, a 3-axis digital compass. Communication with the HMC5883L is through an I2C interface. For the HMC5883L, there is no on-board regulator, so a regulated voltage of 2.16-3.6 VDC should be supplied.

The first sensor 8645 at location 8695 (x1, y1, z1) can be a sensor that measures translational position (x,y,z) and angular orientation ($\alpha,\theta,\phi$) with reference to a reference position (e.g., GPS chip, magnetometer, accelerometer, gyro MEMS chip). Likewise a second sensor 8640 at location 8696 (x2, y2, z2) can additionally measure translational position an angular orientation. Thus the first sensor 8645 can generate a first tracking data set and the second sensor 8640 can generate a second tracking data set. The first tracking data set and the second tracking data set can be combined to form a calculated tracking data set (i.e. a tracking data set calculated from the combination of the first and second tracking data set) that determines the translational position and angular orientation of the device (in this non-limiting example an insert 3600). FIG. 37 illustrates a typical MEMS type sensor 8700, with a sensor element 8710, oriented with respect to a sensor element x axis 8720 and y axis 8730. Examples of such sensors are MEM gyroscopic chips, Draper tuning fork gyroscopes, piezoelectric plate gyroscope, laser ring gyroscopes, magnetoresistive 3 axis sensor, anisotropic magnetoresistive sensors, GPS sensor, accelerometer and other translational and angular orientation sensors know by one of ordinary skill in the art of position sensing.

FIG. 38 illustrates an example of an insert device 9800 implanted and aligned in a knee using an orientation sensing system in accordance with at least one exemplary embodiment. In the non-limiting example illustrated the insert device 9800 emits a field 9810 that can be detected by external sensors such as those in a position and orientation tracking system. The sensors can detect the field 9810 orientation so that additional implants or replacement inserts can be positioned and oriented in the same orientation as the implant 9800. FIG. 39 illustrates an example of the insert device 9800 viewed from a different prospective than in FIG. 38 emitting the field 9910. The spatial dependency of the emitted field provides a method to spatially determine position and orientation of any sensor that can measure the field. Note the field can be magnetic, electric, acoustic, or any other type of spatial dependent field. Any sensor measurement or diagnostics from the insert can be communicated 9820 to a computer 9830, where the information from a sensor and insert can be superimposed to provide a user the relative position and orientation of any external device (e.g. surgical device) with respect to the insert 9800.

Figure 40:
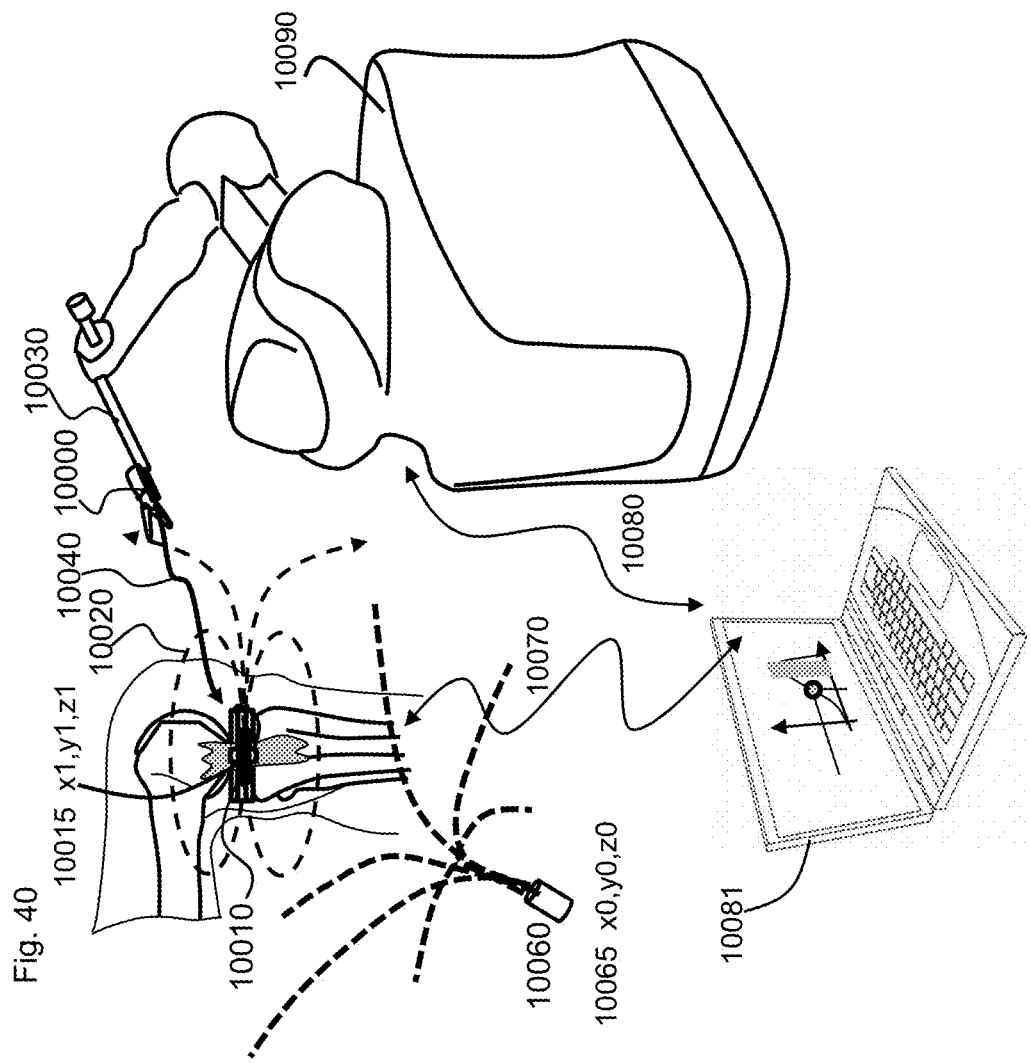
FIG. 40 illustrates a simplified view of a robotic surgical system using at least one embodiment of a motion and orientation sensing device to align and for use of a surgical tool.

FIG. 40 illustrates a simplified view of a robotic surgical system 10090 using at least one embodiment of a motion and orientation sensing device 10030 to align and use a surgical tool 10000. In the illustrated non-limiting example the spatially dependent field 10020 generated by the insert 10010 (having location 10015, x1, y1, z1) and/or reference 10060 (having location 10065 x0, y0, z0) is detected by the sensing device 10030, to provide motion and orientation tracking 10040 of the surgical tool 10000. The insert 10010 and/or the reference 10060 can communicate 10070 with a computer system 10081. Additionally the sensing device 10030 directly or via an interface (e.g., robotic surgical system 10090) can communicate 10080 (e.g., transfer data, such as positional data, orientation data, video data, audio data, image data) with the computer 10081. Where the computer 10081 can combine the data to provide a user a visual representation of the location and orientation of the surgical tool 10000 with respect to the insert 10010 and/or reference 10060.

FIGS. 41A and 41B illustrate a simplified perspective view of an example of a motion and orientation sensing device. FIG. 41A is a simplified perspective view 11100 of an example instrument having an example motion and orientation sensing device containing an optional external field generator 11199, an optional sensor 11151 for detecting external fields, a cover for the device, an interchangeable head, and an example insert or implant 11118 that may be held by the instrument. FIG. 41A illustrates a simplified perspective exploded view of an example medical instrument prior to assembly with an example motion and orientation sensing device, interchangeable head, and example medical insert or prosthetic component or implant. The example motion and orientation sensing device 11136 detects, quantizes, and transmits data defining the movement, tilt, and yaw of an example medical insert, implant, prosthetic component or prostheses. In this exploded view, the example medical instrument 11102 having cavity 11104 and cover 11114 sized to hold the example motion and orientation sensing device 11136 securely within its handle 11106. Example interchangeable head 11116 may be attached to medical instrument 11102 by plugging its base onto coupling on the end of shaft 11108. Example interchangeable head 11116 may be used to hold example medical inserts, prosthetic components, prostheses, or implants 11118. This completed assembly may be used to track the movement and orientation of example medical insert, prosthetic component, prostheses, or implant 11118 in real time.

FIG. 41B illustrates a simplified perspective view of an assembled example medical instrument having an example motion and orientation sensing device for tracking its movement and orientation, an interchangeable head, and an example medical insert or prosthetic component or implant held by the instrument. When assembled the medical instrument 11102, having example motion and orientation sensing device 11136, can be used to track the movement and changes in orientation of example medical insert, prosthetic component, prostheses, or implant 11118. The example motion and orientation sensing device 11136 detects, quantizes, and transmits data defining the movement, tilt, and yaw of example medical insert, prosthetic component, prostheses, or implant 11118 in real time. The example medical instrument 11102, having handle 11106 and shaft 11108, plus cover 11114 securing example motion and orientation sensing device 2006, can be used to track changes in the location and orientation of medical insert, prosthetic component, prostheses, or implant 11118 when positioned securely 11120 within interchangeable head 11116. The external field generator 11199 can generate a field 11197 (e.g., magnetic, electric, acoustic) that can be sensed by other external sensors to identify the position (x,y,z), motion (vx,vy,vz, ax,ay,az), and angular orientation (e.g., spherical coordinate angles with respect to a reference x, y, z axis) of the implant 11118. The optional sensor 11151 for detecting external fields, can be used to measure external fields to determine, position, motion, and/or angular orientation, and can be used with the sensing device 11136 (e.g., optionally including a sensor chip 11157 such as a gyro MEMS chip, accelerometer, GPS, magnetometer) to combine multiple position, motion, and angular orientation data to derive net tracking data of the medical instrument 11102.

FIG. 42 illustrates a simplified view of a physician using at least one embodiment of a motion and orientation sensing device 12206 (e.g., used to guide a surgical tool) with a computer display 12216 (e.g., a surgical tracking display system). FIG. 42 is a simplified view 12200 of a physician holding an embodiment of a surgical tracking system including a motion and orientation sensing device 12206 (e.g., a surgical device holder portion of a surgical tracking system) with a computer display 12216 (e.g., a surgical tracking display system) of its location and orientation at some distance from a pre-specified target. FIG. 42 illustrates the use of real-time data from an example of a wireless motion and orientation sensing device 12206 to provide real-time visual feedback to aid a physician to guide a medical probe 12208 or instrument to contact a predefined location 12221 and angular orientation 12223 of a target. The target location can be tagged with a field generating device, which can generate a spatially unique field 12278. The spatially unique field 12278 can be detected by a sensor (e.g., magnetometer) in the sensing device 12206 and can be used in conjunction with other sensors to improve location and orientation of the medical probe 12208 or instrument.

In this example a sagittal view of knee joint 12204 is used as an illustration of an anatomical feature within which a target location and orientation is defined. Computer display 12216 coupled to computer 12214 (optionally including a processor that can process tracking data), having computer keyboard 12210 and computer mouse 12212, displays image 12220 of a target location 12221 within knee joint 12204. Computer display 12216 also displays image 12220 of the target orientation 12223 within knee joint 12204. For example physician 12202 holds a medical instrument 12208 (surgical device) having an example embodiment of a motion and orientation sensing device 12206 (surgical device holder). Physician 12202 is prepared to move instrument 12208 to the target location 12221 and orientation 12223 within knee joint 12204. The example embodiment of a motion and orientation sensing device 12206 detects, quantizes, and transmits movement, tilt, and yaw data to computer 12214 (e.g., the computer display of a surgical tracking display system). The data can be used to update images 12218, 12220 on display screen 12216 as physician 12202 begins to move instrument 12208.

FIG. 43 is a simplified view 12300 of a physician 12202 holding an embodiment of a surgical tracking system including a motion and orientation sensing device 12206 (e.g., surgical device holder) with a computer display 12216 (e.g., the computer display of a surgical tracking display system) of its location and orientation approaching a pre-specified target. As shown the instrument 12208 has been positioned and oriented to match the target orientation 12318 with a provided error (e.g., within 1 degree) and position 12221 within a positional error (e.g., less than 1 mm).

FIG. 44 is a simplified view 13000 of a physician holding an embodiment of a surgical tracking system including a motion and orientation sensing device with a computer display defining its location and orientation at some distance from a pre-specified target plus a second motion and orientation sensing device pinned to a patient to track any movement of the target. FIG. 44 illustrates the use of real-time data from two example wireless motion and orientation sensing devices (13406, 13423) to provide real-time visual feedback to aid a physician to guide a medical probe or instrument 13408 to a predefined relative location and contacting that location at a predefined relative orientation. In this example a sagittal view spine 13404 is used as an illustration of an anatomical feature having a possible target location 13421 and orientation 13418. In this example, physician 13402 holds a medical instrument 13408 (e.g., surgical device) attached to an example embodiment of a motion and orientation sensing device 13406. Additionally an optional spatially unique field 13457 can be used to aid in instrument 13408 orientation, location, and motion detection.

In a second embodiment a marker motion and orientation sensing device 13423 is affixed to the body of patient 13424 in a fixed position and orientation with respect to target location and orientation 13422, providing movement information that will affect the position and orientation of the target location. Computer display 13416 coupled to computer 13414, having computer keyboard 13410 and computer mouse 13412, displays image 13420 of the distance between instrument 13408 and target location 13422 on spine 13404. Computer display 13416 also displays image of the difference between the orientation of instrument 13408 and the orientation 13418 of target location 13420. Physician 13402 is prepared to move instrument 13408 to the target location and orientation 13418 within spine 13404. The example embodiments of motion and orientation sensing devices 13406, 13423 will detect, quantize, and transmit movement, tilt, and yaw data to computer 13414. Images on display screen 13416 can be updated in real time as physician 13402 begins to move instrument 13408.

FIG. 45 is a simplified view 13100 of a physician holding an embodiment of a surgical tracking system including a motion and orientation sensing device 13406 (e.g., surgical device holder) with a computer display 13416 (e.g., the computer display of a surgical tracking display system) of its location and orientation approaching a pre-specified target. As shown the instrument 13408 has been positioned and oriented to match the target orientation 13518 with a provided error (e.g., within 0.5 degree) and target position 13520 within a positional error (e.g., less than 0.5 mm).

Figure 46:
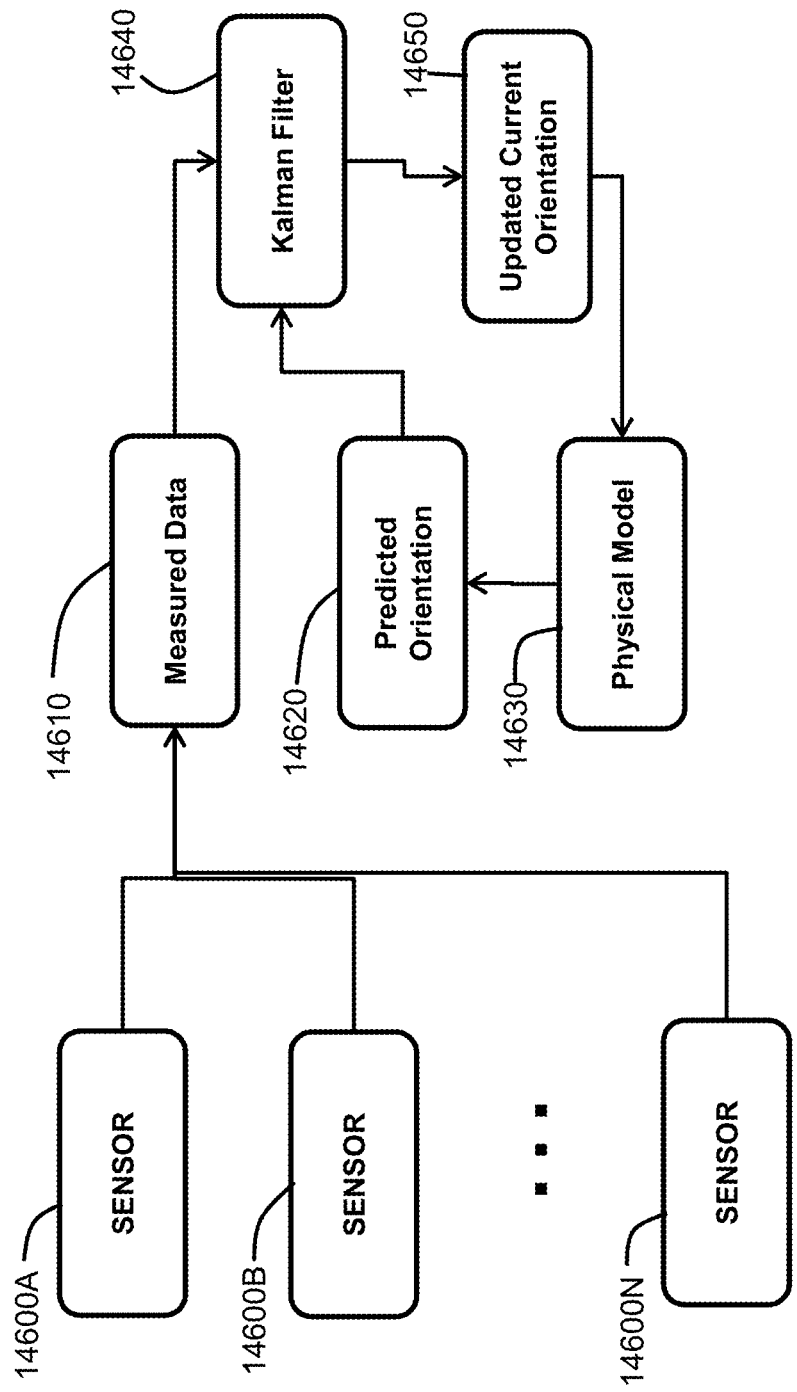
FIG. 46 illustrates a block diagram summarizing the combination of various sensor data to improve orientation determination in accordance with at least one embodiment.

FIG. 46 illustrates a block diagram summarizing the combination of various sensor data to improve orientation determination in accordance with at least one embodiment. As illustrated, data from several sensors 14600A, 14600B, and 14600N (e.g., MEMs gyroscope, magnetometer, accelerometer, GPS, and other position, motion, and orientation devices as known by one of ordinary skill in the art) can be combined into measured data 14610 and fed into a Kalman Filter 14640 to calculate an updated position, location, and orientation 14650. A physical model 14630 can predict the next position, motion, and orientation 14620, which can also be fed into the Kalman Filter 14640 to aid in providing an updated current orientation 14650. The Kalman filter is a recursive estimator, thus only the estimated state from the previous time step and the current measurement are needed to compute the estimate for the current state. The Kalman filter has a predictive stage and an update stage. The predictive stage uses the state estimate from the previous time step to produce an estimate of the state at the current time step. This predicted state estimate is also known as the a priori state estimate because, although it is an estimate of the state at the current time step, it does not include observation information from the current time step. In the update phase, the current a priori prediction is combined with current observation information to refine the state estimate. This improved estimate is termed the a posteriori state estimate.

Various sensors, for example the accelerometers and magnetometers can provide multiple sets of data that can be combined in a filter (e.g., a Kalman Filter). If either sensor fails to provide data the other sensor's data can be used as observations/measurements entered into the filter. Accuracy is improved by using multiple combinations of the various generated data sets.

At least one exemplary embodiment is directed to a surgical tracking system comprising: a surgical device holder; a first sensor (e.g., GPS MEMs chip, accelerometer, MEMs gyro, magnetometer), where the first sensor is configured to produce a first tracking data set (e.g., position (x, y, z), motion (vx, vy, vz, ax, ay, az), and angular orientation (spherical coordinates, $\theta,\phi,\psi$)); a second sensor, where the second sensor is configured to produce a second tracking data set; and a tracking element, where the surgical device holder is configured to hold a surgical device, where the tracking element is configured to track the position of the surgical device holder, where the surgical device holder and the tracking element are operatively connected, where the surgical device holder is configured to be grasped by a user, where the tracking element is configured to produce tracking data, where the tracking data is produced by using the first tracking data set and the second tracking data set, where the tracking data can be used by a processor to provide a position with a position accuracy of a portion of the surgical device holder to within +/−1 mm of the actual translational location over a path length of less than 5 m.

Additional exemplary embodiment of the surgical tracking system can use the tracking data to provide an angular orientation of the portion of the surgical device holder, where the accuracy of the angular orientation of the portion of the surgical device holder is within 1 degree.

Additional exemplary embodiments can use the tracking data to provide a reposition accuracy of the portion of the surgical device holder to within of at least 1.0 mm over a path length of less than 5 m from an initial position.

Additional exemplary embodiments can use the tracking data to provide an angular reorientation accuracy of the portion of the surgical device holder to within of at least 1 degree over a path length of less than 5 m from an initial orientation.

Additional exemplary embodiments can include an exterior tracking system, where the exterior tracking system provides a third tracking data set, that can be combined with the first and second tracking data sets to obtain the tracking data, where the tracking data can be used by a processor to calculate the position and orientation of the surgical device holder.

At least one exemplary embodiment is directed toward a method of surgical tracking display that can be used by a user to determine the placement of a tool in relation to a patient. For example moving a surgical tool (e.g., scalpel, reamer). The surgical tracking display system can also be used to position a surgical tool to a location and orientation originally determined by initially positioning a probe. To initially orient the probe a user can move the probe device toward a patient. In at least one exemplary embodiment the probe can be displayed as a simulated probe on a display. As the user moves the probe the simulated probe moves on the display. Various marks can be used to display the simulated probe (e.g., arrow, stick figure outline of probe). The patient or at least a portion of the patient can also be displayed, where the simulated probe moves in relation to the displayed patient portion. A user can rotate and move the probe to a location and orientation that a user or simulations indicate is the optimum location and orientation or a desired location and orientation, called the target location and target orientation. The target location and target orientation can be displayed as target location mark (e.g., a circle with a cross within) and target orientation mark (e.g., an arrow). Once the target locations and target orientation are determined and displayed, the user can then replace the probe with a surgical device. Then a different or the same user can move the surgical device toward the patient, where the surgical device is displayed as a simulated surgical device. The surgical device can be displayed on the display as a simulated surgical device, which moves as the user moves the surgical device. The simulated surgical device moves in relation to the displayed patient portion. The user can then rotate and move the surgical device until the simulated surgical device is at about the target location mark and the simulated surgical device is about aligned with the target orientation mark.

In at least one exemplary embodiment a feedback can be provided to the user as the surgical device is moved to aid the user in positioning the simulated surgical device at about the target location mark and aligning the simulated surgical device with the target orientation mark. For example the feedback can be visual (e.g., lights attached to the handle 11106 or sensor 11151), haptic feedbacks (e.g., warming of the handle as one get closer, cooler as one moves away from the target location and target orientation or vice versa), and acoustic feedback (e.g., a tone that clicks faster when one gets closer to the target location and target orientation). In at least one exemplary embodiment, the visual feedback includes colored lights, where the color changes as a user positions the surgical device location and orientation closer to the target location and target orientation.

At least one exemplary embodiment includes a haptic feedback, where the haptic feedback is the temperature of a handle on the surgical device, where the temperature changes as the simulated surgical device is positioned at about the target location mark and aligned with the target orientation mark. Note that feedback can be set to get a surgical device within a chosen distance and orientation angle of the target location and target orientation. For example a feedback can indicate that the surgical device is at the target position and target orientation after rotating and moving the surgical device, where the surgical device location is less than 3 mm from the target location and a surgical device orientation, is less than 3 degrees from the target orientation.

While the present invention has been described with reference to particular embodiments, those skilled in the art will recognize that many changes may be made thereto without departing from the spirit and scope of the present invention. Each of these embodiments and obvious variations thereof is contemplated as falling within the spirit and scope of the claimed invention, which is set forth in the claims. While the subject matter of the invention is described with specific examples of embodiments, the foregoing drawings and descriptions thereof depict only typical embodiments of the subject matter and are not therefore to be considered to be limiting of its scope, it is evident that many alternatives and variations will be apparent to those skilled in the art. Thus, the description of the invention is merely descriptive in nature and, thus, variations that do not depart from the gist of the invention are intended to be within the scope of the embodiments of the present invention. Such variations are not to be regarded as a departure from the spirit and scope of the present invention.

While the present invention has been described with reference to embodiments, it is to be understood that the invention is not limited to the disclosed embodiments. The scope of the following claims is to be accorded the broadest interpretation so as to encompass all modifications, equivalent structures and functions. For example, if words such as "orthogonal", "perpendicular" are used the intended meaning is "substantially orthogonal" and "substantially perpendicular" respectively. Additionally although specific numbers may be quoted in the claims, it is intended that a number close to the one stated is also within the intended scope, i.e. any stated number (e.g., 90 degrees) should be interpreted to be "about" the value of the stated number (e.g., about 90 degrees).

As the claims hereinafter reflect, inventive aspects may lie in less than all features of a single foregoing disclosed embodiment. Thus, the hereinafter expressed claims are hereby expressly incorporated into this Detailed Description of the Drawings, with each claim standing on its own as a separate embodiment of an invention. Furthermore, while some embodiments described herein include some but not other features included in other embodiments, combinations of features of different embodiments are meant to be within the scope of the invention, and form different embodiments, as would be understood by those skilled in the art.

What is claimed is:

1. A surgical tracking system comprising:
    a surgical device holder comprising;
        a tracking element comprising:
            a first sensor, where the first sensor is configured to provide a first tracking data set comprising X, Y, Z location data in real-time;
            a second sensor, where the second sensor is configured to provide a second tracking data set comprising X, Y, Z location data in real-time where the tracking element is configured to track the position of the surgical device holder, where the surgical device holder, where the surgical device holder is configured to be grasped by a user, where the tracking element is configured to produce tracking data, where the tracking data is produced by using the first tracking data set and the second tracking data set, where the first sensor and the second sensor are located on or in the surgical device holder, and where the first tracking data set and the second tracking data set are combined; and
    a surgical device where the surgical device holder is configured to hold the surgical device where the tracking data can be used by a processor to provide a position with a position accuracy of a portion of the surgical device holder to within +/−1 mm of the actual translational location over a path length of less than 5 m and where the surgical device is configured to guide the surgical device to a location during surgery.

2. The surgical tracking system according to claim 1, where the tracking data can be used by a processor to provide an angular orientation of the portion of the surgical device holder, where the accuracy of the angular orientation of the portion of the surgical device holder is within 1 degree.

3. The surgical tracking system according to claim 2, where at least one of the first sensor and the second sensor include an accelerometer.

4. The surgical tracking system according to claim 2, where at least one of the first sensor and the second sensor include an INS chip.

5. The surgical tracking system according to claim 2, where at least one of the first sensor and the second sensor include an acoustical transducer.

6. The surgical tracking system according to claim 2, where at least one of the first sensor and the second sensor include a magnetometer.

7. The surgical tracking system according to claim 2, where at least one of the first sensor and the second sensor include a gyroscopic MEMS chip.

8. The surgical tracking system according to claim 1, where the tracking data can be used by a processor to provide a reposition accuracy of the portion of the surgical device holder to within of at least 1.0 mm over a path length of less than 5 m from an initial position.

9. The surgical tracking system according to claim 8, where the tracking data can be used by a processor to provide an angular reorientation accuracy of the portion of the surgical device holder to within of at least 1 degree over a path length of less than 5 m from an initial orientation.

10. The surgical tracking system according to claim 9, further comprising
    an exterior tracking system, where the exterior tracking system provides a third tracking data set, that can be combined with the first and second tracking data sets to obtain the tracking data, where the tracking data can be used by a processor to calculate the position and orientation of the surgical device holder.

11. The surgical tracking system according to claim 8, where the portion of the surgical device holder is a portion that is configured to be connected to the surgical device.

12. The surgical tracking system according to claim 11, where the surgical device is a knee replacement part.

13. The surgical tracking system according to claim 11, where the surgical device is a hip replacement part.

14. The surgical tracking system according to claim 11, where the surgical device is a spine replacement part.

15. The surgical tracking system according to claim 1 wherein the
    the first sensor comprises a first tri-axial accelerometer; and
    the second sensor comprises a second tri-axial accelerometer;
    a multiplexer (MUX) coupled to the first accelerometer and the second accelerometer;
    a capacitance to voltage converter coupled to the multiplexer;
    an analog to digital converter (ADC) coupled to the capacitance to voltage converter;
    a transceiver coupled to the analog to digital converter configured to send position data from the system; and
    control logic coupled to the first tri-axial accelerometer, the multiplexer, the ADC converter, and the transceiver configured to control position measurement.

16. The surgical tracking system according to claim 1 wherein the the first sensor comprises a first tri-axial gyroscope; and
the second sensor comprises a second tri-axial gyroscope;
a multiplexer (MUX) coupled to the first accelerometer and the second accelerometer;
a capacitance to voltage converter coupled to the multiplexer;
an analog to digital converter (ADC) coupled to the capacitance to voltage converter;
a transceiver coupled to the analog to digital converter configured to send position data from the system; and
control logic coupled to the first tri-axial accelerometer, the multiplexer, the ADC converter, and the transceiver configured to control position measurement.

17. A surgical tracking system comprising:
a surgical device holder or a surgical device comprising:
  a first sensor, where the first sensor is configured to provide a first tracking data set comprising X, Y, Z location in real-time;
  a second sensor, where the second sensor is configured to provide a second tracking data set comprising X, Y, Z location in real-time;
  a transmitter configured to transmit position and location data from the surgical device where the first and second sensors are on the surgical device or surgical device holder; and
a processor, where the processor is configured to receive a first tracking data set from the first sensor, where the processor is configured to receive a second tracking data set from the second sensor, where the processor is configured to use the first and second tracking data set to track a position with a position accuracy of a portion of the surgical device holder or surgical device to within +/−1 millimeter of the actual translational location over a path length of less than 5 meters and wherein the first and second tracking data set is stored in memory coupled to the processor.

18. The surgical tracking system according to claim 17, where the first data type is at least one of GPS data, magnetic field data, electric field data, accelerometer data, and gyroscopic data.

19. The surgical tracking system according to claim 17, where the second data type is at least one of GPS data, magnetic field data, electric field data, accelerometer data, and gyroscopic data.

20. The surgical tracking system according to claim 17, where the processor combines the first data set and the second data set into a Kalman Filter.

21. The surgical tracking system according to claim 17 wherein the the first sensor comprises a first tri-axial accelerometer; and
the second sensor comprises a second tri-axial accelerometer;
a multiplexer (MUX) coupled to the first accelerometer and the second accelerometer;
a capacitance to voltage converter coupled to the multiplexer;
an analog to digital converter (ADC) coupled to the capacitance to voltage converter;
a transceiver coupled to the analog to digital converter configured to send position data from the system; and
control logic coupled to the first tri-axial accelerometer, the multiplexer, the ADC converter, and the transceiver configured to control position measurement.

22. The surgical tracking system according to claim 17 wherein the the first sensor comprises a first tri-axial gyroscope; and
the second sensor comprises a second tri-axial gyroscope;
a multiplexer (MUX) coupled to the first accelerometer and the second accelerometer;
a capacitance to voltage converter coupled to the multiplexer;
an analog to digital converter (ADC) coupled to the capacitance to voltage converter;
a transceiver coupled to the analog to digital converter configured to send position data from the system; and
control logic coupled to the first tri-axial accelerometer, the multiplexer, the ADC converter, and the transceiver configured to control position measurement.

* * * * *